United States Patent
Iwanaga et al.

(10) Patent No.: US 9,157,885 B2
(45) Date of Patent: Oct. 13, 2015

(54) METHOD OF ELECTROCHEMICALLY DETECTING TARGET SUBSTANCE, METHOD OF ELECTROCHEMICALLY DETECTING ANALYTE, TEST CHIP, AND DETECTION SET

(75) Inventors: Shigeki Iwanaga, Kobe (JP); Hiroya Kirimura, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 581 days.

(21) Appl. No.: 13/244,377

(22) Filed: Sep. 24, 2011

(65) Prior Publication Data

US 2012/0080324 A1  Apr. 5, 2012

(30) Foreign Application Priority Data

Sep. 30, 2010 (JP) ................ 2010-222191
Sep. 14, 2011 (JP) ................ 2011-200815

(51) Int. Cl.
*G01N 33/487* (2006.01)
*G01N 27/327* (2006.01)

(52) U.S. Cl.
CPC .................. *G01N 27/3278* (2013.01)

(58) Field of Classification Search
USPC .......... 204/400, 412, 416; 205/775, 687, 792; 435/6.1–6.19, 287.2, 285.2
See application file for complete search history.

(56) References Cited

U.S. PATENT DOCUMENTS

| | | | |
|---|---|---|---|
| 5,372,930 A * | 12/1994 | Colton et al. ............... | 435/6.19 |
| 5,776,672 A | 7/1998 | Hashimoto et al. | |
| 5,972,692 A | 10/1999 | Hashimoto et al. | |
| 2003/0080284 A1 | 5/2003 | Wake et al. | |
| 2009/0035187 A1* | 2/2009 | Schleifer et al. ............ | 422/102 |
| 2009/0294305 A1 | 12/2009 | Bekki et al. | |
| 2010/0108539 A1 | 5/2010 | Iwanaga et al. | |
| 2010/0112578 A1 | 5/2010 | Iwanaga et al. | |
| 2013/0344498 A1* | 12/2013 | Marziali et al. ............. | 435/6.12 |

FOREIGN PATENT DOCUMENTS

| | | | |
|---|---|---|---|
| GB | 2462062 A * | 1/2010 | |
| JP | 2005-134372 A | 5/2005 | |
| JP | 2006-98110 A | 4/2006 | |
| JP | 2006-516721 A | 7/2006 | |
| JP | 2008-209323 A | 9/2008 | |
| JP | 2010-133933 A | 6/2010 | |
| JP | 2012-117888 A | 6/2012 | |
| WO | 2007/116811 A1 | 10/2007 | |
| WO | 2009/068862 A1 | 6/2009 | |

* cited by examiner

Primary Examiner — Gurpreet Kaur
(74) Attorney, Agent, or Firm — Sughrue Mion, PLLC

(57) ABSTRACT

The present invention provides a method for electrochemically detecting a target substance and a method for electrochemically detecting an analyte using a probe holding substrate with a probe for trapping a target substance or an analyte held on the substrate body as well as a test chip and a detection set using the above detection methods.

11 Claims, 40 Drawing Sheets

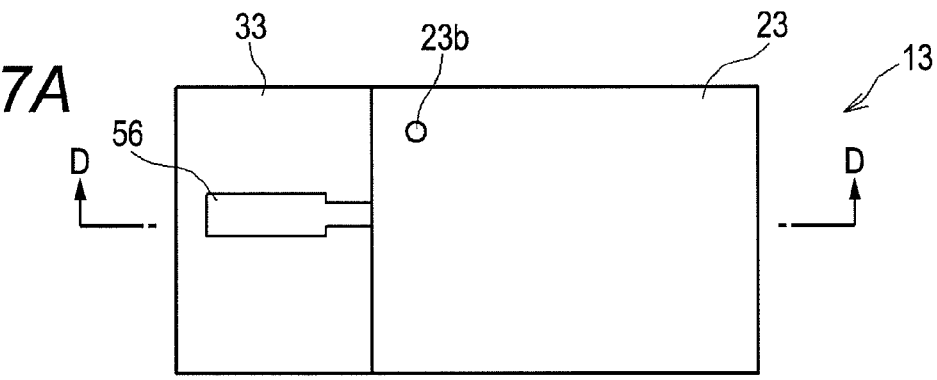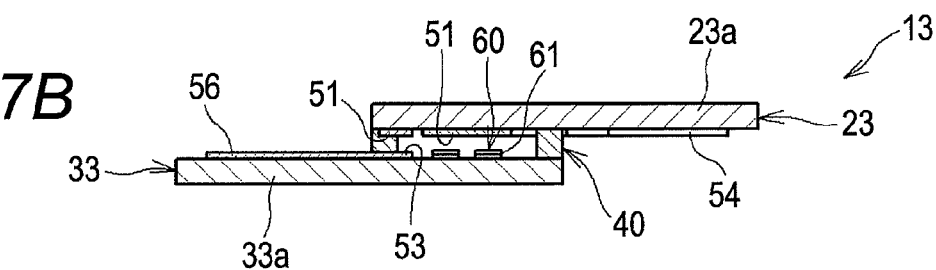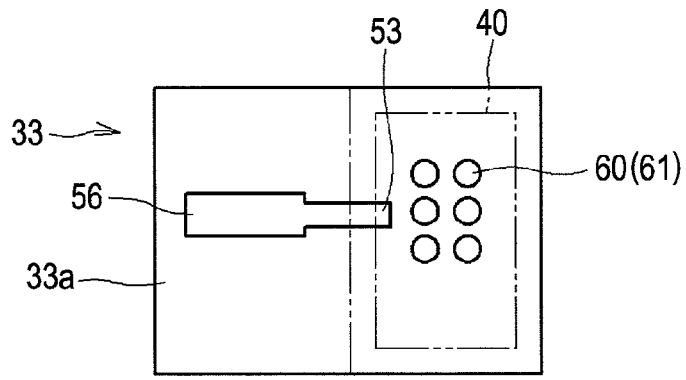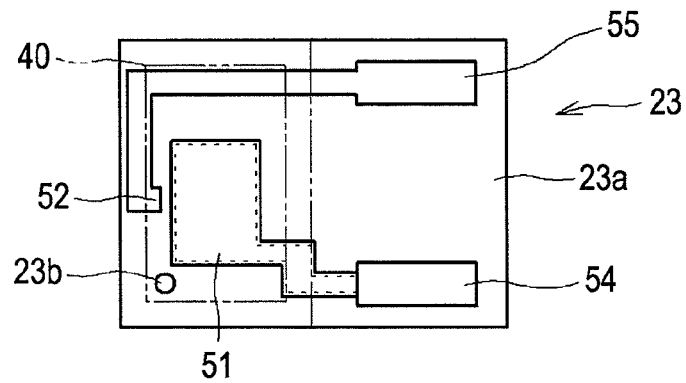

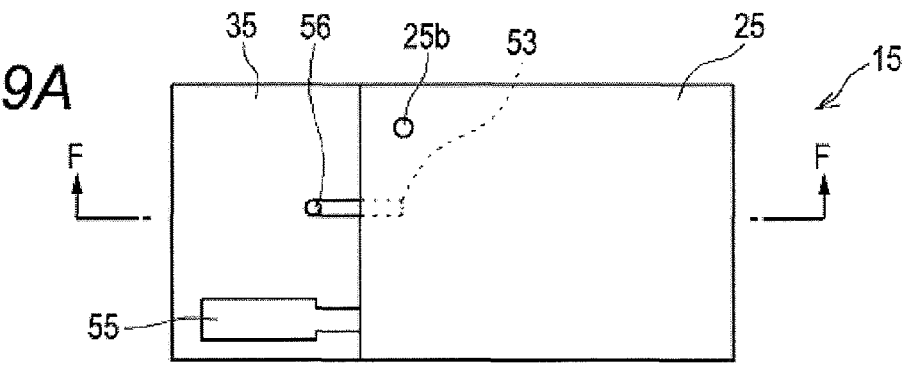
FIG. 9A
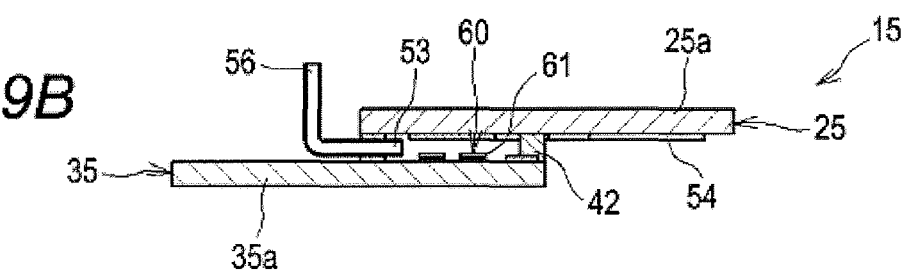
FIG. 9B
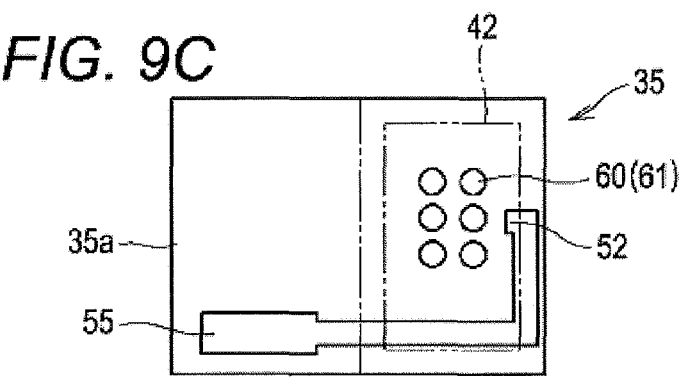
FIG. 9C
FIG. 9D
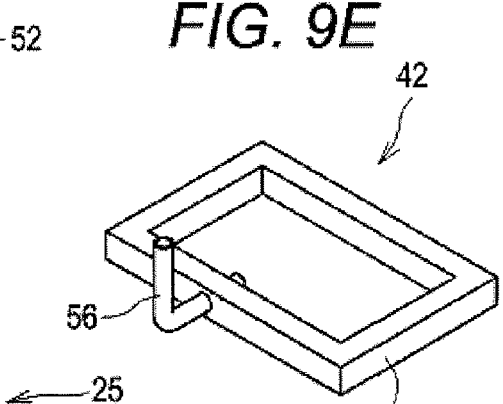
FIG. 9E

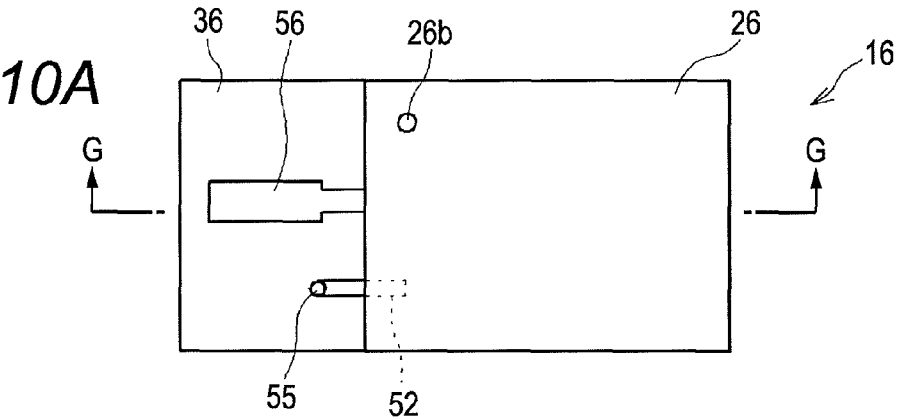
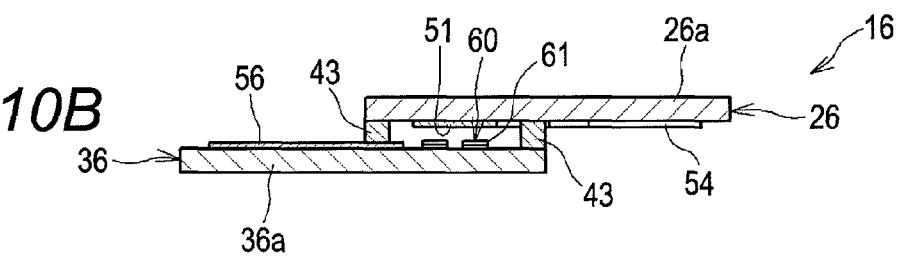
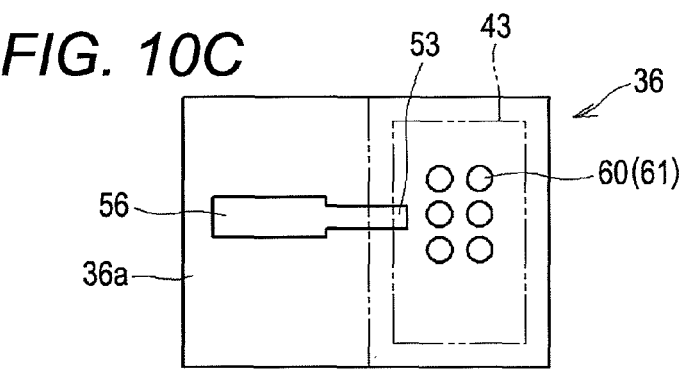
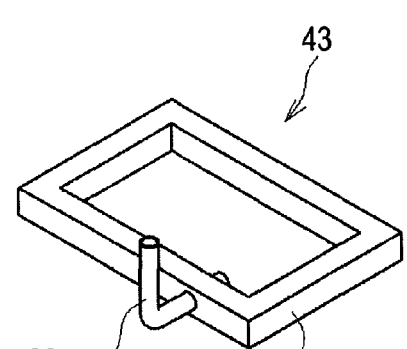
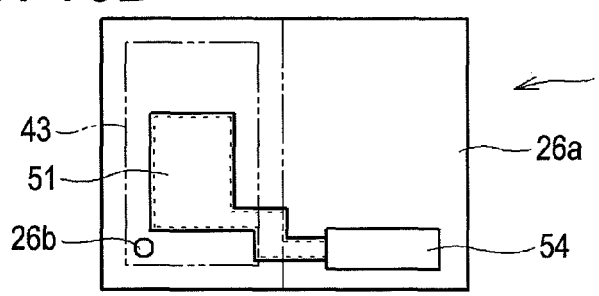

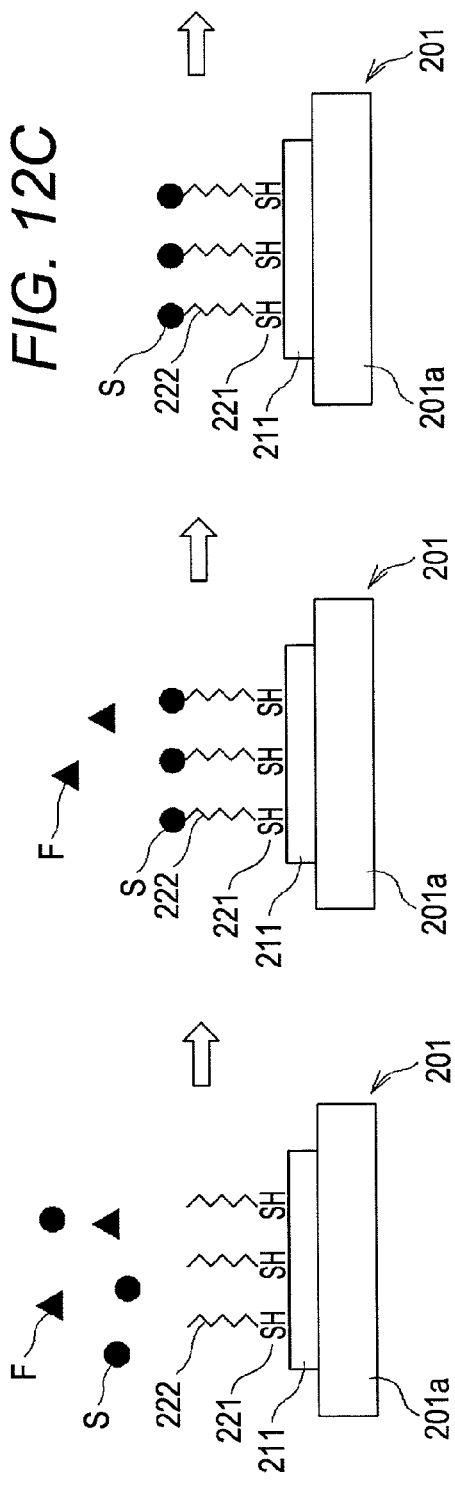

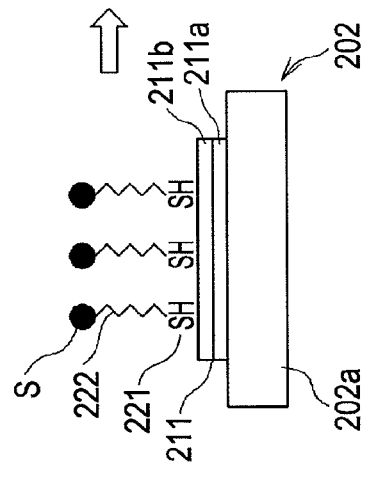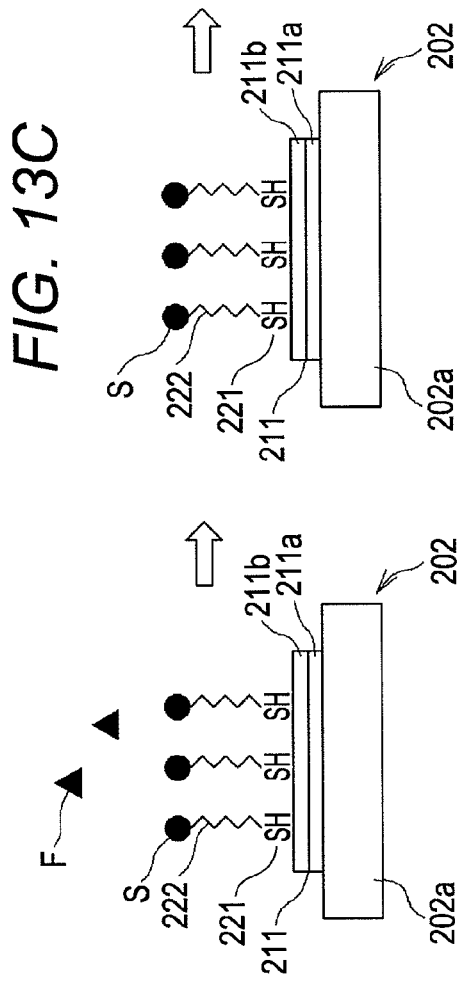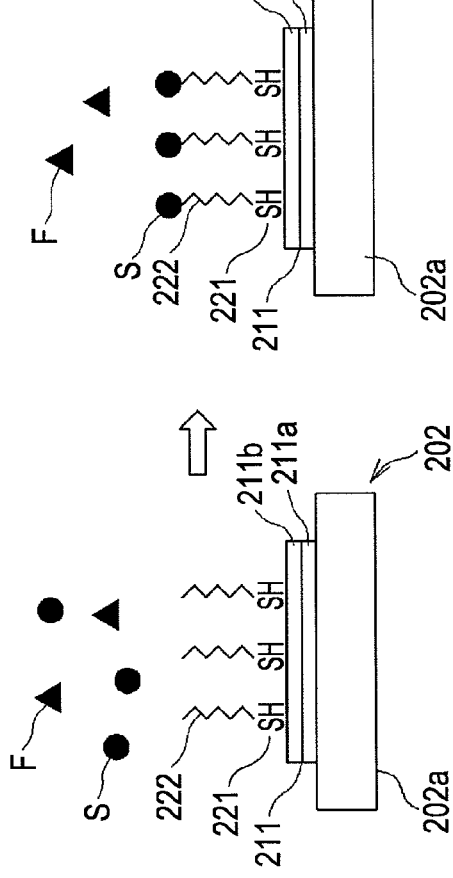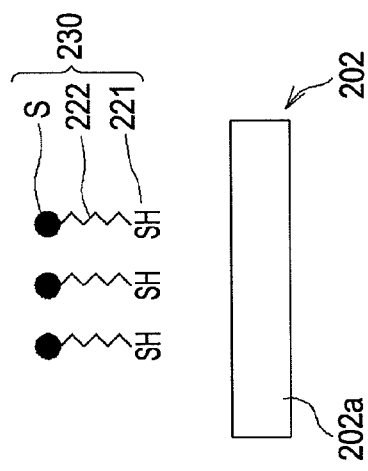

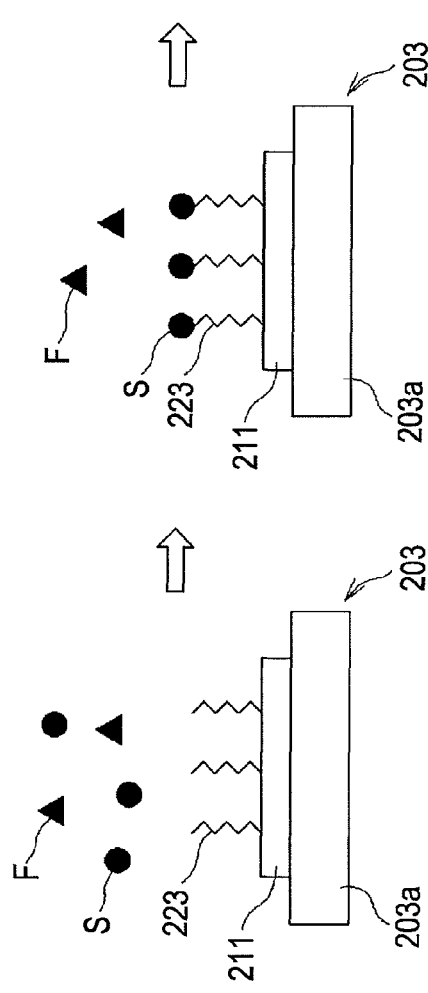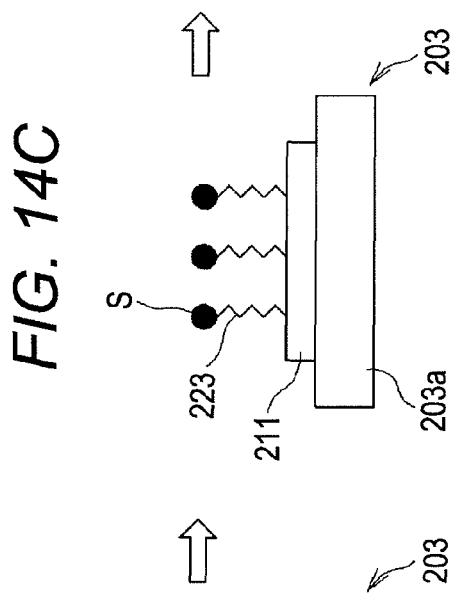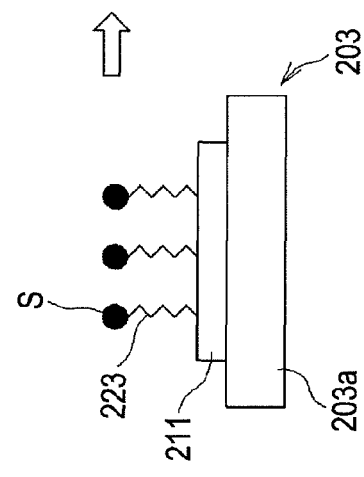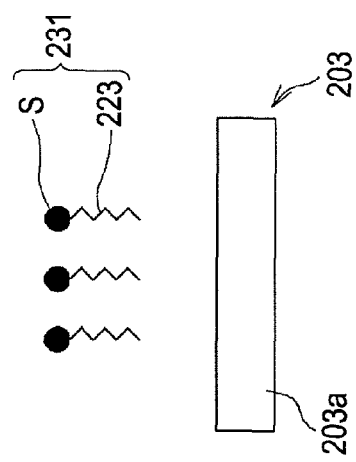

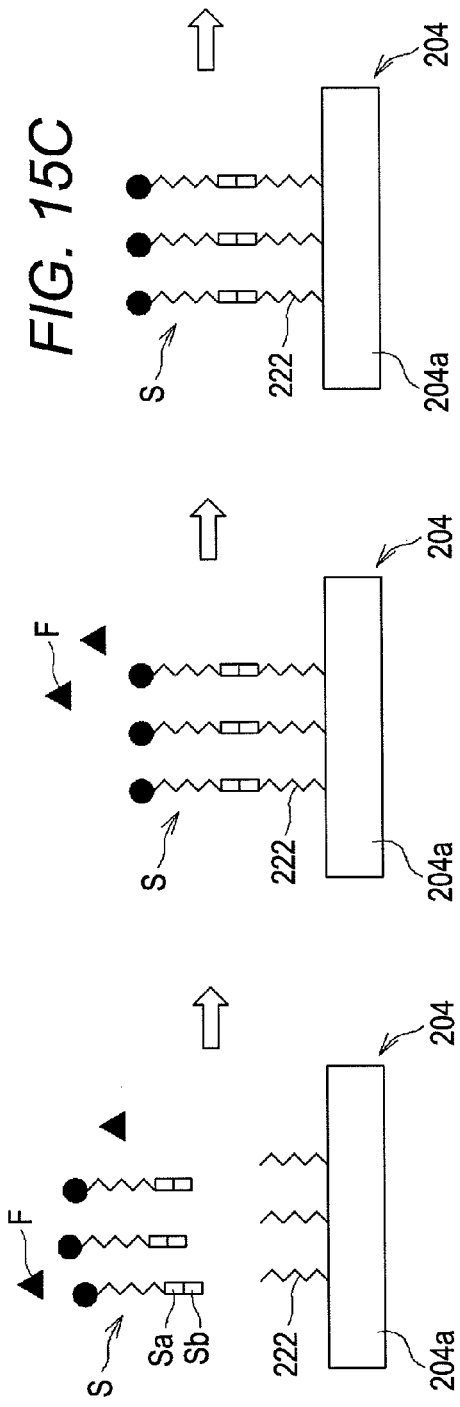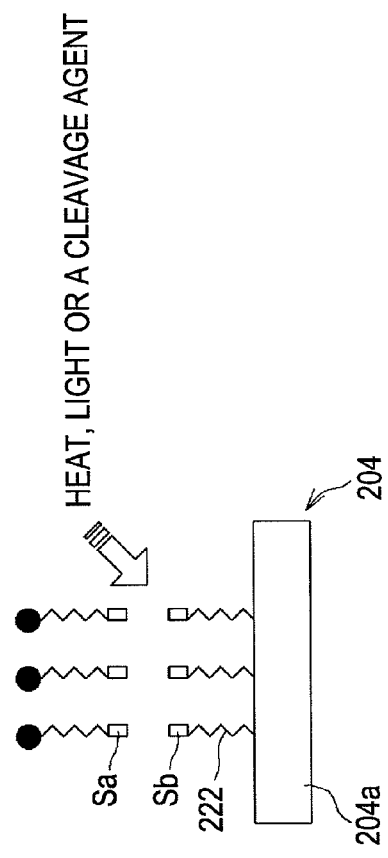

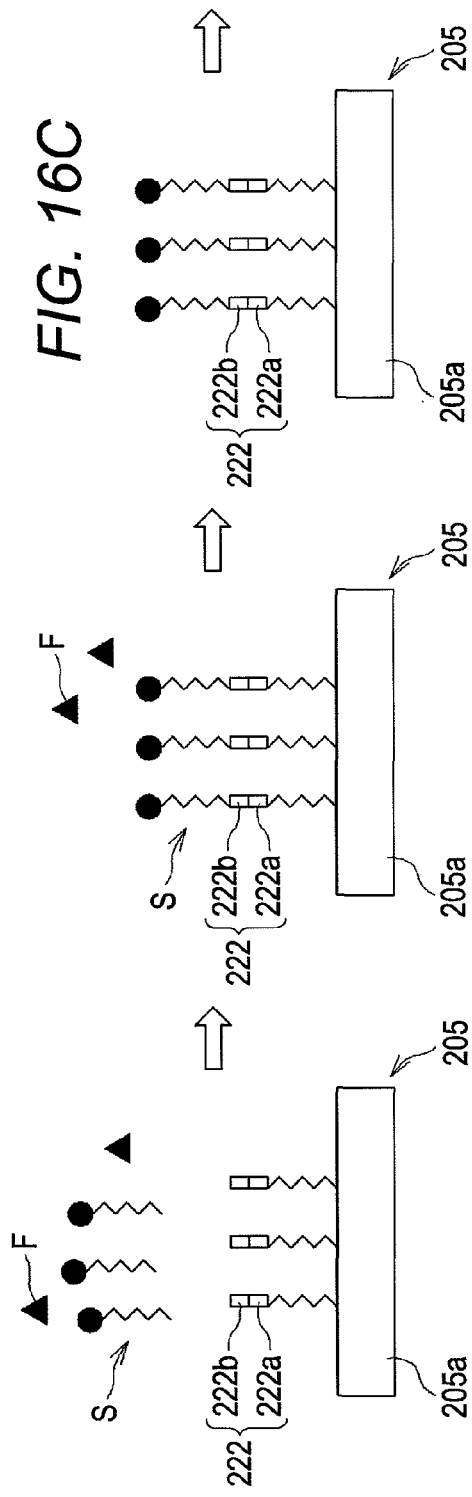

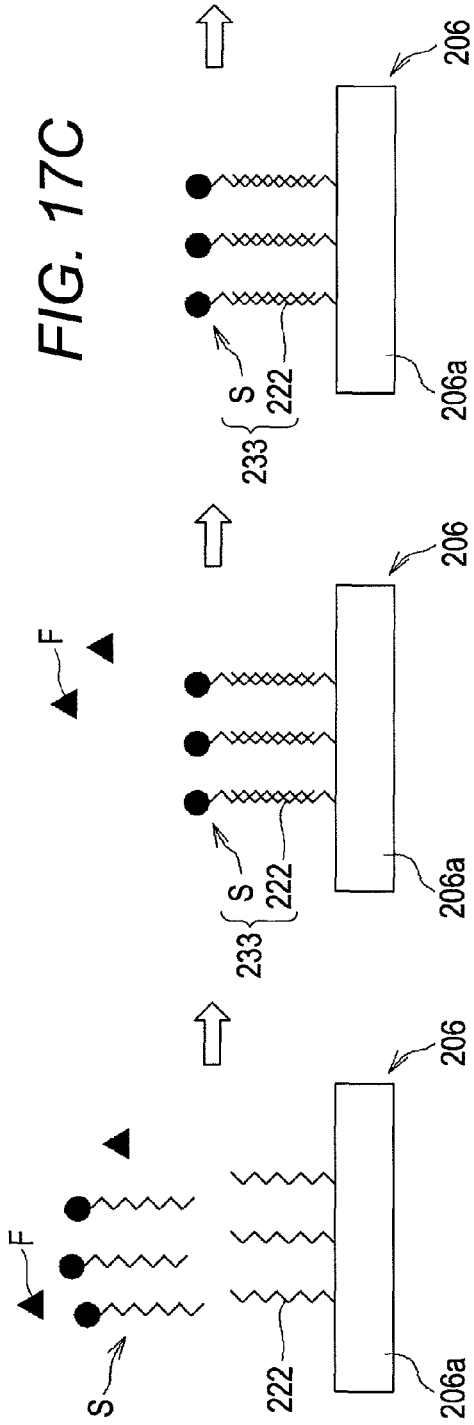

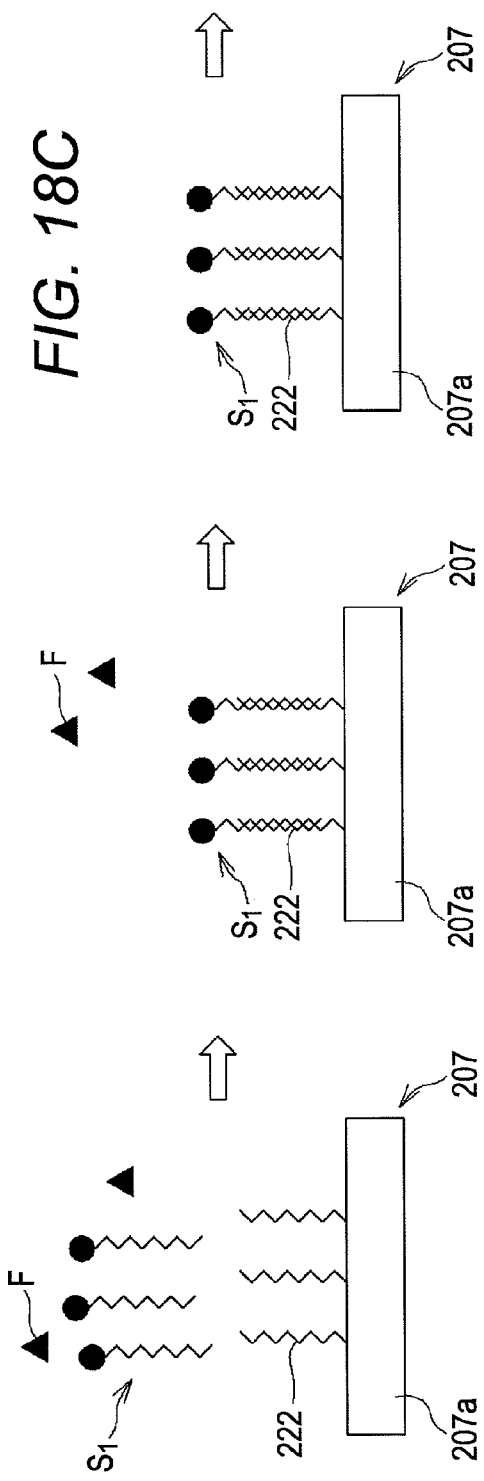

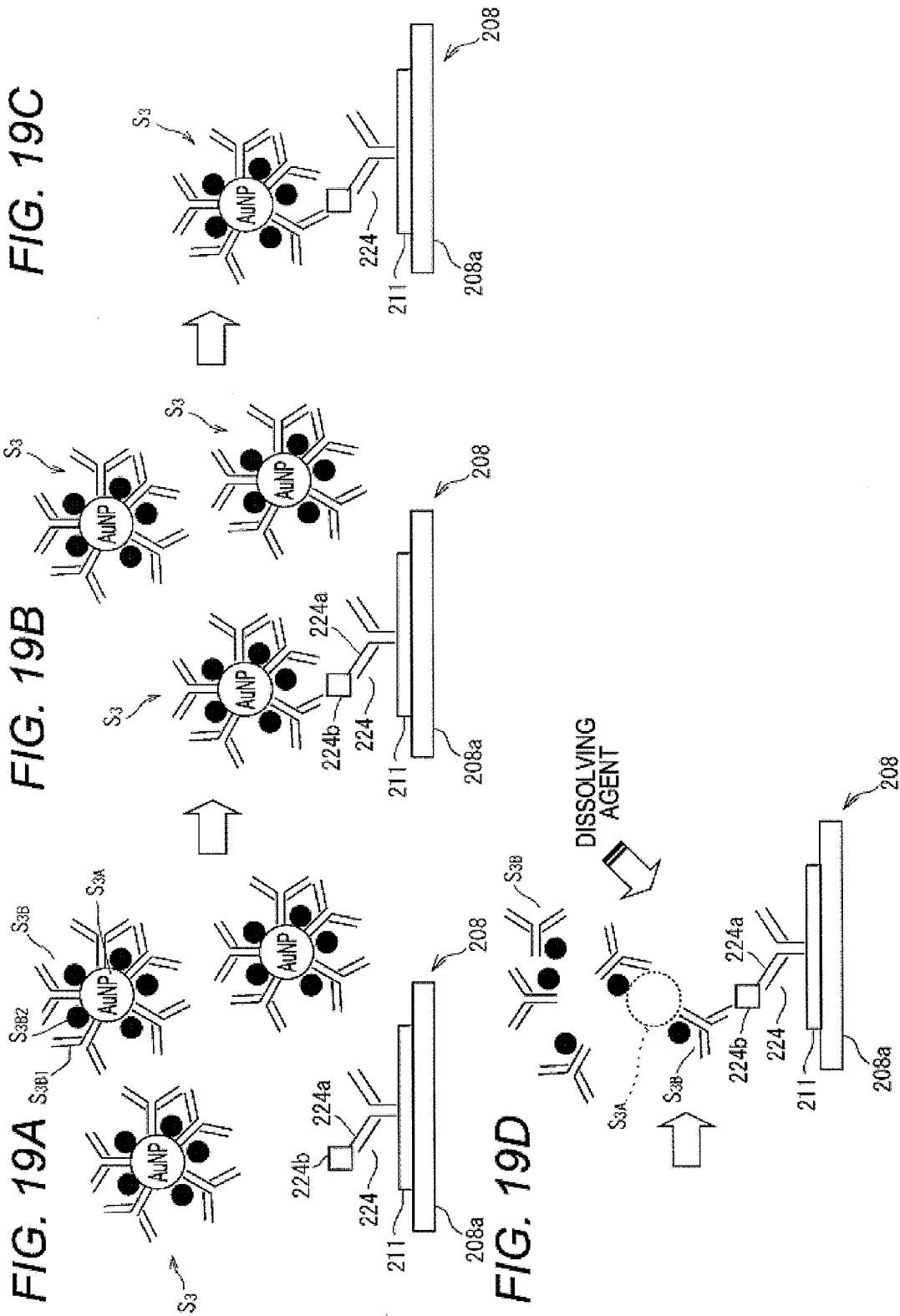

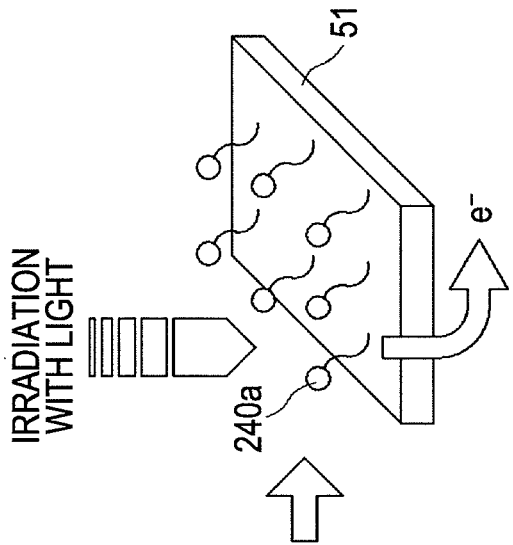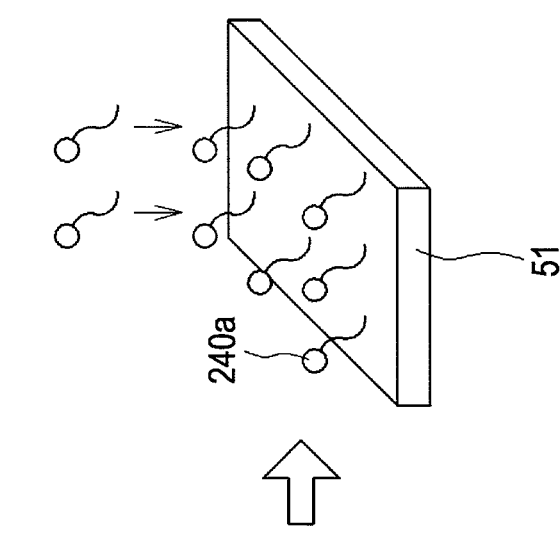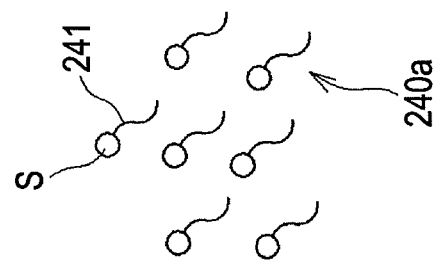

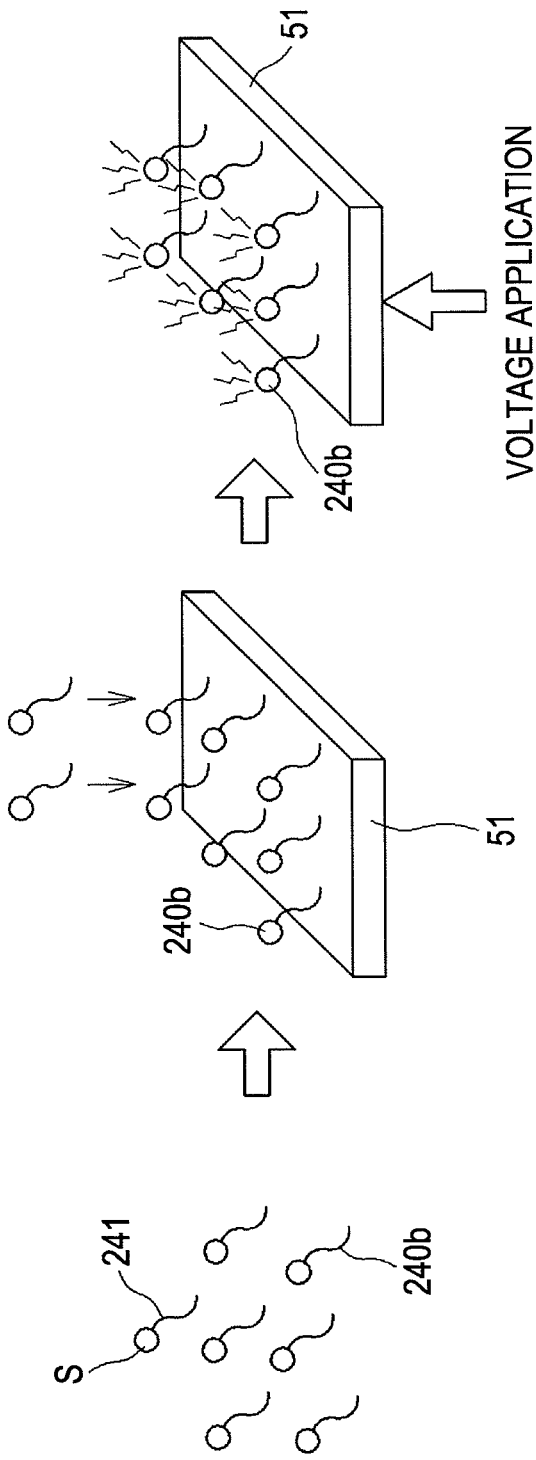

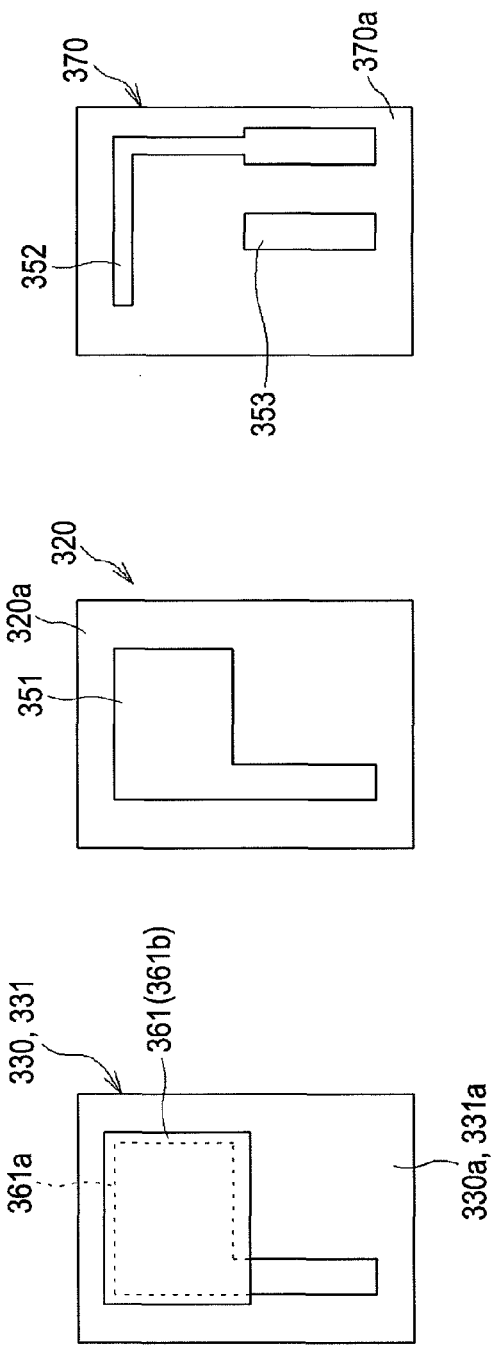
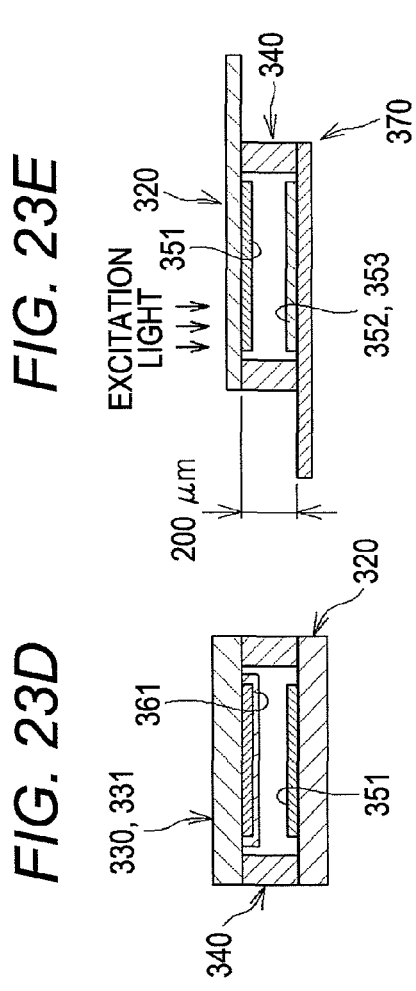

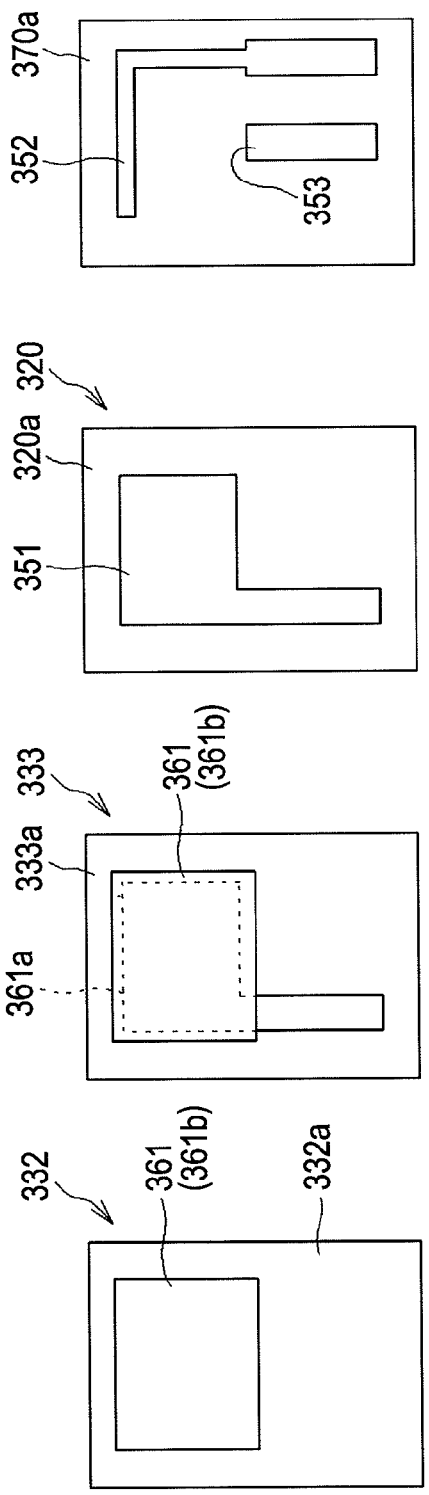
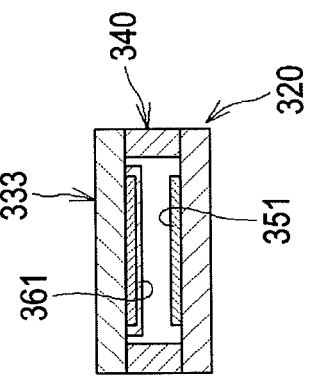
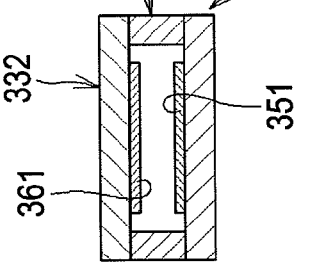

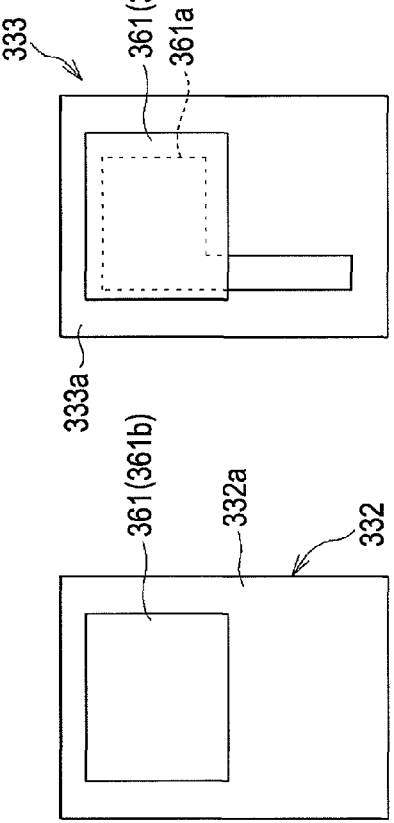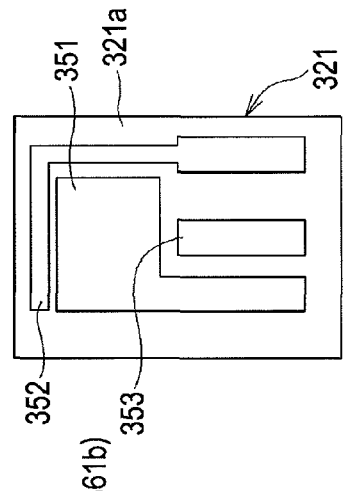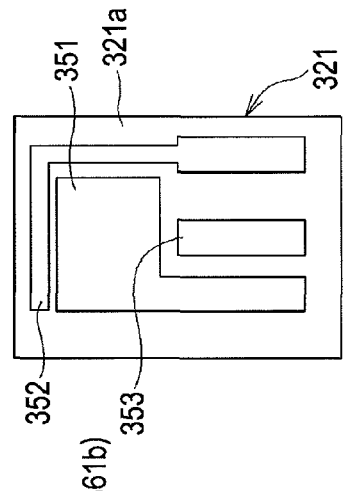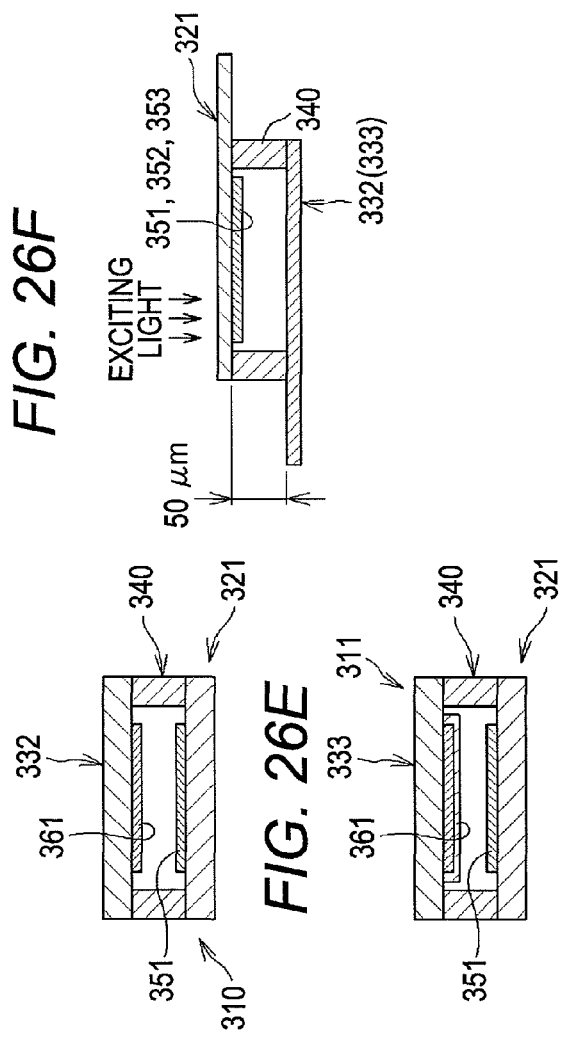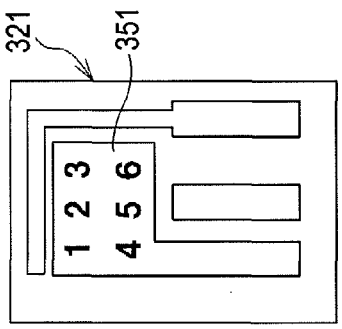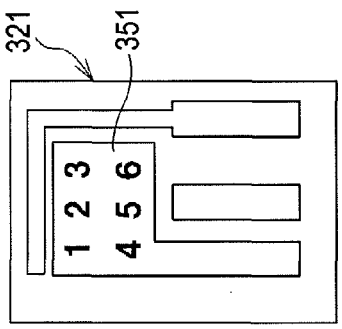

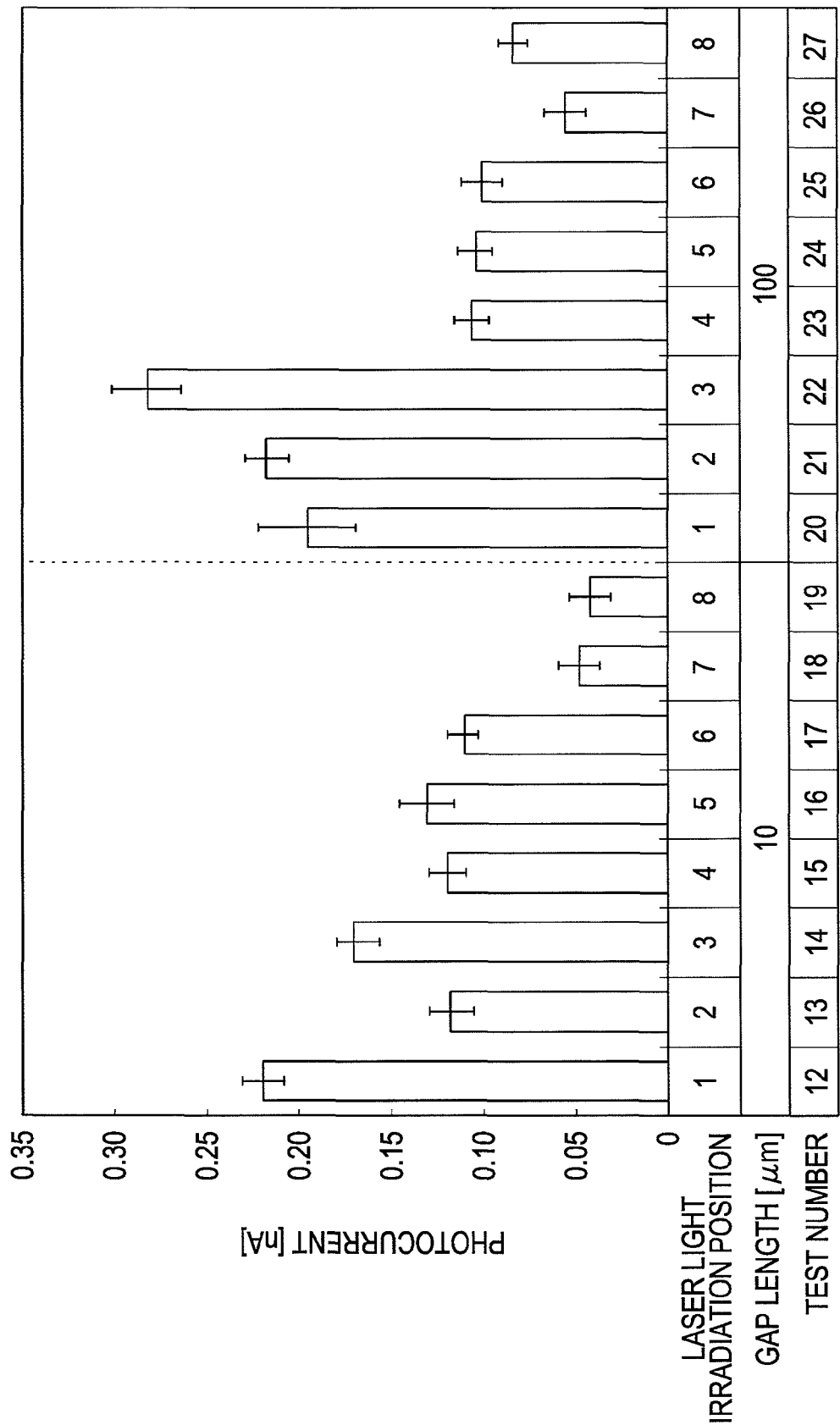

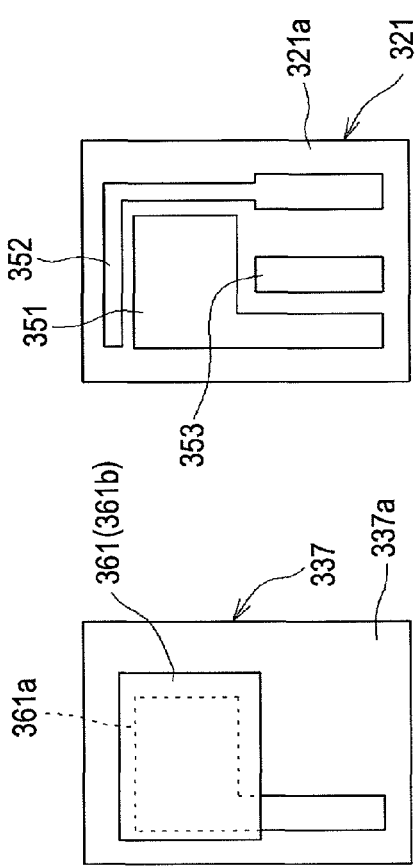
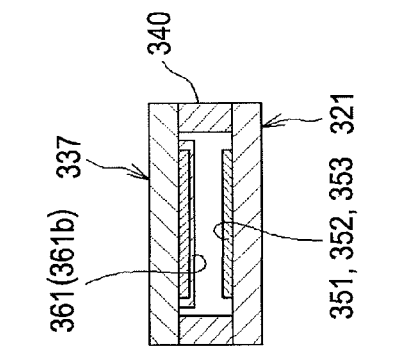
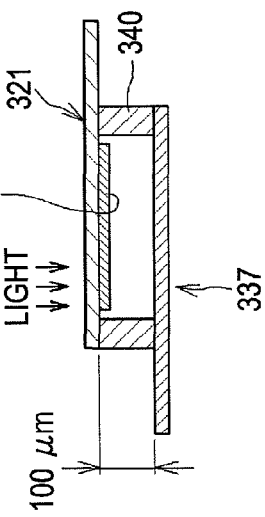
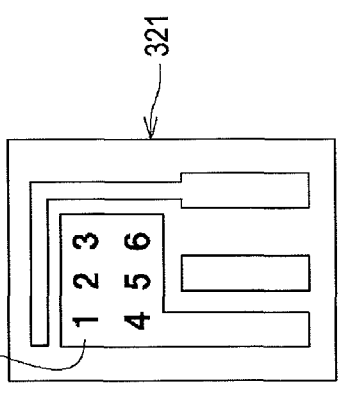
FIG. 34A
FIG. 34B
FIG. 34C
FIG. 34D
FIG. 34E

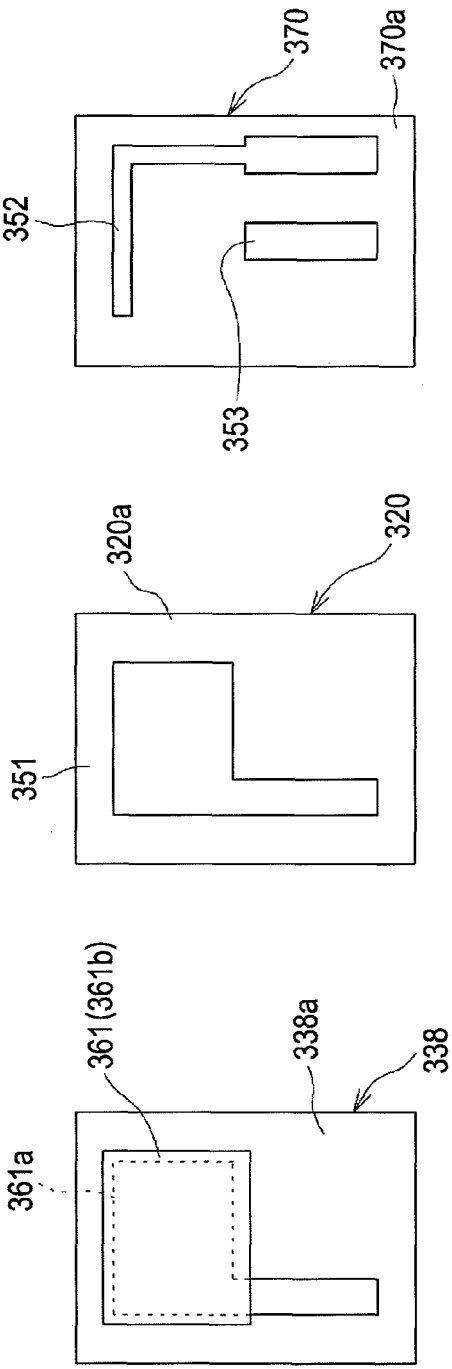

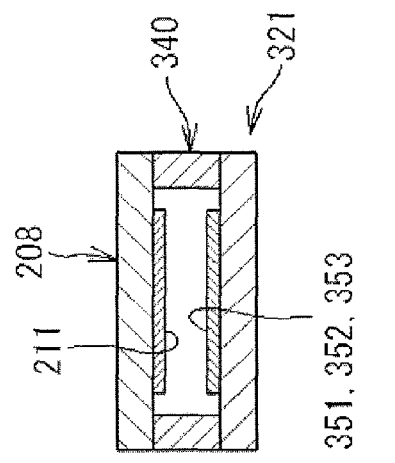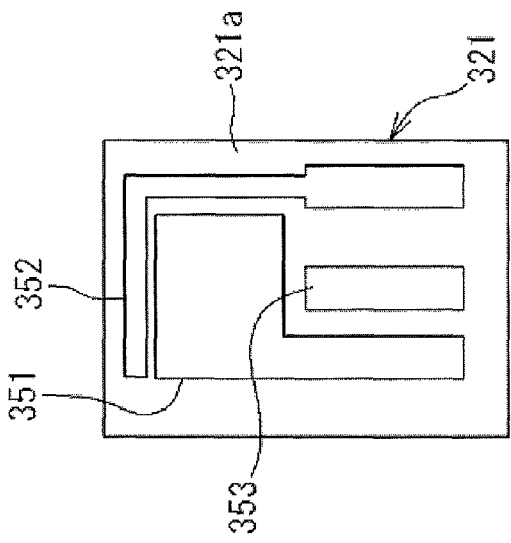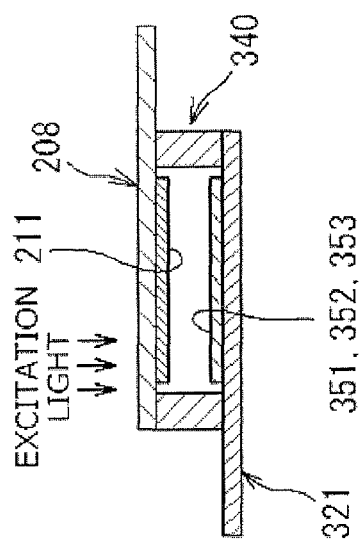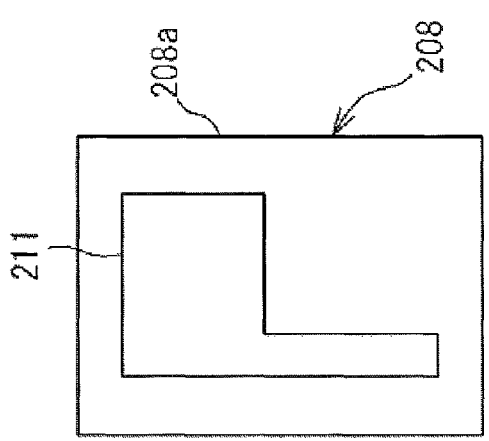

US 9,157,885 B2

METHOD OF ELECTROCHEMICALLY DETECTING TARGET SUBSTANCE, METHOD OF ELECTROCHEMICALLY DETECTING ANALYTE, TEST CHIP, AND DETECTION SET

FIELD OF THE INVENTION

The present invention relates to a method of electrochemically detecting a target substance, a method of electrochemically detecting an analyte, a test chip, and a detection set. More particularly, it relates to a method of electrochemically detecting a target substance, a method of electrochemically detecting an analyte, and a detection set which are useful for detecting and quantifying the analyte as well as clinically examining and diagnosing diseases using these methods.

BACKGROUND

Clinical examination and diagnosis of diseases are performed by detecting genes and proteins related to the diseases which are contained in biological samples by detection methods such as a gene detection method and an immunological detection method. Examples of the detection methods include immunochromatography, latex agglutination, enzyme immunoassay, chemiluminescent immunoassay, and PCR assay, and the like.

However, these detection methods have room for improvement in detectability, quantitative performance, measuring range, and the simplicity and rapidity of operations.

A method of using an electric current generated by photo-excitation of a photochemically active labeling substance and light or an electric current generated by applying a voltage of an electrochemically active labeling substance to detect analytes such as genes and proteins (electrochemical detection method) is proposed for the purpose of improving detection sensitivity, quantitative performance, and simplicity (see, for example, U.S. Patent Publication No. 2009/294305, U.S. Pat. Nos. 5,776,672, 5,972,692, U.S. Patent Publication No. 2010/108539, U.S. Patent Publication No. 2010/112578, and U.S. Patent Publication No. 2003/080284).

U.S. Patent Publication No. 2009/294305 describes a method of detecting an analyte, comprising: irradiating the analyte labeled with a photochemically active sensitizing dye with light; and measuring an electric current caused by photoexcitation of the sensitizing dye contained in the labeled analyte (hereinafter referred to as "photoelectrochemical detection"). In the method described in U.S. Patent Publication No. 2009/294305, the labeled analyte is brought into contact with a working electrode containing a trapping substance capable of binding directly or indirectly to the label analyte on the surface. Thus, the labeled analyte is immobilized on the working electrode through the trapping substance. Subsequently, the working electrode and a counter electrode are brought into contact with an electrolyte medium, and the labeled analyte immobilized on the working electrode is irradiated with light to excite the sensitizing dye. Thereafter, the analyte is specifically detected by measuring a photocurrent which flows between the working electrode and the counter electrode due to electronic transition from the photoexcited sensitizing dye to the working electrode.

U.S. Pat. Nos. 5,776,672 and 5,972,692 disclose gene detection methods using a single-stranded nucleic acid probe having a base sequence complementary to the base sequence of a target gene which is immobilized on an electrode and a double-stranded nucleic acid recognizing substance which specifically binds to double strand nucleic acid and contains a labeling substance which is electrochemically active. In the methods described in U.S. Pat. Nos. 5,776,672 and 5,972,692, a sample containing nucleic acid that is denatured into a single strand, a probe, the double-stranded nucleic acid recognizing substance are contacted with one another. Then, a target gene is detected by measuring an oxidation reduction current or electrochemical luminescence based on the labeling substance contained in the double-stranded recognizing substance bound to a double strand nucleic acid which is formed by hybridization between a nucleic acid corresponding to the target gene and a probe.

Methods of electrochemically detecting an analyte using a test chip which includes a working electrode having a conductive layer and an electron accepting layer, a probe immobilized on the electron accepting layer, a counter electrode, and a reduction electrode are described in U.S. Patent Publication No. 2010/108539 and U.S. Patent Publication No. 2010/112578. In the methods described in Publication No. 2010/108539 and U.S. Patent Publication No. 2010/112578, an electrolytic reduction reaction is facilitated by applying a potential to the reduction electrode of the test chip. Accordingly, the current flowing between the working electrode and the counter electrode is increased and the detectability of analyte is improved.

A method including allowing an analyte labeled with a labeling substance to be trapped by a probe immobilized on a metal layer formed on a semiconductor layer of the working electrode and electrochemically detecting it is described in U.S. Patent Publication No. 2003/080284. In the method described in U.S. Patent Publication No. 2003/080284, the analyte labeled with the labeling substance is first trapped by the probe immobilized on the metal layer formed on the semiconductor layer of the working electrode. Thereafter, the metal layer is dissolved. Then, the photocurrent flowing between the working electrode and the counter electrode is detected.

In these detection methods, the analyte is detected through a labeling substance which is electrochemically or photo-chemically active. Therefore, the working electrode in which a trapping substance for trapping an analyte is immobilized on the surface so that the labeling substance is present near the working electrode according to the amount of the analyte has been used.

However, the methods described in U.S. Patent Publication No. 2009/294305, U.S. Pat. Nos. 5,776,672, 5,972,692, U.S. Patent Publication No. 2010/108539, and U.S. Patent Publication No. 2010/112578 have the following defects.

The first defect is that noise can occur. This is because the trapping and detection regions of the analyte are located in the same region and impurities present in a sample are nonspecifically adsorbed on the working electrode.

The second defect is that when a large-sized analyte is to be detected, the detection capacity can be reduced. This is because it is difficult to make the labeling substance present near the working electrode due to steric interference and the distance between the working electrode and the labeling substance becomes larger.

The third defect is that the reuse of the working electrode with the trapping substance immobilized may be difficult. This is because, in order to reuse the working electrode with the trapping substance immobilized, it is necessary to remove substances other than the trapping substance on the working electrode by a cleaning process. In this case, the trapping substance may also be removed from the working electrode in the cleaning process. Further, the trapping substance on the working electrode may be denatured by a cleaning agent to be used in the cleaning process. Thus, the time of reusing the working electrode with the trapping substance immobilized may affect the measurement results. Therefore, a detection unit which includes the working electrode with the trapping substance immobilized is usually thrown away for each measurement process. Consequently, a detection system using the working electrode with the trapping substance immobilized causes higher costs per measurement.

The second defect is improved by the method described in U.S. Patent Publication No. 2003/080284. However, the first and third defects are remained. As for the method described in U.S. Patent Publication No. 2003/080284, in the process of allowing the analyte to be trapped by the probe, the metal layer may be peeled off depending on conditions.

There is suggested a process of forming an adhesion layer made of titanium, palladium or chromium as an intermediate layer between the working electrode and the metal layer in order to improve the adhesion between the working electrode and the metal layer and prevent the metal layer from being peeled off. However, in this case, the photocurrent generated from the adhesion layer can be noise.

SUMMARY OF THE INVENTION

The scope of the present invention is defined solely by the appended claims, and is not affected to any degree by the statements within this summary.

The present invention has been achieved in view of the above circumstances. There is provided a method for electrochemically detecting a target substance, a method for electrochemically detecting an analyte, a test chip, and a detection set which are capable of well detecting the analyte regardless of the size of the analyte and can reuse the working electrode.

In order to solve the above problems, the present inventors have conducted intensive examinations. As a result, they have found that the problems can be solved by using a probe holding substrate with a probe for a trapping target substance or an analyte held on the substrate body in order to trap the target substance or analyte, and then the present invention has been achieved.

A first aspect of the present invention is a method of electrochemically detecting a target substance containing a labeling substance, comprising:

(1-1) bringing the target substance containing a labeling substance into contact with a probe holding substrate in which a probe for trapping the target substance containing a labeling substance is held on the substrate body and allowing the target substance containing a labeling substance to be trapped by the probe;

(1-2) detaching the labeling substance, the target substance or a moiety which is a part of the target substance and contains a labeling substance from a substrate body of the probe holding substrate obtained in the process (1-1) and attracting to a working electrode in which a trapping substance for trapping the labeling substance, the target substance or the moiety which is a part of the target substance and contains a labeling substance is not present; and (1-3) electrochemically detecting the labeling substance, the target substance or the moiety which is a part of the target substance and contains a labeling substance which has been attracted to the working electrode in the process (1-2).

A second aspect of the present invention is a method of electrochemically detecting an analyte, comprising:

(2-1) bringing an analyte and a label binding substance obtained by labeling a binding substance for trapping the analyte with a labeling substance into contact with a probe holding substrate in which a probe for trapping the analyte or the label binding substance is held on the substrate body to form a complex containing the labeling substance and the analyte on the probe holding substrate;

(2-2) detaching at least the label binding substance or the labeling substance from the holder of the probe holding substrate obtained in the process (2-1) and attracting to a working electrode in which a trapping substance for trapping the label binding substance or the labeling substance is not present; and (2-3) electrochemically detecting the label binding substance or the labeling substance which has been attracted to the working electrode in the process (2-2).

A third aspect of the present invention is a method of electrochemically detecting an electrochemically or photochemically active analyte, comprising:

(3-1) bringing an analyte into contact with a probe holding substrate in which a probe for trapping the analyte is held on the substrate body to allow the analyte to be trapped by the probe;

(3-2) detaching the analyte or a part of the analyte trapped by the probe from the holder of the probe holding substrate in the process (3-1) and attracting to a working electrode in which a trapping substance for trapping the analyte or the part of the analyte is not present; and (3-3) electrochemically detecting the analyte or the part of the analyte which has been attracted to the working electrode in the process (3-2).

A fourth aspect of the present invention is a test chip, comprising:

an electrode substrate including a working electrode;

a counter electrode; and a probe holding substrate which has a probe for trapping an analyte or a label binding substance obtained by labeling a binding substance for trapping the analyte with a labeling substance on a substrate body;

wherein the electrode substrate including the working electrode and the probe holding substrate are arranged so as to be opposed to each other through a predetermined gap.

A fifth aspect of the present invention is a detection set for electrochemically detecting an analyte, comprising:

a label binding substance obtained by labeling a binding substance for trapping the analyte with a labeling substance;

a probe holding substrate in which a probe for trapping the analyte or the label binding substance is held on the substrate body;

an electrode substrate including a working electrode in which a trapping substance for trapping the label binding substance or the labeling substance is not present and a counter electrode; and a spacer which allows a predetermined gap to be formed between the probe holding substrate and the electrode substrate.

A sixth aspect of the present invention is a detection set for electrochemically detecting an analyte, comprising:

a label binding substance obtained by labeling a binding substance for trapping the analyte with a labeling substance;

a probe holding substrate in which a probe for trapping the analyte or the label binding substance is held on a substrate body and a counter electrode is formed on the substrate body;

an electrode substrate including a working electrode in which a trapping substance for trapping the label binding substance or the labeling substance is not present; and a spacer which allows a predetermined gap to be formed between the probe holding substrate and the electrode substrate.

According to the method for electrochemically detecting a target substance, the method for electrochemically detecting an analyte, the test chip, and the detection set in the present invention, the analyte can be well detected regardless of the size of the analyte and the working electrode can be reused.

BRIEF DESCRIPTION OF THE DRAWINGS

FIG. 3 (B) is a cross sectional explanatory view in an AA line of the test chip shown in FIG. 3 (A);

FIG. 3 (C) is a plane explanatory view of a probe holding substrate included in the test chip shown in FIG. 3 (A);

FIG. 3 (D) is a plane explanatory view of an electrode substrate included in the test chip shown in FIG. 3 (A);

FIG. 5 (B) is a cross sectional explanatory view in a BB line of the test chip shown in FIG. 5 (A);

FIG. 5 (C) is a plane explanatory view of the probe holding substrate included in the test chip shown in FIG. 5 (A);

FIG. 5 (D) is a plane explanatory view of the electrode substrate included in the test chip shown in FIG. 5 (A);

FIG. 6 (B) is a cross sectional explanatory view in a CC line of the test chip shown in FIG. 6 (A);

FIG. 6 (C) is a plane explanatory view of the probe holding substrate included in the test chip shown in FIG. 6 (A);

FIG. 6 (D) is a plane explanatory view of the electrode substrate included in the test chip shown in FIG. 6 (A);

FIG. 7 (A) is a plane explanatory view showing the modification of the test chip shown in FIG. 3;

FIG. 7 (B) is a cross sectional explanatory view in a DD line of the test chip shown in FIG. 7 (A);

FIG. 7 (C) is a plane explanatory view of the probe holding substrate included in the test chip shown in FIG. 7 (A);

FIG. 7 (D) is a plane explanatory view of the electrode substrate included in the test chip shown in FIG. 7 (A);

FIG. 8 (B) is a cross sectional explanatory view in an EE line of the test chip shown in FIG. 8 (A);

FIG. 8 (C) is a plane explanatory view of the probe holding substrate included in the test chip shown in FIG. 8 (A);

FIG. 8 (D) is a plane explanatory view of the electrode substrate included in the test chip shown in FIG. 8 (A);

FIG. 8 (E) is a perspective explanatory view of a spacer;

FIG. 9 (A) is a plane explanatory view showing the modification of the test chip shown in FIG. 3;

FIG. 9 (B) is a cross sectional explanatory view in an FF line of the test chip shown in FIG. 9 (A);

FIG. 9 (C) is a plane explanatory view of the probe holding substrate included in the test chip shown in FIG. 9 (A);

FIG. 9 (D) is a plane explanatory view of the electrode substrate included in the test chip shown in FIG. 9 (A);

FIG. 9 (E) is a perspective explanatory view of the spacer;

FIG. 10 (A) is a plane explanatory view showing the modification of the test chip shown in FIG. 3;

FIG. 10 (B) is a cross sectional explanatory view in a GG line of the test chip shown in FIG. 10 (A);

FIG. 10 (C) is a plane explanatory view of the probe holding substrate included in the test chip shown in FIG. 10 (A);

FIG. 10 (D) is a plane explanatory view of the electrode substrate included in the test chip shown in FIG. 10 (A);

FIG. 10 (E) is a perspective explanatory view of the spacer;

FIG. 12 is a process explanatory view showing the procedure from a process of trapping a target substance to a process of detaching the target substance among the processes of the method for electrochemically detecting a target substance according to one embodiment of the present invention;

FIG. 13 is a process explanatory view showing the procedure from a process of trapping a target substance to a process of detaching the target substance among the processes of the method for electrochemically detecting a target substance according to another embodiment of the present invention;

FIG. 14 is a process explanatory view showing the procedure from a process of trapping a target substance to a process of detaching the target substance among the processes of the method for electrochemically detecting a target substance according to another embodiment of the present invention;

FIG. 15 is a process explanatory view showing the procedure from a process of trapping a target substance to a process of detaching the target substance among the processes of the method for electrochemically detecting a target substance according to another embodiment of the present invention;

FIG. 16 is a process explanatory view showing the procedure from a process of trapping a target substance to a process of detaching the target substance among the processes of the method for electrochemically detecting a target substance according to another embodiment of the present invention;

FIG. 17 is a process explanatory view showing the procedure from a process of trapping a target substance to a process of detaching the target substance among the processes of the method for electrochemically detecting a target substance according to another embodiment of the present invention;

FIG. 18 is a process explanatory view showing the procedure from a process of trapping a target substance to a process of detaching the target substance among the processes of the method for electrochemically detecting a target substance according to another embodiment of the present invention;

FIG. 19 is a process explanatory view showing the procedure from a process of trapping a target substance to a process of detaching the target substance when the target substance containing a labeling substance that has the material for detachably holding the moiety containing a labeling substance is used, among the processes of the method for electrochemically detecting a target substance according to another embodiment of the present invention;

FIG. 20 is a process explanatory view showing the procedure from a process of attracting a target substances to a process of detecting the target substance among the processes of the method for electrochemically detecting a target substance according to one embodiment of the present invention;

FIG. 21 is a process explanatory view showing the procedure from a process of attracting a target substance to a process of detecting the target substance among the processes of the method for electrochemically detecting the target substance according to another embodiment of the present invention;

FIG. 23 (A) is a plane explanatory view showing a DNA holding substrate used in Test example 1;

FIG. 23 (B) is a plane explanatory view showing a working electrode substrate used in Test example 1;

FIG. 23 (C) shows a counter electrode substrate used in Test example 1;

FIG. 23 (D) is a cross sectional explanatory view showing a state of arrangement of the DNA holding substrate and the working electrode substrate when performing the detaching process and the attracting process in Test example 1;

FIG. 23 (E) is a cross sectional explanatory view showing a state of arrangement of the working electrode substrate and the counter electrode substrate when performing the detecting process in Test example 1;

FIG. 23 (F) is a plane explanatory view showing the laser light irradiation position on the working electrode of the working electrode substrate in Test example 1;

FIG. 25 (A) is a plane explanatory view showing the DNA holding substrate used in Test example 2;

FIG. 25 (B) is a plane explanatory view showing another DNA holding substrate used in Test example 2;

FIG. 25 (C) is a plane explanatory view showing the working electrode substrate used in Test example 2;

FIG. 25 (D) is a plane explanatory view showing the counter electrode substrate used in Test example 2;

FIG. 25 (E) is a cross sectional explanatory view showing a state of arrangement of the DNA holding substrate and the working electrode substrate when performing the detaching process and the attracting process in Test example 2;

FIG. 25 (F) is a cross sectional explanatory view showing a state of arrangement of the DNA holding substrate and the working electrode substrate when performing the detaching process and the attracting process in Test example 2;

FIG. 26 (A) is a plane explanatory view showing the DNA holding substrate used in Test example 3;

FIG. 26 (B) is a plane explanatory view showing another DNA holding substrates used in Test example 3;

FIG. 26 (C) is a plane explanatory view showing the electrode substrate used in Test example 3;

FIG. 26 (D) is a cross sectional explanatory view showing a state of arrangement of the test chip when performing the detaching process and the attracting process in Test example 3;

FIG. 26 (E) is a cross sectional explanatory view showing a state of arrangement of the test chip when performing the detaching process and the attracting process in Test example 3;

FIG. 26 (F) is a cross sectional explanatory view showing a state of arrangement of the test chip when performing the detecting process in Test example 3;

FIG. 26 (G) is a plane explanatory view showing the laser light irradiation position on the working electrode of the electrode substrate in Test example 3;

FIG. 28 (B) is a plane explanatory view showing the working electrode substrate used in Test example 4;

FIG. 28 (C) is a plane explanatory view showing the counter electrode substrate used in Test example 4;

FIG. 28 (D) is a cross sectional explanatory view showing a state of arrangement of the DNA holding substrate and the working electrode substrate when performing the detaching process and the attracting process in Test example 4;

FIG. 28 (E) is a plane explanatory view showing the laser light irradiation position on the working electrode of the working electrode substrate in Test example 4;

FIG. 30 (B) is a plane explanatory view showing a DNA holding position and a DNA non-holding position on a holder of the DNA holding substrate in Test example 5;

FIG. 30 (C) is a plane explanatory view showing the electrode substrate used in Test example 5;

FIG. 30 (D) is a cross sectional explanatory view showing a state of arrangement of the test chip when performing the detaching process and the attracting process in Test example 5;

FIG. 30 (E) is a cross sectional explanatory view showing a state of arrangement of the test chip when performing the detecting process in Test example 5;

FIG. 30 (F) is a plane explanatory view showing the laser light irradiation position on the working electrode of the electrode substrate in Test example 5;

FIG. 31 is a graph showing examined results of a relationship among gap length, light irradiation position, and photocurrent in Test example 5;

FIG. 32 (B) is a plane explanatory view showing a DNA holding position and a DNA non-holding position on a holder of the DNA holding substrate in Test example 6;

FIG. 32 (C) is a plane explanatory view showing the electrode substrate used in Test example 6;

FIG. 32 (D) is a cross sectional explanatory view showing a state of arrangement of the test chip when performing the detaching process and the attracting process in Test example 6;

FIG. 32 (E) is a cross sectional explanatory view showing a state of arrangement of the test chip when performing the detecting process in Test example 6;

FIG. 32 (F) is a plane explanatory view showing the laser light irradiation position on the working electrode of the electrode substrate in Test example 6;

FIG. 34 (A) is a plane explanatory view showing the DNA holding substrate used in Example 1;

FIG. 34 (B) is a plane explanatory view showing the electrode substrate used in Example 1;

FIG. 34 (C) is a cross sectional explanatory view showing a state of arrangement of the test chip when performing the detaching process and the attracting process in Example 1;

FIG. 34 (D) is a cross sectional explanatory view showing a state of arrangement of the test chip when performing the detecting process in Example 1;

FIG. 34 (E) is a plane explanatory view showing the laser light irradiation position on the working electrode of the electrode substrate in Example 1;

FIG. 36 (A) is a plane explanatory view showing the DNA holding substrate used in Example 2;

FIG. 36 (B) is a plane explanatory view showing the working electrode substrate used in Example 2;

FIG. 36 (C) is a plane explanatory view showing the counter electrode substrate used in Example 2;

FIG. 36 (D) is a cross sectional explanatory view showing a state of arrangement of the DNA holding substrate and the working electrode substrate when performing the detaching process and the attracting process in Example 2;

FIG. 36 (E) is a cross sectional explanatory view showing a state of arrangement of the working electrode substrate and the counter electrode substrate when performing the detecting process in Example 2;

FIG. 36 (F) is a plane explanatory view showing the laser light irradiation position on the working electrode of the working electrode substrate in Example 2;

FIG. 37 (B) is a graph showing results obtained by correcting the graph shown in (A) in Example 2;

FIG. 38 (B) is a plane explanatory view showing the working electrode substrate and the laser light irradiation position on the working electrode of the working electrode substrate used in Example 3;

FIG. 38 (C) is a cross sectional explanatory view showing a state of arrangement of the working electrode substrate and the counter electrode substrate when performing the detecting process in Example 3;

FIG. 41 (A) is a plane explanatory view showing the probe holding substrate used in Example 4;

FIG. 41 (B) is a plane explanatory view showing the electrode substrate used in Example 4;

FIG. 41 (C) is a cross sectional explanatory view showing a state of arrangement of the probe holding substrate and the electrode substrate when performing the detaching process and the attracting process in Example 4; and FIG. 41 (D) is a cross sectional explanatory view showing a state of arrangement of the working electrode substrate and the counter electrode substrate when performing the detecting process in Example 4.

DETAILED DESCRIPTION OF THE PREFERRED EMBODIMENTS

The preferred embodiments of the present invention will be described hereinafter with reference to the drawings.

[Term Definition]

The terms "target substance containing a labeling substance" and "target substance" used herein mean a substance to be electrochemically detected on the working electrode and the labeling substance is included. The target substance used herein may be a complex obtained by allowing the labeling substance to be directly bound to the analyte. The target substance may be a complex obtained by trapping the analyte on a solid phase and binding the labeling substance to the substance allowed to be present according to the amount of the trapped analyte. Here, the solid phase means, for example, substrates formed of inorganic materials such as glass and metal; and plastics such as polyethylene terephthalate and polyimide resin or substrates including at least one of these materials; tubes; fibers; membranes; nanostructures (e.g. silica-based nanostructure such as mesoporous silica, and porous alumina); and; particles such as glass beads, magnetic beads, metal particles, and plastic beads or particles including at least one of them.

The term "attractive modulator" used herein means a substance for attracting the target substance and the labeling substance to near the working electrode.

The term "trapping substance is not present" used herein means that "the trapping substance is not substantially present". That is, a concept of the term "trapping substance is not present" includes a concept that a small amount of the trapping substance is present on the working electrode so as not to contribute to substantial trapping of an objective substance.

[Configuration of Detector]

An example of the detector to be used for the method of electrochemically detecting a target substance which contains the labeling substance of the present invention and the method of electrochemically detecting an analyte will be first explained with reference to the accompanying drawings.

Figure 1:
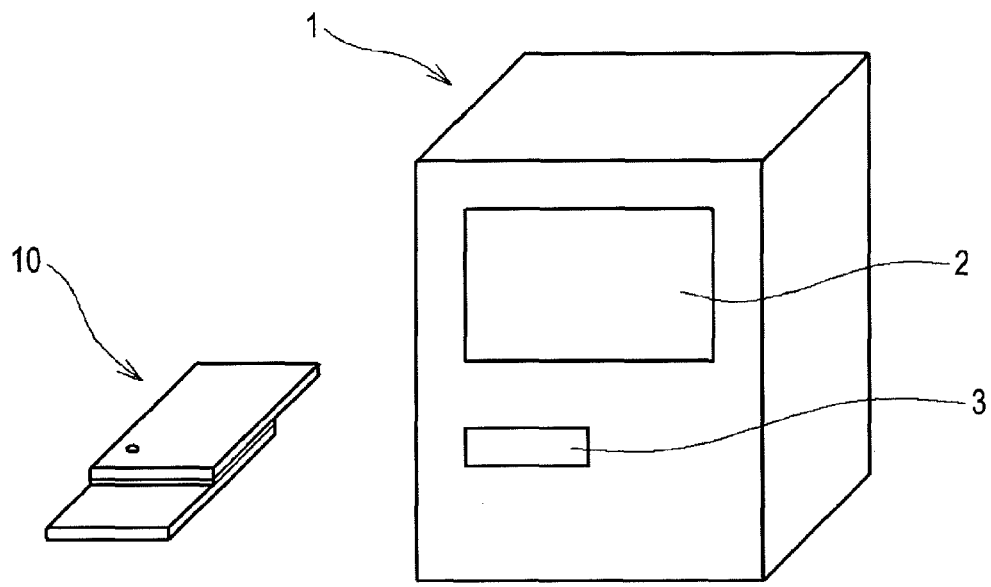
FIG. 1 is a perspective explanatory view showing a detector which is used for the method for electrochemically detecting a target substance and the method for electrochemically detecting an analyte according to one embodiment of the present invention.

FIG. 1 is a perspective explanatory view showing a detector which is used for the method for electrochemically detecting a target substance and the method for electrochemically detecting an analyte according to one embodiment of the present invention. A detector 1 is used for the electrochemical detection method which photoelectrochemically detects the target substance which contains the labeling substance using a photochemically active substance as a labeling substance.

The detector 1 includes a chip insertion unit 3 into which a test chip 10 is inserted and a display 2 which displays the detection results.

Figure 2:
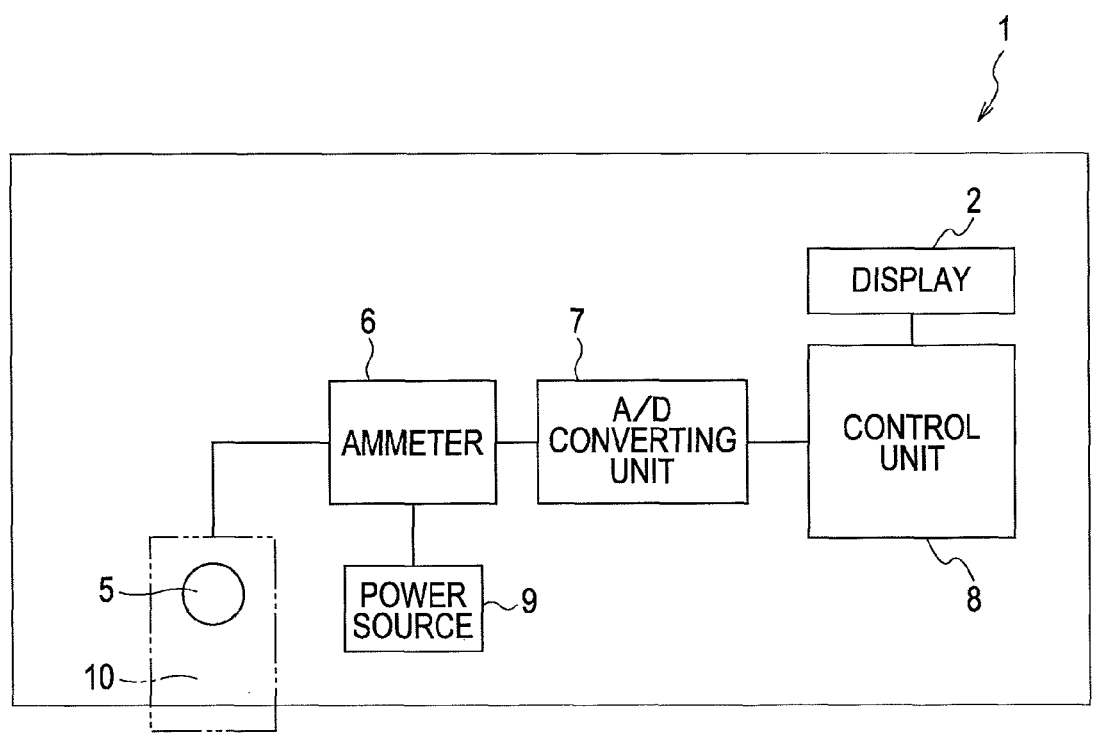
FIG. 2 is a block diagram showing the configuration of the detector shown in FIG. 1.
Figure 3A:
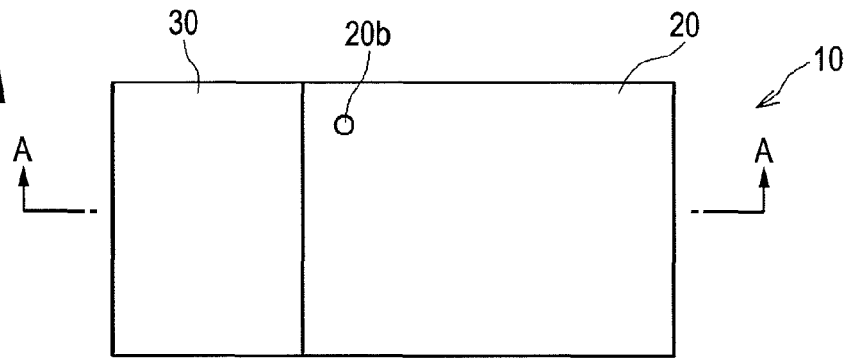
FIG. 3 (A) is a plane explanatory view showing the test chip according to one embodiment of the present invention.
Figure 3B:
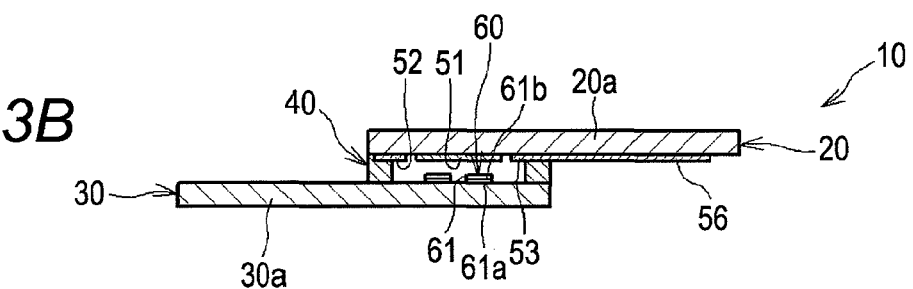
Figure 3C:
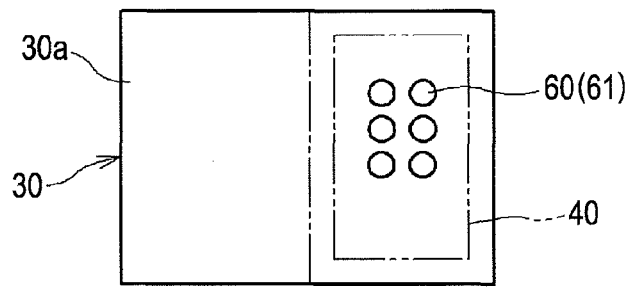
Figure 3D:
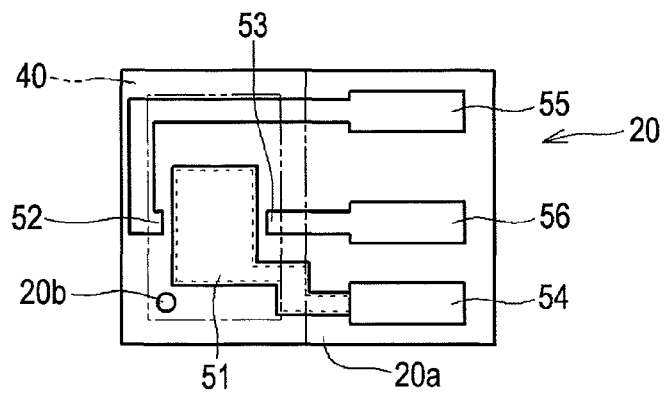

FIG. 2 is a block diagram showing the configuration of the detector shown in FIG. 1. The detector 1 includes a light source 5, an ammeter (current measuring unit) 6, a power source (potential applying unit) 9, an A/D converting unit 7, a control unit 8, and a display 2.

The light source 5 irradiates the target substance containing a labeling substance which has been transported to near the working electrode of the test chip 10 with light to excite the labeling substance. The ammeter 6 measures an electric current which flows through the test chip 10 due to electrons released from the excited labeling substance. The power source 9 applies a predetermined potential to an electrode formed in the test chip 4. The A/D converting unit 7 digitally converts the current values measured by the ammeter 6. The control unit 8 is configured to include a CPU, a ROM, and a RAM and controls the operation of the light source 5, the ammeter 6, the power source 9, and the display 2. The control unit 8 estimates the amount of the target substance containing a labeling substance based on a calibration curve indicating a relationship between a current value in which the current value digitally converted by the A/D converting unit 7 is created in advance and the amount of the target substance. The display 2 displays the amount of the target substance containing a labeling substance which has been estimated by the control unit 8.

In the present invention, when the target substance containing a labeling substance is detected according to the oxidation reduction current/electrochemiluminescence detection method to be described later, the detector may not include the light source 5 (not shown).

When the target substance containing a labeling substance is detected by electrochemical luminescence, the detector may further include a sensor for detecting light generated from the labeling substance.

In place of the test chip, the detection set to be described later can also be used for the detector.

[Configuration of Test Chip]

Next, the configuration of the test chip which is used for the method of electrochemically detecting a target substance containing a labeling substance and the method of electrochemically detecting an analyte according to the present invention will be described.

1. Test Chip According to First Embodiment (1) Configuration of Test Chip

FIG. 3 (A) is a plane explanatory view showing the test chip 10 according to one embodiment of the present invention. FIG. 3 (B) is a cross sectional explanatory view in an AA line of the test chip 10 shown in FIG. 3 (A).

The test chip 10 includes an electrode substrate 20, a probe holding substrate 30 formed on the lower side of the electrode substrate 20, and a spacer 40 which is inserted between the electrode substrate 20 and the probe holding substrate 30. A sample inlet 20b for injecting a sample containing the target substance or analyte into the inside is formed at the side of the electrode substrate 20 of the test chip 10.

In the test chip 10, electrode sections of the electrode substrate 20 (a working electrode 51, a counter electrode 52, and a reference electrode 53) and a holder 61 of the probe holding substrate 30 are arranged so as to be overlapped at one side portion in such a manner that the formed electrode sections and the holder are vertically opposed. The spacer 40 lies in a portion where the electrode substrate 20 and the probe holding substrate 30 are overlapped (opposed). An electrode lead (an electrode lead 56 and the like) formed on the electrode substrate 20 is extruded from the portion where the electrode substrate 20 and the probe holding substrate 30 are overlapped and is exposed to the outside.

(2) Configuration of Probe Holding Substrate

Next, the configuration of the probe holding substrate 30 included in the test chip 10 will be described.

FIG. 3 (C) is a plane explanatory view of the probe holding substrate 30 included in the test chip 10 shown in FIG. 3 (A).

The probe holding substrate 30 includes a substrate body 30a, a probe 60 for trapping a target substance or analyte, and the holder 61 for holding the probe 60.

The substrate body 30a is formed into a rectangular shape. The shape of the substrate body 30a is not particularly limited and it may be polygonal, discoid, or the like. From the viewpoint of the production and easy handling of the substrate, it is preferably rectangular.

The probe 60 is detachably held on the holder 61.

Six of the holders 61 are formed at six positions on the surface of the substrate body 30a. The holder 61 is composed of a holding layer 61b which detachably holds the probe and an adhesion layer 61a which makes the holding layer 61b stick to the substrate body 30a.

The material for forming the substrate body 30a is not particularly limited and examples thereof include inorganic materials such as glass and metal; and plastics such as polyethylene terephthalate and polyimide resin. Among them, glass is preferred from the viewpoint of ensuring light transmission properties, sufficient heat resistance, durability, and smoothness and reducing costs required for the materials.

The thickness of the substrate body 30a is preferably from 0.01 to 1 mm, more preferably from 0.1 to 0.7 mm, still more preferably about 0.5 mm from the viewpoint of ensuring sufficient durability.

The size of the substrate body 30a is usually about 20 mm×20 mm and it varies depending on the number of items on the premise of detection of various types of the target substances or analytes (many items).

The probe 60 may be a probe capable of trapping the target substance or analyte. Examples of the probe 60 include nucleic acids, proteins, peptides, sugar chains, nanostructures with specific recognition ability.

A probe obtained by binding an antibody to the probe holding substrate 30 and further binding an antigen specifically reacting with the antibody thereto can be as the probe 60. In this case, the probe 60 can trap the antibody specifically reacting with the antigen as the target substance or analyte.

It is preferable that the amount of the probe 60 in the probe holding substrate 30 is suitably set depending on the use and purpose.

The material for forming the holding layer 61b of the holder 61 may be one which detachably holds the probe. The material is not particularly limited. Examples thereof include a metal or alloy which is dissolved in a solution to be described later, a metal or alloy which can be electrolyzed (ionized by oxidation reduction reactions), a compound having a functional group forming a bond which is cleaved by a cleavage agent, a compound having a functional group which is cleaved by the cleavage agent, a compound melted by heating, a compound having a photocleavable functional group, and a compound having a functional group which forms a photocleavable bond.

Examples of the metal or alloy to be dissolved in the solution include gold, platinum, silver, palladium, nickel, mercury, rhodium, ruthenium, copper, molybdenum or alloys thereof.

Examples of the compound having a functional group forming a bond which is cleaved by a cleavage agent include mercaptopropyltriethoxysilane (MPTES) and the like.

Examples of the compound melted by heating include thermoplastic resins such as polystyrene, a vinyl chloride resin, polyethylene, an ABS resin, an acrylic resin, a polypropylene, an acrylonitrile/styrene resin, a methacryl resin, polyamide (PA), polyacetal (POM), polycarbonate (PC), and polybutylene terephthalate (PBT). Other examples of the compound melted by heating can be found in Japanese Patent Application Laid-Open (JP-A) No. 11-35675 and U.S. Patent Publication No. 2005/106589 and the like.

Examples of the compound having a photocleavable functional group include nitrogen-substituted aromatic esters; and compounds having functional groups such as a p-methoxyphenacyl group, a 2-nitrobenzyl group, a 2-nitrobenzyloxycarbonyl group, a benzyloxycarbonyl group, a 3,5-dimethoxybenzyloxycarbonyl group, an $\alpha,\alpha$-dimethyl-3,5-dimethoxybenzyloxycarbonyl group, a 3-nitrophenyl group, a 3-nitrophenoxy group, a 3,5-dinitrophenoxy group, a 3-nitrophenoxycarbonyl group, a phenacyl group, a 4-methoxyphenacyl group, an $\alpha$-methylphenacyl group, a 3,5-dimethoxybenzoinyl group, and a 2,4-dinitrobenzenesulfenyl group, specifically, orthophenyl benzyl ester.

Examples of the compound having a functional group which forms a photocleavable bond include a pyrimidine base having a substituted vinyl group at the 5-position of pyrimidine and a 5-cyanovinyl-1'-$\alpha$-2'-deoxyuridine derivative. Examples of the pyrimidine base having a substituted vinyl group at the 5-position of pyrimidine include a nucleic acid which has a nucleotide having 5-carboxyvinyluracil at the end as a constitutive base. Other examples of the pyrimidine base having a substituted vinyl group at the 5-position of pyrimidine can be found in, for example, Japanese Patent No. 3753942. Specific examples of the 5-cyanovinyl-1'-$\alpha$-2'-deoxyuridine derivative can be found in, for example, Japanese Patent No. 4180020. As the compound having a functional group which forms a photocleavable bond, for example, linkers described in U.S. Patent Publication No. 2011/151451 and U.S. Patent Publication No. 2008/203289 may be used. The linkers may be, for example, commercially available linkers.

Among the materials for forming the holding layer 61b, metals or alloys are preferred from the viewpoint of the stability in the process of trapping the target substance or analyte and the reactivity with the functional group for binding probes to the materials. Among the metals or alloys, gold or palladium is preferred from the viewpoint of the stability in the process of trapping the target substance or analyte and the reactivity with the functional group for binding probes to the materials.

When plastic such as polystyrene is used as the material for forming the holding layer 61b, a substance which improves affinity with the probe 60 (e.g. hydroxymethyl maleimide) may be mixed with the material in order to allow the probe 60 to be firmly held (for example, see JP-A No. 2007-023120).

It is preferable that the thickness of the holding layer 61b is suitably set within a range capable of holding the probe 60. The thickness of the holder 61b is from 0.1 to 100 nm, preferably from 0.1 to 10 nm, more preferably from 0.1 to 2 nm.

The material for forming the adhesion layer 61a of the holder 61 may be one capable of making the holding layer 61b stick to the substrate body 30a. When the material for forming the holding layer 61b is a metal or alloy, usable examples of the material for forming the adhesion layer 61a include platinum; palladium; indium tin oxide; indium oxide; titanium compounds such as titanium, titanium oxide, and titanium nitride; chromium; aluminum; nickel; and alloys containing at least one of them. Among them, platinum, palladium, titanium, chromium, indium tin oxide, and indium oxide are preferred. As the material for forming the adhesion layer 61a, a different material from the material for forming the holding layer 61b is selected.

The material for forming the adhesion layer 61a may be an organic compound. Examples of the organic compound include silane coupling agents such as aminopropyltriethoxysilane (APTES) and mercaptopropyl triethoxysilane (MPTES); amino acid; and poly-L-lysine.

It is preferable that thickness of the adhesion layer 61a is suitably set within a range capable of making the holding layer 61b stick to the substrate body 30a. The thickness of the adhesion layer 61a is usually from 0.1 to 50 nm.

In the present invention, as long as the holder 61 can hold the probe 60, it does not necessarily have a two-layer structure (the adhesion layer 61a and the holding layer 61b). That is, the holder 61 may have a multilayer structure with other layers in addition to the holding layer 61b and the adhesion layer 61a or may have a single layer structure composed only of the holding layer 61b.

When the holder 61 has the single layer structure composed only of the holding layer 61b, the thickness of the holder 61 (the holding layer 61b) is usually from 1 to 1000 nm, preferably from 1 to 200 nm, more preferably from 1 to 10 nm.

The holder 61 may be composed of a nanostructure such as a metal nano particle. When the metal nano particle is used, the diameter of the particle is preferably from 0.1 to 100 nm, more preferably from 1 to 60 nm. When the metal nanostructure is used, the thickness of the holder 61 is preferably from 0.1 to 500 nm, more preferably from 1 to 100 nm. Still more preferably, it is from 1 to 10 nm.

In the present invention, it is not necessary to have the holder 61 as long as the probe 60 can be held on the substrate body 30a. The example includes the case of immobilizing the probe 60 on the substrate body 30a through the photocleavable functional group, the functional group which forms a photocleavable bond, the bond which is cleaved by a cleavage agent, the functional group which is cleaved by the cleavage agent or the like. These functional groups and bonds may be ones which can be used for the compound having a functional group forming a bond which is cleaved by a cleavage agent, the compound having a functional group which is cleaved by the cleavage agent, the compound having a photocleavable functional group, and the compound having a functional group which forms a photocleavable bond.

The holder 61 can be formed by a film formation method according to the material for forming the holding layer 61b and the material for forming the adhesion layer 61a. When the material is a metal, examples of the film formation method include vacuum deposition, spattering, imprinting, screen-printing, metal-plating, and sol-gel techniques. From the viewpoint of the simplicity of forming the thin film on the substrate body 30a and the easiness of controlling the film thickness, the vacuum deposition technique or the spattering technique is preferred. On the other hand, when the material is plastic such as thermoplastic resin, examples of the film formation method include spin-coating, dipping, gas phase vacuum deposition, imprinting, screen-printing, and sol-gel techniques.

The immobilization of the probe on the holder 61 can be performed through a bonding group which is chemisorbed to the holder 61. Examples of the bonding group include a thiol group, a hydroxyl group, a phosphate group, a carboxyl group, a carbonyl group, an aldehyde group, a sulfonic group, and an amino group. The bonding group can be suitably selected depending on the material for forming the holding layer 61b of the holder 61. For example, when the holding layer 61b is composed of gold, a thiol group is preferred from the viewpoint of reactivity with gold.

(3) Configuration of Electrode Substrate

Subsequently, the configuration of the electrode substrate 20 included in the test chip 10 will be described.

FIG. 3 (D) is a plane explanatory view of the electrode substrate 20 included in the test chip 10 shown in FIG. 3 (A).

The electrode substrate 20 includes a substrate body 20a, the working electrode 51, the counter electrode 52, and the reference electrode 53.

The substrate body 20a is formed into a rectangular shape with almost the same size as the substrate body 30a of the probe holding substrate 30. The working electrode 51, an electrode lead 54 connected to the working electrode 51, the counter electrode 52, an electrode lead 55 connected to the counter electrode 52, the reference electrode 53, and the electrode lead 56 connected to the reference electrode 53 are formed on the surface of the substrate body 20a.

The working electrode 51 is formed into a nearly rectangular shape. The working electrode 51 is disposed at one side portion of the substrate body 20a [at the left side of FIG. 3 (D)]. The arrangement and the size of the working electrode 51 are set taking into consideration the fact that the target substance or the analyte is diffused when the target substance or the analyte is detached from the probe holding substrate 30.

The electrode lead 54 is extended from the working electrode 51 to the other side portion of the substrate body 20a [at the right side of FIG. 3 (D)]. The counter electrode 52 is arranged outside of the working electrode 51 [at the left side of the working electrode 51 in FIG. 3 (D)] on the substrate body 20a. The electrode lead 55 is bypassed the working electrode 51 from the counter electrode 52 and extended to the other side portion of the substrate body 20a [at the right side of FIG. 3 (D)]. The reference electrode 53 is arranged at the position of facing the counter electrode 52 across the working electrode 51. The electrode lead 56 is extended from the reference electrode 53 to the other side portion of the substrate body 20*a* [at the right side of FIG. 3 (D)]. The electrode lead 54 of the working electrode, the electrode lead 55 of the counter electrode 52, and the electrode lead 56 of the reference electrode 53 are arranged so as to be parallel to one another at the other side portion of the substrate body 20*a*.

The material for forming the substrate body 20*a* as well as the thickness and size of the substrate body 20*a* are the same as the material for forming the substrate body 30*a* of the probe holding substrate 30 as well as the thickness and size of the substrate body 30*a*.

Figure 4A:
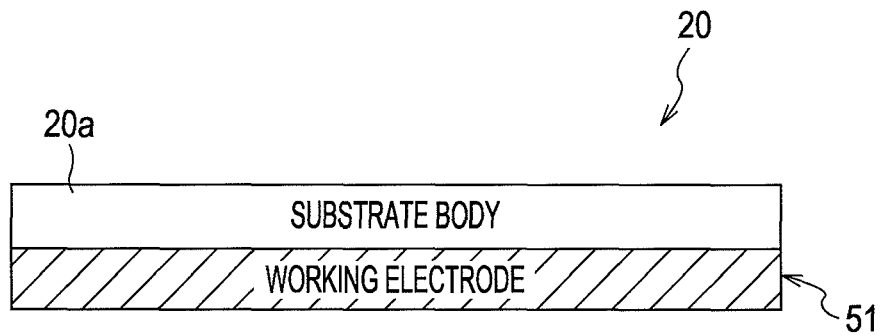
FIG. 4 is an outline view schematically showing an electrode section of the test chip according to one embodiment of the present invention.
Figure 4B:
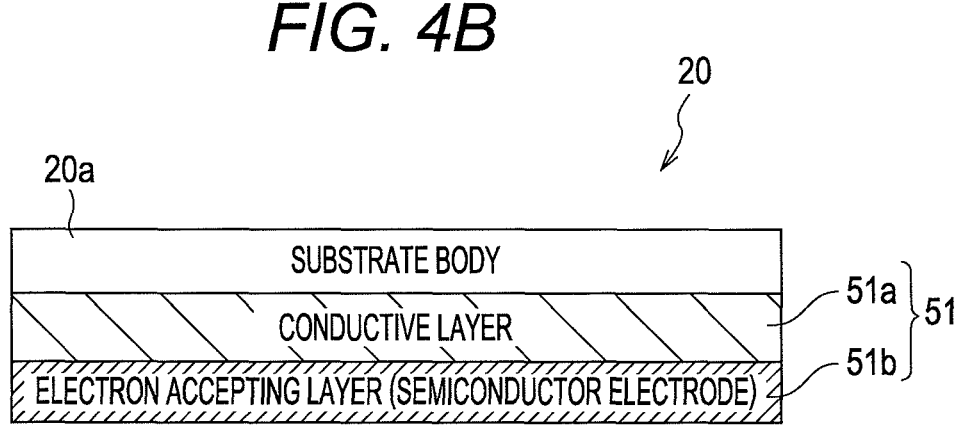
Figure 4C:
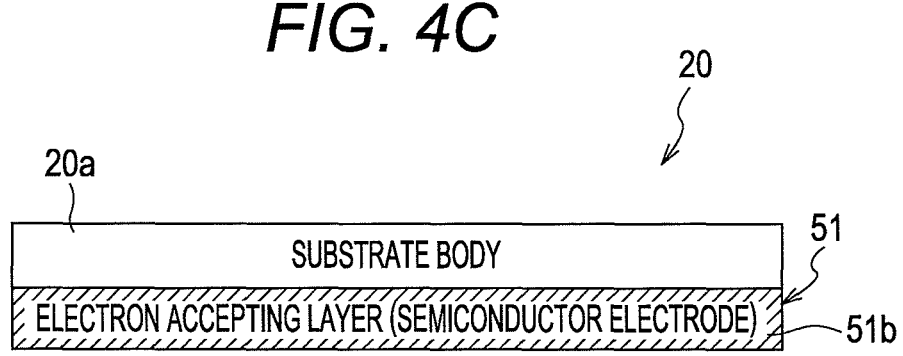
Figure 5A:
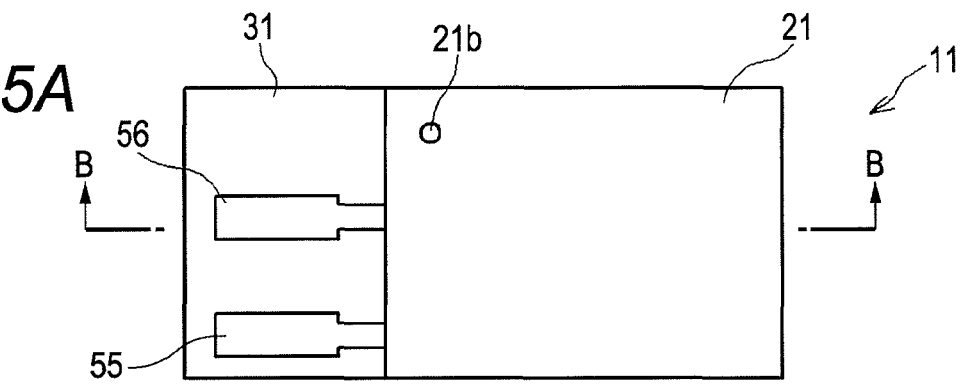
FIG. 5 (A) is a plane explanatory view showing the modification of the test chip shown in FIG. 3.
Figure 5B:
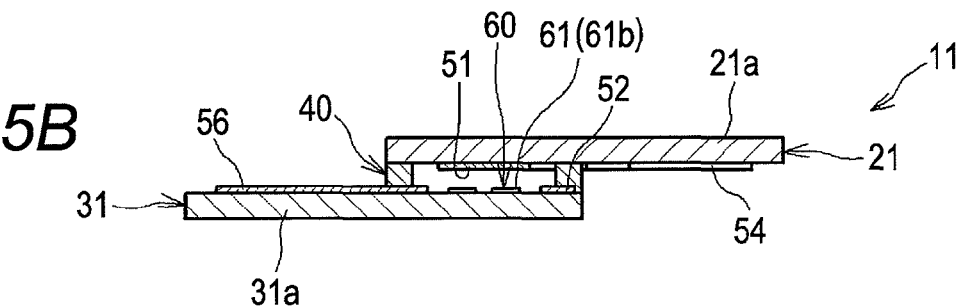
Figure 5C:
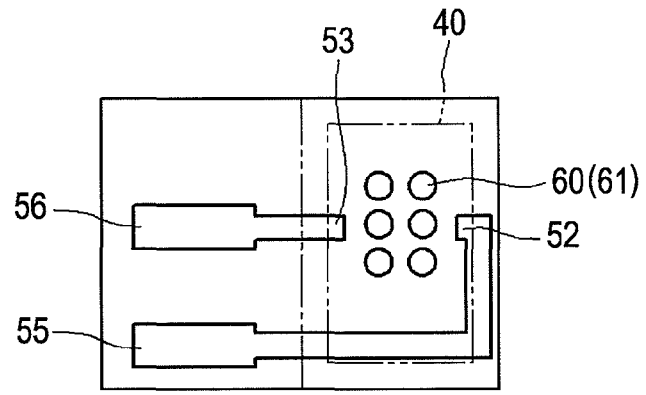
Figure 5D:
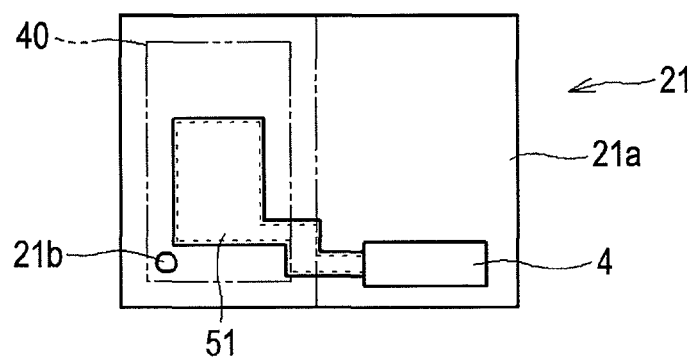
Figure 6A:
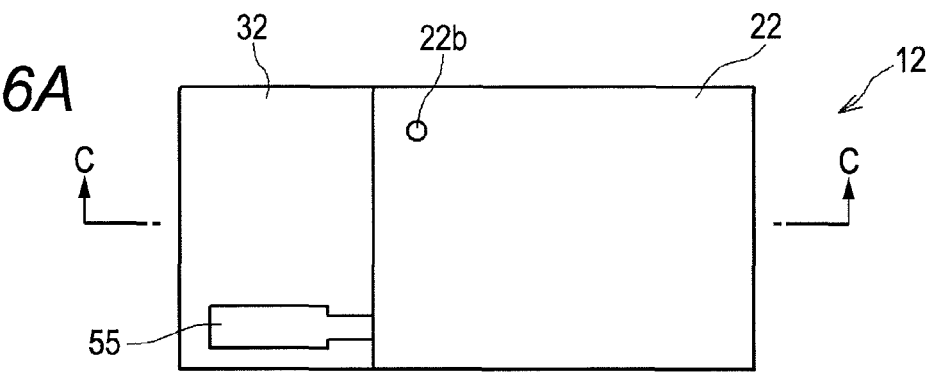
FIG. 6 (A) is a plane explanatory view showing the modification of the test chip shown in FIG. 3.
Figure 6B:
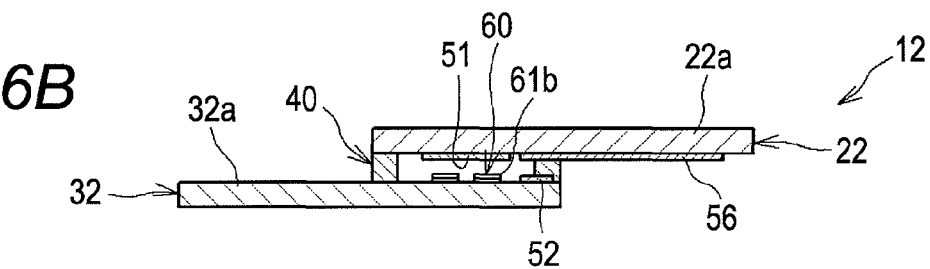
Figure 6C:
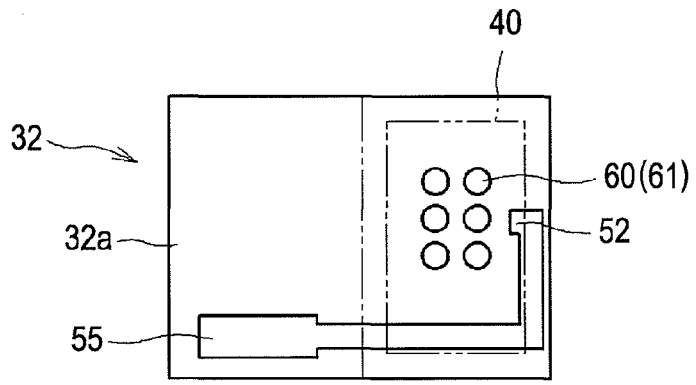
Figure 6D:
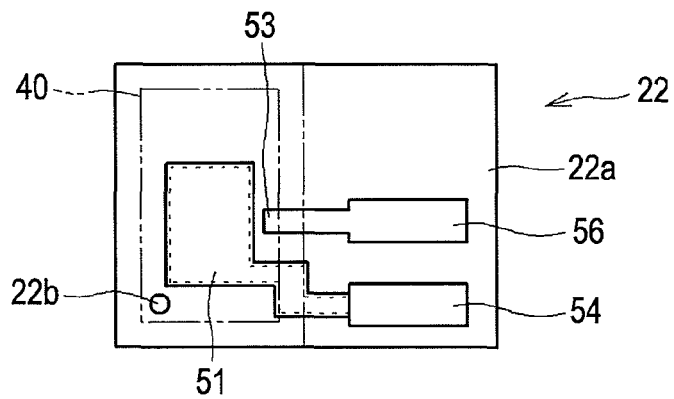
Figure 8A:
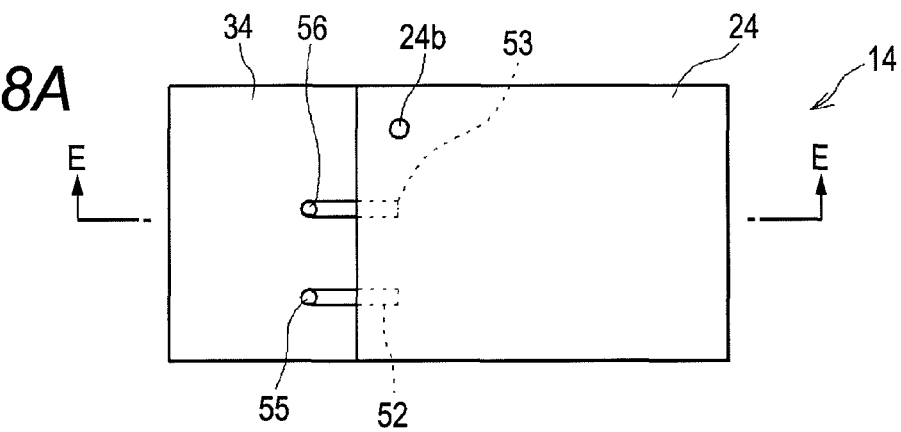
FIG. 8 (A) is a plane explanatory view showing the modification of the test chip shown in FIG. 3.
Figure 8B:
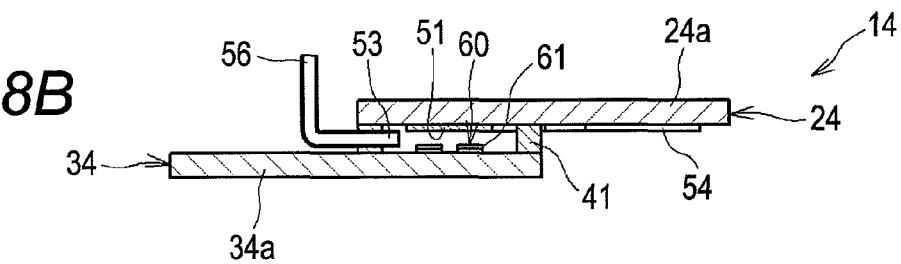
Figure 8C:
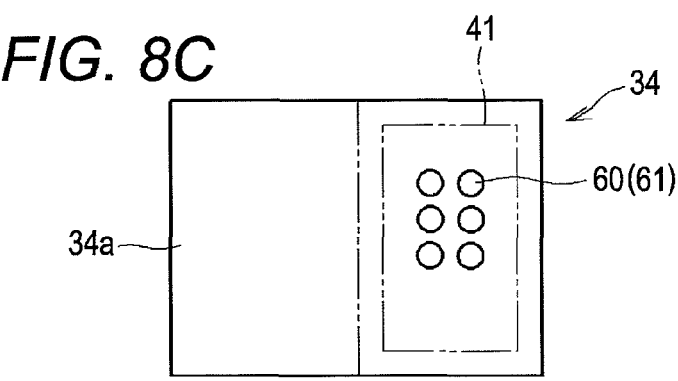
Figure 8D:
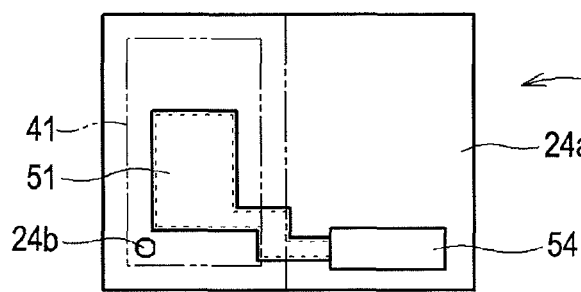
Figure 8E:
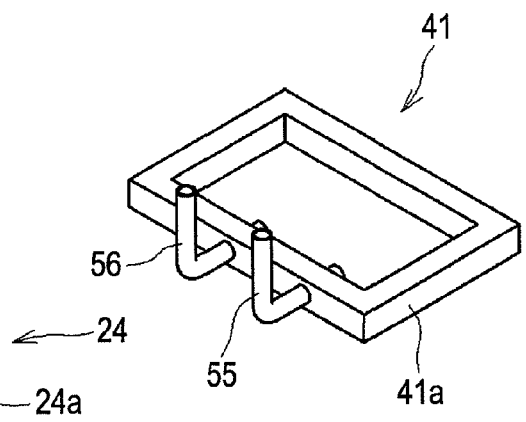
Figure 11A:
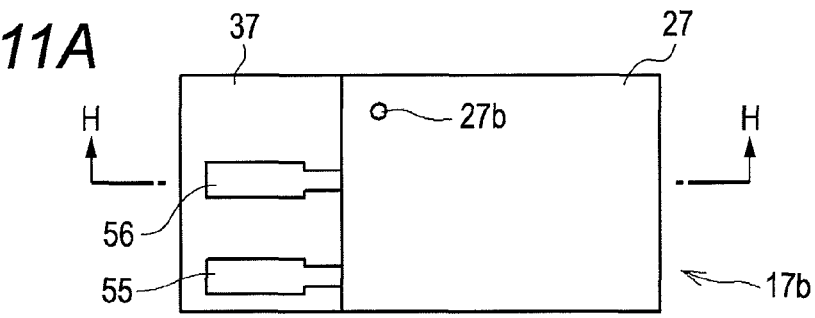
FIG. 11 is an outline explanatory view showing the detection set according to one embodiment of the present invention.
Figure 11B:
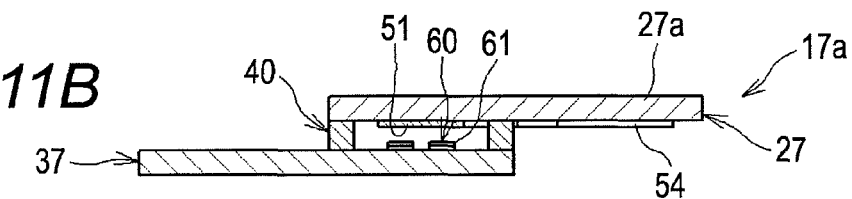
Figure 11C:
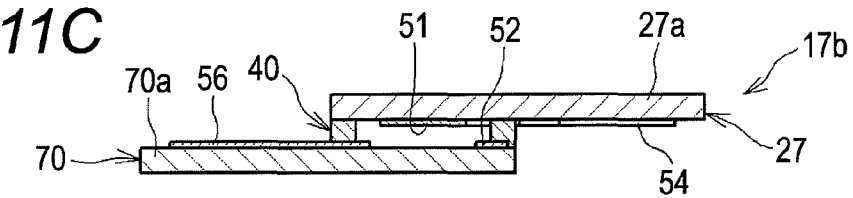
Figure 11D:
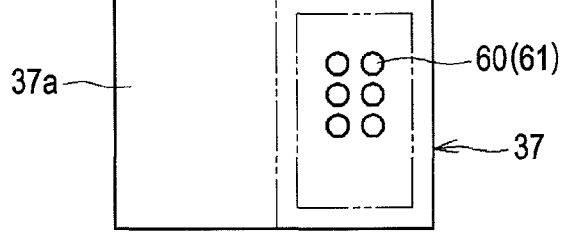
Figure 11E:
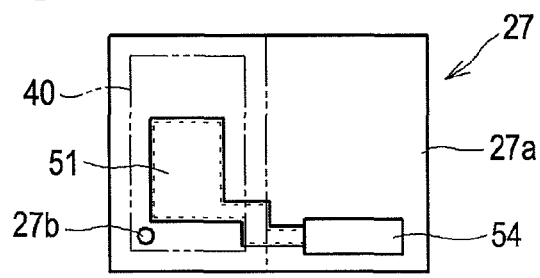
Figure 11F:
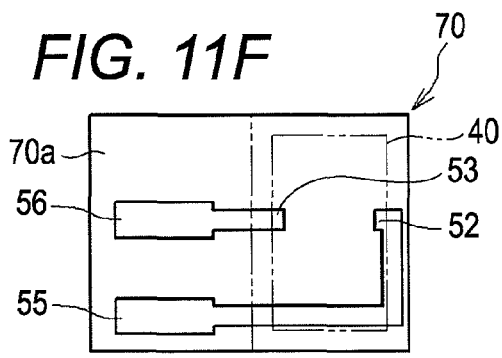

The working electrode 51 is an electrode composed of a conductive material which is stable in a solution to be used and has conductivity [see FIG. 4 (A)]. The working electrode 51 is used for the oxidation reduction current/electrochemiluminescence detection method to be described later. The working electrode to be used in the present invention is an electrode in which the labeling substance, the target substance or a trapping substance for trapping a moiety which is a part of the target substance and contains a labeling substance is not present. Here, the term "trapping" means a process of specifically trapping the labeling substance, the target substance or the moiety.

Examples of the conductive material include metals such as gold, silver, copper, carbon, platinum, palladium, chromium, aluminum, and nickel or an alloy containing at least one of those metals; conductive ceramics such as indium tin oxide and indium oxide; metal oxides such as antimony-doped tin oxide (ATO) and fluorine-doped tin oxide (FTO); titanium compounds such as titanium, titanium oxide, and titanium nitride; and carbon electrodes composed of graphite, glassy carbon, pyrolytic graphite, carbon paste, and carbon fiber.

The conductive base material may be a composite base material in which a conductive material layer composed of a material having conductivity is formed on the surface of a nonconductive base material composed of nonconductive substances such as glass and plastics. The shape of the conductive material layer may be filmy or spot-like.

In this case, the thickness of the working electrode 51 is preferably from 1 to 1000 nm, more preferably from 10 to 200 nm.

When the test chip is used for the photoelectrochemical detection method to be described later, an electrode composed of a conductive layer 51*a* formed on the surface of the substrate body 20*a* and an electron accepting layer 51*b* formed on the surface of the conductive layer 51*a* shown in FIG. 4 (B) can be used as the working electrode 51.

The conductive layer 51*a* is composed of the same conductive material as above. The thickness of the conductive layer 51*a* is preferably from 1 to 1000 nm, more preferably from 10 to 200 nm.

The electron accepting layer 51*b* contains a substance capable of accepting electrons (an electron accepting substance).

The electron accepting substance for forming the electron accepting layer may be a substance which may have an energy level capable of injecting electrons from the labeling substance (to be described later) excited by light. Here, the term "energy level capable of injecting electrons from the labeling substance excited by light" means a conduction band, for example, when a semiconductor is used as an electron accepting substance. That is, the electron accepting substance may have an energy ranking lower than an energy level of lowest unoccupied molecular orbital (LUMO) of the labeling substance (to be described later).

Examples of the electron accepting substance include element semiconductors such as silicon and germanium; oxide semiconductors containing oxides such as titanium, tin, zinc, iron, tungsten, zirconium, hafnium, strontium, indium, cerium, yttrium, lanthanum, vanadium, and niobium, tantalum; perovskite-type semiconductors such as strontium titanate, calcium titanate, sodium titanate, vanadium titanate, and potassium niobate; sulfide semiconductors containing sulfides such as cadmium, zinc, lead, silver, antimony, and bismuth; semiconductors containing nitrides such as gallium and titanium; semiconductors composed of selenides such as cadmium and lead (e.g. cadmium selenide); semiconductors containing telluride of cadmium; semiconductors composed of phosphorus compounds such as zinc, gallium, indium, and cadmium; and semiconductors containing compounds such as gallium arsenide, copper-indium selenide, and copper-indium sulfide; and compound semiconductors such as carbon or organic semiconductors. The semiconductors may be either intrinsic semiconductors or extrinsic semiconductors.

Among the above semiconductors, the oxide semiconductors are preferred. Among the intrinsic semiconductors of the oxide semiconductors, titanium oxide, zinc oxide, tin oxide, niobium oxide, indium oxide, tungsten oxide, tantalum oxide, and strontium titanate are preferred. Among the extrinsic semiconductors of the oxide semiconductors, indium tin oxide (ITO) and tin oxide containing fluorine are preferred. Indium tin oxide (ITO) or tin oxide containing fluorine has characteristics of functioning not only as an electron accepting substance, but also as a conductive base material. Thus, the use of these materials allows only the electron accepting layer to function as the working electrode without using the conductive base material.

When the conductive layer 51*a* is composed of the composite base material, the electron accepting layer 51*b* is formed on the conductive material layer. Examples of the material having conductivity for forming the conductive material layer include metals such as platinum, gold, silver, copper, aluminum, rhodium, and indium; electrically conductive ceramics such as carbon, carbide, and nitride; conductive metal oxides such as indium tin oxide (ITO), tin oxide containing fluorine, tin oxide containing antimony, zinc oxide containing gallium, and zinc oxide containing aluminum. Among them, indium tin oxide (ITO) and tin oxide containing fluorine are preferred.

The thickness of the electron accepting layer 51*b* is usually from 0.1 to 100 nm, preferably from 0.1 to 10 nm.

When the conductive layer 51*a* in itself serves as the electron accepting layer 51*b*, the electron accepting layer 51*b* may be omitted.

The working electrode 51 may be subjected to surface treatment using a silane coupling agent. The surface of the working electrode 51 can be suitably adjusted so as to be hydrophilic or hydrophobic by the surface treatment. Examples of the silane coupling agent include cationic silane coupling agents such as aminopropyl triethoxysilane (APTES).

In the test chip to be used for the photoelectrochemical detection method to be described later, as shown in FIG. 4 (C), the working electrode 51 may be composed of the electron accepting layer (semiconductor layer; semiconductor electrode) 51*b* formed on the surface of the substrate body 20*a*.

The configuration of these working electrodes can be suitably selected depending on the application of the test chip and the type of the electrochemical detection method.

The counter electrode 52 is composed of a metal layer of a conductive material. Examples of the conductive material include metals such as gold, silver, copper, carbon, platinum, palladium, chromium, aluminum, and nickel or an alloy containing at least one of those metals; conductive ceramics such as indium tin oxide and indium oxide; metal oxides such as antimony-doped tin oxide (ATO) and fluorine-doped tin oxide (FTO); and titanium compounds such as titanium, titanium oxide, and titanium nitride.

The thickness of the metal layer is preferably from 1 to 1000 nm, more preferably from 10 to 200 nm.

The reference electrode 53 is composed of a metal layer of a conductive material. Examples of the conductive material include metals such as gold, silver, copper, carbon, platinum, palladium, chromium, aluminum, and nickel or an alloy containing at least one of those metals; conductive ceramics such as indium tin oxide and indium oxide; metal oxides such as antimony-doped tin oxide (ATO) and fluorine-doped tin oxide (FTO); and titanium compounds such as titanium, titanium oxide, and titanium nitride.

The thickness of the metal layer is preferably from 1 to 1000 nm, more preferably from 10 to 200 nm.

Although the reference electrode 53 is formed in the present embodiment, it is not necessary to form the reference electrode 53 in the present invention. Depending on the type and film thickness of the electrode to be used for the counter electrode 52, when a small current (e.g. 1 µA or less) to be less affected by the voltage drop influences is measured, the counter electrode 52 may serve as the reference electrode 53. When measuring a large current, it is preferable to form the reference electrode from the viewpoint of suppressing voltage drop influences and stabilizing a voltage to be applied to the working electrode.

In the present embodiment, the working electrode 51, the counter electrode 52, and the reference electrode 53 are formed on the surface of the substrate body 20a of the electrode substrate 20. However, the working electrode 51, the counter electrode 52, and the reference electrode 53 may be arranged in a frame of the spacer 40 so as not to bring the electrodes into contact with other electrodes. That is, the working electrode 51, the counter electrode 52, and the reference electrode 53 may be formed on different substrate bodies. Further, the counter electrode 52 and the reference electrode 53 may not be a film-like electrode formed on the substrate body. For example, as described later, a cylindrical counter electrode and reference electrode may be formed in the spacer 40.

(4) Configuration of Spacer

The spacer 40 is formed into a rectangular-circular shape and is composed of silicone rubber which is an insulating material. The spacer 40 is arranged so as to surround a region where the working electrode 51, and the counter electrode 52, and the reference electrode 53 are opposed to one another. A space corresponding to the thickness of the spacer 40 is formed between a probe electrode substrate 30 and the electrode substrate 20. Thus, a space (not shown) for housing a sample and an electrolytic solution is formed among the electrodes 51, 52, and 53.

It is preferable that the thickness of the spacer 40 has a thickness capable of keeping a distance so that the target substance or the analyte which has been detached from the holder 61 of the probe holding electrode 30 and attracted to the working electrode 51 does not return to the holder 61 of the probe holding electrode 30 again.

The thickness is usually from 0.2 to 300 µm.

In the present invention, in place of silicone rubber, for example, a polyester film double-sided tape can also be used as the material for forming the spacer 40.

2. Test Chip According to Second Embodiment

Subsequently, the modification of the test chip will be described. FIG. 5 shows the modification of the test chip shown in FIG. 3 (a test chip 11 according to the second embodiment).

In the test chip 11 according to the second embodiment, the working electrode 51, the counter electrode 52, and the reference electrode 53 are formed on different substrate bodies [see FIGS. 5 (A) to (D)]. This point is largely different from the test chip 10 according to the first embodiment.

In the test chip 11, the holder 61 for holding the probe 60, the counter electrode 52, and the reference electrode 53 are formed on the surface of a substrate body 31a of a probe holding substrate 31 [see FIGS. 5 (B) and (C)]. The test chip 11 has a working electrode substrate 21 with the working electrode 51 formed on the surface of a substrate body 21a in place of the electrode substrate 20 of the test chip 10. A sample inlet 21b is formed in the substrate body 21a of the working electrode substrate 21 [see FIG. 5 (D)].

In the present embodiment, the reference electrode 53 may not be formed.

3. Test Chip According to Third Embodiment

FIG. 6 shows the modification of the test chip shown in FIG. 3 (a test chip 12 according to the third embodiment).

In the test chip 12 according to the third embodiment, the working electrode 51, the reference electrode 53, and the counter electrode 52 are formed on different substrate bodies [see FIGS. 6 (A) to (D)]. This point is largely different from the test chip 10 according to the first embodiment.

In the test chip 12, the holder 61 for holding the probe 60 and the counter electrode 52 are formed on the surface of a substrate body 32a of a probe holding substrate 32 [see FIGS. 6 (B) and (C)].

The working electrode 51 and the reference electrode 53 are formed on the surface of a substrate body 22a of an electrode substrate 22 [see FIG. 6 (D)]. A sample inlet 22b is formed in the substrate body 22a [see FIG. 6 (D)].

In the present embodiment, the reference electrode 53 may not be formed.

4. Test Chip According to the Fourth Embodiment

FIG. 7 shows the modification of the test chip shown in FIG. 3 (a test chip 13 according to the fourth embodiment).

In the test chip 13 according to the fourth embodiment, the working electrode 51, the counter electrode 52, and the reference electrode 53 are formed on different substrate bodies [see FIGS. 7 (A) to (D)]. This point is largely different from the test chip 10 according to the first embodiment.

In the test chip 13, the holder 61 for holding the probe 60 and the reference electrode 53 are formed on the surface of substrate a body 33a of a probe holding substrate 33 [see FIGS. 7 (B) and (C)].

The working electrode 51 and the counter electrode 52 are formed on the surface of a substrate body 23a of an electrode substrate 23 [see FIG. 7 (D)]. A sample inlet 23b is formed in the substrate body 23a [see FIG. 7 (D)].

In the present embodiment, the reference electrode 53 may not be formed.

5. Test Chip According to Fifth Embodiment

FIG. 8 shows the modification of the test chip shown in FIG. 3 (a test chip 14 according to the fifth embodiment).

In the test chip 14 according to the fifth embodiment, the cylindrical counter electrode 52 and the cylindrical reference electrode 53 are formed at one side portion of a member body 41a of a spacer 41 [see FIGS. 8 (A), (B), and (E)]. This point is largely different from the test chip 10 according to the first embodiment.

The cylindrical counter electrode 52 and the cylindrical reference electrode 53 are formed so as to be projected inward from one side portion of the member body 41*a* of the spacer 41 and face to the working electrode 51. The electrode leads 55 and 56 are formed so as to be projected outward from one side portion of the member body 41*a* of the spacer 41.

The test chip 14 has a working electrode substrate 24 with the working electrode 51 formed on the surface of a substrate body 24*a* in place of the electrode substrate 20 of the test chip 10. A sample inlet 24*b* is formed in the substrate body 24*a* of the working electrode substrate 24 [see FIG. 8 (D)].

In the present embodiment, the reference electrode 53 may not be formed.

6. Test Chip According to Sixth Embodiment

FIG. 9 shows the modification of the test chip shown in FIG. 3 (a test chip 15 according to the sixth embodiment).

In the test chip 15 according to the sixth embodiment, the cylindrical reference electrode 53 is formed at the one side portion of a member body 42*a* of a spacer 42 [see FIGS. 9 (A), (B), and (E)]. The counter electrode 52 is formed on the surface of a substrate body 35*a* of a probe holding substrate 35. These points are largely different from the test chip 10 according to the first embodiment.

The cylindrical reference electrode 53 is formed so as to be projected inward from one side portion of the member body 42*a* of the spacer 42 and face to the working electrode 51. The electrode lead 56 is formed so as to be projected outward from one side portion of the member body 42*a* of the spacer 42.

The test chip 15 has a working electrode substrate 25 with the working electrode 51 formed on the surface of a substrate body 25*a* in place of the electrode substrate 20 of the test chip 10. A sample inlet 25*b* is formed in the substrate body 25*a* of the working electrode substrate 25 [see FIG. 9 (D)].

In the present embodiment, the reference electrode 53 may not be formed.

7. Test Chip According to Seventh Embodiment

FIG. 10 shows the modification of the test chip shown in FIG. 3 (a test chip 16 according to the seventh embodiment).

In the test chip 16 according to the seventh embodiment, the cylindrical counter electrode 52 is formed at one side portion of a member body 43*a* of a spacer 43 [see FIGS. 10 (A), (B), and (E)]. The reference electrode 53 is formed on the surface of a substrate body 36*a* of a probe holding substrate 36. These points are largely different from the test chip 10 according to the first embodiment.

The cylindrical counter electrode 52 is formed so as to be projected inward from one side portion of the member body 43*a* of the spacer 43 and conductably face to the working electrode 51. The electrode lead 55 is formed so as to be projected outward from one side portion of the member body 43*a* of the spacer 43.

The test chip 16 has a working electrode substrate 26 with the working electrode 51 formed on the surface of a substrate body 26*a* in place of the electrode substrate 20 of the test chip 10. A sample inlet 26*b* is formed in the substrate body 26*a* of the working electrode substrate 24 [see FIG. 10 (D)].

In the present embodiment, the reference electrode 53 may not be formed.

[Configuration of Detection Set]

Subsequently, the configuration of the detection set which includes the labeling substance of the present invention and is used for the method for electrochemically detecting a target substance and the method for electrochemically detecting an analyte will be described.

FIG. 11 is an outline explanatory view showing the detection set according to one embodiment of the present invention.

The detection set according to the present embodiment includes a probe holding substrate 37 [see FIG. 11 (D)], a working electrode substrate 27 [see FIG. 11 (E)], a counter electrode substrate 70 [see FIG. 11 (F)], and the spacer 40 [see FIGS. 11 (A) to (F)].

As for the probe holding substrate 37, the working electrode substrate 27, and the counter electrode substrate 70, substrate bodies 37*a*, 27*a*, and 70*a* are formed with almost the same size.

In the detection set according to the present embodiment, when the probe holding substrate 37 and the working electrode substrate 27 are arranged so as to be overlapped at one side portion through the spacer 40, the holder 61 and the working electrode 51 are arranged on each substrate body so that the holder 61 of the probe holding substrate 37 and the working electrode 51 of the working electrode substrate 27 are vertically opposed [see FIG. 11 (B)].

When the working electrode substrate 27 and the counter electrode substrate 70 are arranged so as to be overlapped at one side portion through the spacer 40, the working electrode 51 and the counter electrode 52 are arranged on each substrate body so that a current flows between the working electrode 51 and the counter electrode 52. In this case, the electrode leads 55 and 56 are extruded from the portion where the working electrode substrate 27 and the counter electrode substrate 70 are overlapped and they are exposed to the outside [see FIG. 11 (C).]

The probe holding substrate 37 and the working electrode substrate 27 are the same as those described above. The material for forming a substrate body 70*a* of the counter electrode substrate 70 as well as the size and thickness of the substrate body 70*a* are the same as the material for forming the substrate body 20*a* of the electrode substrate 20 as well as the size and thickness of the substrate body 20*a*.

In the detection set of the present embodiment, the reference electrode 53 may not be formed.

[Method for Electrochemically Detecting Target Substance]

The method for electrochemically detecting a target substance of the present invention is a method of electrochemically detecting a target substance containing a labeling substance, including:

(1-1) bringing the target substance containing a labeling substance into contact with a probe holding substrate in which a probe for trapping the target substance containing a labeling substance are held on the substrate body and allowing the target substance containing a labeling substance to be trapped by the probe;

(1-2) detaching the labeling substance, the target substance or a moiety which is a part of the target substance and contains a labeling substance from a substrate body of the probe holding substrate obtained in the process (1-1) and attracting to a working electrode in which the labeling substance, the target substance or a trapping substance for trapping the moiety which is a part of the target substance and contains a labeling substance is not present; and (1-3) electrochemically detecting the labeling substance, the target substance or the moiety which is apart of the target substance and contains a labeling substance which has been attracted to the working electrode in the process (1-2) [referred to as a "method 1"]. The detector, the test chip, and the detection set can be used for the method for electrochemically detecting a target substance of the present invention. However, the present invention is not limited thereto.

A major characteristic of the method 1 is that the target substance is trapped by the probe of the probe holding substrate, the labeling substance, the target substance or the moiety which is a part of the target substance and contains a labeling substance is detached and attracted to the working electrode.

Accordingly, a region for trapping the target substance is different from a detection region (working electrode), and thus it is possible to prevent impurities other than the target substance from nonspecifically adsorbing onto the working electrode. Therefore, the noise when detecting the target substance can be reduced.

Since the working electrode with the probe immobilized on the working electrode is not used in the method 1, the working electrode can be easily reused. Therefore, the cost for one measurement can be reduced as compared with the case where the working electrode with the probe immobilized on the working electrode is used.

In the method 1, the labeling substance, the target substance or the moiety which is a part of the target substance and contains a labeling substance can be transferred to near the working electrode. Therefore, even if the labeling substance, the target substance or a trapping substance for trapping a target substance containing a moiety which is apart of the target substance and contains a labeling substance is not immobilized on the working electrode, the target substance containing a labeling substance can be electrochemically detected. Therefore, the present method 1 has a theoretical advantage in the measurement sensitivity obtained by a conventional electrochemical detection method using a working electrode with a trapping substance immobilized.

In the method 1, the probe holding substrate in the process (1-1) is a probe holding substrate in which the probe for trapping the target substance containing a labeling substance is held on the substrate body through the holder.

In the method 1, the working electrode is opposed to the probe holding substrate through a predetermined gap after the process (1-1) and the process (1-2) may be performed.

In the method 1, the processes (1-1) to (1-3) may be performed in a state where the electrode substrate including the working electrode and the probe holding substrate are arranged so as to be opposed to each other.

In the method 1, when the labeling substance, the target substance or a moiety which is a part of the target substance and contains a labeling substance is detached from the substrate body of the probe holding substrate, all or part of the probe may be attached to the labeling substance, the target substance or the moiety which is apart of the target substance and contains a labeling substance.

In the method 1, a procedure of trapping the target substance on the probe holding substrate and a procedure of detaching the moiety which is a part of the target substance and contains a labeling substance or the labeling substance from the probe holding substrate varies depending on the type of probe and target substance and a means for allowing the probe to be held on the substrate body of the probe holding substrate [see FIGS. 12 to 19].

In the method 1, an electrochemically or photochemically active substance is used as the labeling substance. The electrochemically active substance is detected using an oxidation reduction current and/or electrochemical luminescence based on the substance. On the other hand, the photochemically active substance is detected using electrons released by excitation of the substance by light. The method 1 can be divided broadly into the photoelectrochemical detection method (see FIG. 20) and the oxidation reduction current/electrochemiluminescence detection method (FIG. 21) depending on the type of detection technique of the labeling substance.

In the present invention, the procedure from trapping a target substance to detaching the target substance can be suitably combined with the detecting method.

Therefore, a procedure from the process (1-1) to the detaching process (1-2) (referred to as "a procedure (A)") will be first described and then a procedure from the attracting process (1-2) to the detecting process (1-3) will be described.

[Procedure (A)]

FIG. 12 shows one example of the procedure from a process of trapping a target substance to a process of detaching the target substance among the processes of the method for electrochemically detecting a target substance according to one embodiment of the present invention.

First, a liquid sample which contains the target substance containing a labeling substance is applied to a probe holding substrate 201 of the test chip [see FIG. 12 (A)].

A target substance S containing a labeling substance and another impurity F are contained in the liquid sample.

The probe holding substrate 201 includes a substrate body 201a, a holder 211 formed on the surface of the substrate body 201a, and a probe 222 immobilized on the holder 211 through a bonding group (a thiol group 221).

When the detecting process is performed by the photoelectrochemical detection method to be described later, at least one selected from the group consisting of a metal complex, an organic phosphor, a quantum dot, and an inorganic phosphor can be used as the labeling substance.

Specific examples of the labeling substance include metal phthalocyanine, a ruthenium complex, an osmium complex, an iron complex, a zinc complex, 9-phenylxanthene-based dyes, cyanine-based dyes, metallocyanine dyes, xanthene-based dyes, triphenylmethane-based dyes, acridine-based dyes, oxazine-based dyes, coumarin-based dyes, merocyanine-based dyes, rhodacyanine-based dyes, polymethine-based dyes, porphyrin-based dyes, phthalocyanine-based dyes, rhodamine-based dyes, xanthene-based dyes, chlorophyl-based dyes, eosin-based dyes, mercurochrome-based dyes, indigo-based dyes, BODIPY-based dyes, CALFluor-based dyes, Oregon green-based dyes, Rhodol green, Texas red, Cascade blue, nucleic acids (DNA and RNA), zinc cytochrome C, green fluorescent protein (GFP), yellow fluorescent protein (YFP), red fluorescent protein (RFP), peptide, cadmium selenide, cadmium telluride, $Ln_2O_3$:Re, $Ln_2O_2S$:Re, ZnO, $CaWO_4$, $MO.xAl_2O_3$:Eu, $Zn_2SiO_4$:Mn, $LaPO_4$:Ce, Tb, Cy3, Cy3.5, Cy5, Cy5.5, Cy7, Cy7.5, and Cy9 (all products are manufactured by Amersham Biosciences K.K.); Alexa Fluor 355, Alexa Fluor 405, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750 and Alexa Fluor 790 (all products are manufactured by Molecular Probes, Inc.); DY-610, DY-615, DY-630, DY-631, DY-633, DY-635, DY-636, EVOblue10, EVOblue30, DY-647, DY-650, DY-651, DY-800, DYQ-660, and DYQ-661 (all products are manufactured by Dyomics Corporation); Atto425, Atto465, Atto488, Atto495, Atto520, Atto532, Atto550, Atto565, Atto590, Atto594, Atto610, Atto611X, Atto620, Atto633, Atto635, Atto637, Atto647, Atto655, Atto680, Atto700, Atto725 and Atto740 (all products are manufactured by Atto-TEC GmbH); and VivoTagS680, VivoTag680, and VivoTagS750 (all products are manufactured by VisEn Medical Inc.). Ln represents La, Gd, Lu, or Y, Re represents a lanthanide element, M represents an alkali earth metal element, and x represents a number of 0.5 to 1.5. Concerning other examples of the labeling substance, refer to, for example, U.S. Patent Publication No. 2009/294305, U.S. Pat. No. 5,893,999, Japanese Patent Application Laid-Open (JP-A) No. 2009-023993, and U.S. Patent Publication No. 2008/000525.

On the other hand, when the detection is performed by the oxidation reduction current/electrochemiluminescence detection method below, a labeling substance that generates an oxidation reduction current when applying a voltage, or a labeling substance that emits light when applying the voltage can be used as the labeling substance.

An example of the labeling substance that generates an oxidation reduction current when applying a voltage is a metal complex containing a metal that causes electrically reversible oxidation reduction reaction as a central metal. Examples of the metal complex include tris(phenanthroline) zinc complexes, tris(phenanthroline)ruthenium complexes, tris(phenanthroline)cobalt complexes, di(phenanthroline) zinc complexes, di(phenanthroline)ruthenium complexes, di(phenanthroline)cobalt complexes, bipyridine platinum complexes, terpyridine platinum complexes, phenanthroline platinum complexes, tris(bipyridyl)zinc complexes, tris(bipyridyl)ruthenium complexes, tris(bipyridyl)cobalt complexes, di(bipyridyl)zinc complexes, di(bipyridyl)ruthenium complexes, and di(bipyridyl)cobalt complexes.

In the oxidation reduction current/electrochemiluminescence detection method, a nucleic acid which can be reused as an attractive modulator may be used as the labeling substance. When the nucleic acid is used as the labeling substance, an oxidation reduction current derived from adenine, thymine, guanine, cytosine or uracil can be used as the oxidation reduction current derived from the nucleic acid.

Examples of the labeling substance which emits light when applying a voltage include luminol, lucigenin, pyrene, diphenylanthracene, and rubrene.

The luminescence of the labeling substance can be enhanced, for example, by using luciferin derivatives such as firefly luciferin and dehydro luciferin, enhancers such as phenols such as phenylphenol and chlorophenol or naphthols.

As the labeling substance that emits light when applying a voltage, fluorescent proteins such as GFP, YFP, RFP, DsReD, mCherry, and Dendra2 and proteins such as rhodopsin may be used.

The target substance S containing a labeling substance can be produced by a method according to the type of the labeling substance being used.

The probe 222 is suitably selected depending on the type of the target substance S containing a labeling substance. For example, when the target substance S containing a labeling substance contains a nucleic acid, the probe 222 may be a nucleic acid probe hybridized to the nucleic acid or an antibody to the nucleic acid. When the target substance S containing a labeling substance includes a protein or a peptide, the probe 222 may be an antibody to the protein or the peptide, a ligand to the protein, a receptor protein to the peptide or the like.

Thereafter, only the target substance S containing a labeling substance in a liquid sample is trapped by the probe 222 of the probe holding substrate 201 [see the trapping process in FIG. 12 (B)]. The trapping process corresponds to the process (1-1).

Here, the process of allowing the target substance S containing a labeling substance to be trapped by the probe 222 can be performed under the condition where the probe 222 is bound to the target substance S containing a labeling substance. The condition can be suitably selected depending on the type of the target substance S containing a labeling substance.

For example, when the target substance S containing a labeling substance contains a nucleic acid, the process of allowing the target substance S containing a labeling substance to be trapped by the probe 222 can be performed in a solution such as a phosphate-buffered saline. The process of allowing the target substance S containing a labeling substance to be trapped by the probe 222 can be performed in a microtube (e.g. an Eppendorf tube).

Subsequently, the probe holding substrate 201 is cleaned and the impurity F is removed [see the cleaning process in FIG. 12 (C)].

The cleaning process can be performed by a procedure according to the types of the probe 222 and the target substance S containing a labeling substance.

For example, when the probe 222 and the target substance S containing a labeling substance contain nucleic acids, a solution containing SSC (composition of 1×SSC: 0.15 M of sodium chloride, 0.015 M of sodium citrate, pH 7.0) and a surfactant is used as a cleaning liquid. In this case, as the cleaning liquid has a lower concentration of SSC and a higher concentration of a surfactant, the impurity can be removed at higher efficiencies.

Thereafter, the labeling substance, the target substance or a moiety which is apart of the target substance and contains a labeling substance (in the present embodiment, a complex 230 of the target substance S containing a labeling substance, the probe 222, and the bonding group 221) is detached from the substrate body 201a of the probe holding substrate 201 by removing the holder 211 [see the detaching process in FIG. 12 (D)].

The process of removing the holder 211 is performed, for example, by bringing a solution which dissolves the holder 211 into contact with the holder 211.

The solution can be suitably selected depending on the material for forming the holder 211. For example, when gold, silver, palladium, aluminum or the like is used as the material for forming the holder 211, the solution is preferably a solution containing iodine or an iodide. The iodine or the iodide has characteristics as an electrolyte to be used in the attracting process to be described later and characteristics as a substance (etchant) which dissolves the holder 211. Thus, when the solution containing iodine or an iodide is used, an unnecessary reaction with the electrode section is suppressed as compared with the case where the etchant and the electrolyte are composed of different substances.

A specific example of the solution includes a solution that contains iodine as an electrolyte, tetrapropylammonium iodide as a supporting electrolyte, and a mixture of acetonitrile and ethylene carbonate as a solvent [e.g. a volume ratio (acetonitrile:ethylene carbonate) is 2:3].

When plastic such as polystyrene is used as the material for forming the holder 211 in order to fix the holder, for example, a solution containing acetonitrile can be used as the solution.

For example, when the holder 211 has a layer (first layer) composed of the metal or alloy which is dissolved in the solution, the probe 222 which has trapped the target substance S containing a labeling substance can be detached from the substrate body 201a by bringing the solution into contact with the holder 211.

In the procedure (A), as shown in FIG. 13, a probe holding substrate 202 which includes a holder having a two-layer structure composed of a holding layer 211b holding the probe 222 through the bonding group 221 and an adhesion layer 211a which makes the holding layer 211b stick to the substrate body 202a as the probe holding substrate may be used. In this case, the same operation as that of the procedure shown in FIG. 12 can be performed. In the procedure, the improvement in attraction efficiency and the reduction of the noise during detection can be intended by selecting a combination of a material for forming the holding layer 211b and a material for forming the adhesion layer 211a. In the detaching process, only the holding layer 211b may be removed.

For example, when the holder 211 has the first layer (the holding layer 211b) composed of the metal or alloy which is dissolved in the solution and a second layer (the adhesion layer 211a) which is formed between the holding layer 211b and the substrate body 202a and makes the holding layer 211b stick to the substrate body 202a, the probe 222 which has trapped the target substance S containing a labeling substance can be detached from the substrate body 202a by bringing the solution into contact with the holder 211.

In the procedure (A), as shown in FIG. 14, a probe holding substrate 203 in which a probe 223 is directly held on the holder 211 without being through the bonding group may be used.

Such an example includes a case where the holder 211 is composed of the thermoplastic resin. In this case, the probe 223 which has trapped the target substance S containing a labeling substance can be detached from a substrate body 203a by heating the probe holding substrate 203 in which the target substance S containing a labeling substance is trapped.

FIG. 15 shows the procedure when bonds Sa and Sb which are cleaved by heating, light or the cleavage agent are included in the target substance S containing a labeling substance. It is preferable that a cleavable binding site is composed of an organic group selected from straight-chain, branched-chain, and cyclic organic groups. The cleavable binding site includes preferably 1 to 100 atoms, more preferably 1 to about 50 atoms. The atom is preferably selected from a hydrogen atom, a carbon atom, a boron atom, a nitrogen atom, an oxygen atom, a sulfur atom, a silicon atom, a phosphorus atom, halogen, and an alkali metal atom. Examples thereof include a group that is subjected to reduction cleavage, for example, an organic group containing a disulfide bond that is cleaved by thiol compounds such as ethanethiol, mercaptoethanol, and dithiothreitol (DTT); a peroxide bond (—O—O—) that can be cleaved by a thiol compound, an amine compound, a phosphine compound or the like; an organic group containing a nitrogen-substituted aromatic ester group that is photochemically cleavable; an organic group containing an ester bond that can be cleaved by esterase, hydrolase or the like; an organic group containing an amide bond or peptide bond which can be cleaved by protease (proteolytic enzyme), peptidase or the like; and a glycoside group that can be cleaved by glycosidase. In this case, in the detaching process, the bonds Sa and Sb can be cut by only applying heat, light or the cleavage agent to a probe holding substrate 204 in which the probe 223 which has trapped the target substance S containing a labeling substance so that a part of the target substance S containing a labeling substance (a moiety containing a labeling substance) can be detached from the probe holding substrate 204 [see FIG. 15 (D)]. Therefore, the detaching process can be easily performed.

FIG. 16 shows the procedure when bonds 222a and 222b which are cleaved by heating, light or the cleavage agent are included in the probe 222. In this case, in the detaching process, the bonds 222a and 222b can be cut by only applying heat, light or the cleavage agent to a probe holding substrate 205 which has trapped the target substance S containing a labeling substance so that the target substance S containing a labeling substance and a product containing a part (222b) of the probe 222 can be detached from the probe holding substrate 205 [see FIG. 16 (D)]. Therefore, the detaching process can be easily performed.

FIGS. 15 and 16 show examples of the case where the probe holding substrate in which the probe is directly immobilized on the substrate body is used. However, in the procedures shown in FIGS. 15 and 16, the probe holding substrate in which the probe is immobilized on the substrate body through the holder may be used.

FIG. 17 shows the procedure when the target substance S containing a labeling substance is specifically associated with the probe 222 to form a complex 233 and an association of the complex 233 is unstable to heat. Examples thereof include hybridization between nucleic acids and antigen-antibody reaction between proteins. In this case, in the detaching process, the target substance S containing a labeling substance can be easily dissociated from the probe 222 by applying heat to a probe holding substrate 206 which has trapped the target substance S containing a labeling substance [see FIG. 17 (D)]. Therefore, the detaching process can be easily performed. The same is true when the association of the complex 233 becomes unstable due to the presence of a competitive substance.

When the target substance containing a labeling substance and the probe contains DNA, as shown in FIG. 18, the target substance containing a labeling substance ["$S_1$" in the drawing] is specifically hybridized to the probe 222 and thus a recognition sequence that is cut by an enzyme such as the restriction enzyme may be formed. In such a case, in the detaching process, a double-stranded DNA portion having a recognition sequence is cut by bringing the probe holding substrate 207 in which the target substance $S_1$ containing a labeling substance is trapped into contact with the restriction enzyme ("cleavage agent" in the drawing) so that a product $S_2$ containing a part of the target substance $S_1$ containing a labeling substance can be detached from the probe holding substrate 207 [see FIG. 18 (D)]. Therefore, the detaching process can be easily performed.

The target substance containing a labeling substance may be composed of a material for detachably holding the moiety containing a labeling substance. The material is not particularly limited. Examples thereof include a metal or alloy which is dissolved in a solution described above, a metal or alloy which can be electrolyzed (ionized by oxidation reduction reactions), a compound having a functional group forming a bond which is cleaved by a cleavage agent, a compound having a functional group which is cleaved by the cleavage agent, a compound melted by heating, a compound having a photocleavable functional group, and a compound having a functional group which forms a photocleavable bond.

Examples of the metal or alloy to be dissolved in the solution include gold, platinum, silver, palladium, nickel, mercury, rhodium, ruthenium, copper, molybdenum or alloys thereof.

Examples of the compound having a functional group forming a bond which is cleaved by a cleavage agent include a compound having a disulfide bond such as a dimer of cysteine.

Examples of the compound melted by heating include thermoplastic resins such as polystyrene, a vinyl chloride resin, polyethylene, an ABS resin, an acrylic resin, a polypropylene, acrylonitrile/styrene resin, a methacryl resin, polyamide (PA), polyacetal (POM), polycarbonate (PC), and polybutylene terephthalate (PBT). Other examples of the compound melted by heating can be found in Japanese Patent Application Laid-Open (JP-A) No. 11-35675 and Japanese Patent Application National Publication (Laid-Open) No. 2008-506386.

Examples of the compound having a photocleavable functional group include nitrogen-substituted aromatic esters; and compounds having functional groups such as a p-methoxyphenacyl group, a 2-nitrobenzyl group, a 2-nitrobenzyloxycarbonyl group, a benzyloxycarbonyl group, a 3,5-dimethoxybenzyloxycarbonyl group, an α,α-dimethyl-3,5-dimethoxybenzyloxycarbonyl group, a 3-nitrophenyl group, a 3-nitrophenoxy group, a 3,5-dinitrophenoxy group, a 3-nitrophenoxycarbonyl group, a phenacyl group, a 4-methoxyphenacyl group, an α-methylphenacyl group, a 3,5-dimethoxybenzoinyl group, and a 2,4-dinitrobenzenesulfenyl group (specifically, orthophenyl benzyl ester).

Examples of the compound having a functional group which forms a photocleavable bond include a pyrimidine base having a substituted vinyl group at the 5-position of pyrimidine and a 5-cyanovinyl-1'-α-2'-deoxyuridine derivative. Examples of the pyrimidine base having a substituted vinyl group at the 5-position of pyrimidine include a nucleic acid which has a nucleotide having 5-carboxyvinyluracil at the end as a constitutive base. Other examples of the pyrimidine base having a substituted vinyl group at the 5-position of pyrimidine can be found in, for example, Japanese Patent No. 3753942. Specific examples of the 5-cyanovinyl-1'-α-2'-deoxyuridine derivative can be found in, for example, Japanese Patent No. 4180020. As the compound having a functional group which forms a photocleavable bond, for example, a linker described in Japanese Patent Application National Publication (Laid-Open) No. 2008-542783. The linker may be, for example, a commercially available linker.

As the material for detachably holding the moiety containing a labeling substance, metals or alloys are preferred from the viewpoint of the stability in the process of trapping the target substance or analyte and the reactivity with the functional group for binding probes to the materials. Among the metals or alloys, gold, silver or palladium is preferred from the viewpoint of the stability in the process of trapping the target substance or analyte and the reactivity with the functional group for binding probes to the materials. Particularly, examples thereof include nanostructures composed of gold such as golden nanoparticles and golden nanowires.

An example of the procedure from a process of trapping a target substance to a process of detaching the target substance when the target substance containing a labeling substance that has the material for detachably holding the moiety containing a labeling substance is used, among the processes of the method for electrochemically detecting a target substance according to another embodiment of the present invention is shown in FIG. 19. In FIG. 19, the process of detecting proteins is shown as an example.

(A) Immobilization of Primary Antibody 224a and Antigen 224b

A primary antibody 224a which is specifically bound to an antigen 224b is immobilized on the holder 211 arranged on the substrate body 208a and the antigen 224b is further bound to the primary antibody 224a. In this state, a complex of the primary antibody 224a and the antigen 224b can be recognized as a probe 224 (see FIG. 19 (A)). The holder 211 need not have solubility.

(B) Trapping of Target Substance $S_3$ Containing Labeling Substance

Golden nanoparticles $S_{3A}$ in which a plurality of secondary antibodies $S_{3B1}$ containing a labeling substance $S_{3B2}$ which is specifically bound to the antigen 224b are immobilized are used as the target substance $S_3$ containing a labeling substance and they are reacted with probes 224 immobilized on holder 211 arranged on the probe holding substrate 208 (see FIG. 19 (B)).

(C) Cleaning

By washing the probe holding substrate 208, an excessive amount of the target substance $S_3$ containing a labeling substance which has unreacted are cleaned (see FIG. 19 (C)).

In the process of cleaning, for example, the washing solution for a system of detecting proteins such as 1% TBS containing tween 20 and PBS or the washing solution for a system of detecting genes such as SSPE (Standard saline phosphate EDTA) and SSC (Standard sakine citrate) can be used.

(D) Detachment

A golden nanoparticle $S_{3A}$ is dissolved by adding the solvent including the dissolving agent for detaching and attracting a part of the target substance $S_3$ on the probe holding substrate 208. A part of the target substance $S_3$ containing a labeling substance bound to the golden nanoparticle $S_{3A}$ is detached from the probe holding substrate 208 and attracted to the working electrode (see FIG. 19 (D)).

As the target substance containing a labeling substance, the golden nanoparticle $S_{3A}$ in which the plurality of secondary antibodies $S_{3B}$ containing a labeling substance were immobilized were used. However, the labeling substance may be directly bound to the golden nanoparticle $S_{3A}$ without binding the labeling substance to the secondary antibody $S_{3B1}$. The labeling substance may be bound to a substance which is not specifically bound to the analyte and then bound to the golden nanoparticle $S_{3A}$.

The use of dithiothreitol (DTT) allows a part of the target substance containing a labeling substance to be separated without dissolving the golden nanoparticle. When the part of the target substance containing a labeling substance is bound to the golden nanoparticle with a thiol group and DTT which dissociates a bond between the thiol group and gold is added thereto, the part of the target substance containing a labeling substance on the golden nanoparticle is separated from the golden nanoparticle.

[Procedure (B)]
1. Photoelectrochemical Detection Method

FIG. 20 shows one example of the procedure from a process of attracting a target substance to a process of detecting the target substance among the processes of the method for electrochemically detecting a target substance according to one embodiment of the present invention. In FIG. 20, the case of detecting a target substance by the photoelectrochemical detection method will be described. In the present embodiment, a modified target substance 240a having an attractive modulator 241 added to the target substance S [see FIG. 20 (A)] is used will be explained as an example.

In the photoelectrochemical detection method, a labeling substance which becomes an excited state by irradiation with light and releases electrons is used as the labeling substance.

Examples of the attractive modulator 241 include nucleic acids such as DNA and RNA.

If the target substance S containing a labeling substance can be attracted to the working electrode, the attractive modulator 241 may not be added.

In the photoelectrochemical detection method, the modified target substance 240a is attracted to the working electrode 51 [see the attracting process of FIG. 20 (B)].

The attracting process is a process of attracting the modified target substance 240a to a region where electrons can be transported between the working electrodes in which the trapping substance is not present. In the attracting process, the modified target substance 240a is immobilized on the working electrode 51.

Here, the term "region where electrons can be transported between the working electrodes in which the trapping substance is not present" usually means a region ranging from 0 to 10 nm from the working electrode 51.

The working electrode 51 to be used for the photoelectrochemical detection method is an electrode capable of accepting electrons released by light excitation of the labeling substance. Therefore, the configuration and material of the working electrode 51 are not limited so long as electrons are transported between the working electrode and the labeling substance.

The attraction of the modified target substance 240a to the working electrode 51 can be performed by using the modified target substance 240a, hydrophobic or hydrophilic interactions between the attracting liquid and the working electrode 51, or electrophoretic effects caused by applying a voltage to the working electrode 51 or the counter electrode 52.

The attracting process is performed by, for example, 1) changing the hydrophobicity and hydrophilicity of the attracting liquid or increasing hydrophobic or hydrophilic interaction between the modified target substance 240a and the working electrode 51 [i.e., attracting the modified target substance 240a to the working electrode in which the trapping substance is not present (the working electrode 51) by differences in polarity] (the attraction method 1);

2) applying a positive or negative voltage to the working electrode 51 to increase electrophoretic effects depending on the charge of the modified target substance 240a [i.e., attracting the modified target substance 240a to the working electrode (working electrode 51) in which the trapping substance is not present by using the electrophoretic effects] (the attraction method 2). The attraction methods 1 and 2 may be performed independently or in combination with each other.

In the attraction method 1, when nucleic acid is used as the attractive modulator 241, it is preferable that the attracting liquid contains a chaotropic ion from the viewpoint of increasing hydrophobic or hydrophilic interaction between the target substance and the working electrode 51 and easily attracting the target substance to near the working electrode 51.

Examples of the chaotropic ion include an iodide ion, a bromide ion, a guanidine ion, a thiocyanic acid ion, a tribromoacetic acid ion, a trichloroacetic acid ion, a perchlorate ion, a dichloroacetic acid ion, a nitrate ion, a chloride ion, an acetate ion, a barium ion, a calcium ion, a lithium ion, a cesium ion, a potassium ion, and a magnesium ion.

When the attracting liquid contains the chaotropic ion, the concentration of chaotropic ion in the attracting liquid varies depending on the type of chaotropic ion to be used. The concentration is usually from 1.0 to 8.0 mol/L. When the chaotropic ion is a guanidine ion, the concentration of chaotropic ion in the attracting liquid is usually from 4.0 to 7.5 mol/L. When the chaotropic ion is a thiocyanic acid ion, the concentration of chaotropic ion in the attracting liquid is usually from 3.0 to 5.5 mol/L.

When nucleic acids (DNA and RNA) are used as the labeling substance or the attractive modulator 241, the target substance containing a labeling substance can be attracted to near the working electrode 51 by using conventional methods for extracting and purifying nucleic acids.

Examples of the method of extracting and purifying nucleic acids include a method of using a liquid phase and a method of using a carrier for binding nucleic acids. Examples of the method of using a liquid phase include a phenol/chloroform extraction method (Biochimica et Biophysica acta, vol. 72, pp. 619-629 (1963), an alkali-SDS method (Nucleic Acid Research, vol. 7, pp. 1513-1523 (1979)), and a method of adding ethanol to a buffer containing guanidine hydrochloride to precipitate nucleic acids (Analytical Biochemistry, 162, 1987, 463). Examples of the method of using a carrier for binding nucleic acids include a method of isolating nucleic acids comprising: adsorbing nucleic acids to glass particles by using the glass particles and a sodium iodide solution (Proc. Natl. Acad. Sci. USA, 76-2:615-619-1979) and a method of using silica particles and chaotropic ions [see, for example, J. Clinical. Microbiology, vol. 28, pp. 495-503 (1990) and Japanese Patent No. 2680462].

In the method of using silica particles and chaotropic ions, a solution which contains chaotropic ions capable of releasing silica particles to which nucleic acids are bound from nucleic acids in a sample is first mixed with the sample in order to bind nucleic acids to silica particles. Next, impurities are removed by washing. Thereafter, the nucleic acids bound to silica particles are recovered. According to the method, the nucleic acids can be extracted simply and rapidly. Additionally, the method is suitable for not only the extraction of DNA, but also for extraction of RNA, and is very excellent in terms of obtaining nucleic acids with high purity.

When the modified target substance 240a contains a nucleic acid as the labeling substance or the attractive modulator 241, the modified target substance 240a can be attracted to near the working electrode 51 by using a solvent to be used for the method of extracting and purifying nucleic acids as an attracting liquid. In this case, it is preferable that a guanidine ion, an iodide ion, a bromide ion, and a thiocyanic acid ion or an arbitrary combination thereof is used as the chaotropic ion and an electrode for binding nucleic acids (for example, indium oxide containing tin) is used as the working electrode.

When the modified target substance 240a contains nucleic acids (DNA and RNA) as the labeling substance or the attractive modulator 241, the attracting liquid may contain a buffer, if necessary. The buffer may be a buffer which is generally used to hold nucleic acids stably. It is preferable that the buffer has a buffer capacity at a neutral pH, i.e., at a pH of 5.0 to 9.0 from the viewpoint of holding nucleic acids stably. Examples of the buffer include Tris-HCL salt, sodium-tetraborate-hydrochloric acid, and potassium dihydrogenphosphate-sodium tetraborate. The concentration of the buffer is preferably from 1 to 500 mmol/L.

On the other hand, in the attraction method 2, a positive or negative voltage is applied to the working electrode depending on the charge of the modified target substance 240a. For example, when the modified target substance 240a contains nucleic acids (DNA and RNA) as the labeling substance or the attractive modulator 241, the nucleic acid is negatively charged. Therefore, the modified target substance 240a can be attracted to near the working electrode 51 by applying a positive voltage to the working electrode 51.

Since the iodine or the iodide can be a mediator for the oxidation reduction reaction, it can be used in order to detect electrochemical signals from the modified target substance 240a. A solution prepared by dissolving iodine and tetrapropylammonium iodide in a mixed solvent of acetonitrile and ethylene carbonate is a solution that can be used for the detachment of the target substance containing a labeling substance from the substrate body, the attraction of the target substance containing a labeling substance to the working electrode 51, and the electrochemical detection.

If the composition of the solution is changed, the detaching process and the attracting process can be performed by using different solutions.

The target substance containing a labeling substance can be detached from the substrate body by using, for example, a calcium iodide solution. However, when the calcium iodide solution is used as it is, the target substance containing a labeling substance is less attracted to the working electrode 51. Then, the probe and the target substance containing a labeling substance trapped by the probe can be efficiently attracted to the working electrode by adding an organic solvent like acetonitrile to the calcium iodide solution after the detachment.

In the photoelectrochemical detection method, subsequently, the modified target substance 240a is detected by irradiating the modified target substance 240a, which is present near the working electrode 51, with light to excite the labeling substance and measuring the photocurrent ["the detection process" in FIG. 20 (C)].

In the detection process, when the attracting liquid is used in the attracting process, the attracting liquid can be substituted for an electrolytic solution suitable for the electrochemical detection, if necessary. In this case, the modified target substance 240a is electrochemically detected in the presence of the electrolytic solution.

When the attracting liquid has characteristics of supplying electrons to the labeling substance in an oxidized state and the electrochemical detection of the target substance is possible, the attracting liquid may be used with no change in the detection process.

As the electrolytic solution, a solution containing an electrolyte composed of salts which may supply electrons to the labeling substance in an oxidized state, an aprotic polar solvent, a protonic polar solvent, or a mixture of the aprotic polar solvent and the protonic polar solvent can be used. The electrolytic solution may further contain other components, if desired.

Examples of the electrolyte include iodide, bromide, a metal complex, thiosulfate, sulfite, and a mixture thereof. Specific examples of the electrolyte include metal iodides such as LiI, NaI, KI, CsI, and $CaI_2$; iodine salts of quaternary ammonium compounds such as tetraalkylammonium iodide, pyridinium iodide, imidazolium iodide; metal bromides such as LiBr, NaBr, KBr, CsBr, and $CaBr_2$; bromine salts of quaternary ammonium compounds such as tetraalkylammonium bromide and pyridinium bromide; metal complexes such as a ferrocyanic acid salt and a ferricinium ion; thiosulfates such as sodium thiosulfate, ammonium thiosulfate, potassium thiosulfate, and calcium thiosulfate; sulfites such as sodium sulfite, potassium sulfite, ammonium sulfite, iron sulfite, sodium hydrogensulfite, and calcium sulfite; and a mixture thereof. Among them, tetrapropylammonium iodide and $CaI_2$ are preferred.

The electrolyte concentration of the electrolytic solution is preferably from 0.001 to 15 M.

Water, a polar solvent containing a buffer component and a main component of water, or the like may be used as the protonic polar solvent.

Examples of the aprotic polar solvent include nitriles such as acetonitrile ($CH_3CN$); carbonates such as propylene carbonate and ethylene carbonate; heterocyclic compounds such as 1,3-dimethylimidazolinone, 3-methyloxazolinone and dialkylimidazolium salt; dimethylformamide, dimethyl sulfoxide, and sulfolane. Among the aprotic polar solvents, acetonitrile is preferred. The protonic polar solvent and the aprotic polar solvent can be used alone or mixed for use. As a mixture of the protonic polar solvent and the aprotic polar solvent, a mixture of water and acetonitrile is preferred.

When the modified target substance 240a is irradiated with light, a light source which can emit light in a wavelength capable of photoexciting the labeling substance can be used. The light source can be suitably selected depending on the type of the labeling substance. Examples of the light source include fluorescent lamps, black light, bactericidal lamps, incandescent lamps, low-pressure mercury lamps, high-pressure mercury lamps, xenon lamps, mercury-xenon lamps, halogen lamps, metal halide lamps, light emitting diodes (white LED, blue LED, green LED, and red LED), lasers (carbon dioxide lasers, dye lasers, semiconductor lasers), and sunlight. Among the light sources, fluorescent lamps, incandescent lamps, xenon lamps, halogen lamps, metal halide lamps, light emitting diodes, and sunlight are preferred. In the detection process, the modified target substance 240a may be irradiated with only light in a specified wavelength region using a spectrometer or a bandpass filter, if necessary.

In the measurement of a photocurrent derived from the labeling substance, for example, a measurement device which includes an ammeter, a potentiostat, a recorder, and a computer can be used.

In the detection process, the amount of the modified target substance 240a can be examined by quantifying the photocurrent.

The trapping substance for trapping the modified target substance 240a is not present on the working electrode 51 to be used for the photoelectrochemical detection. Therefore, the working electrode 51 can be cleaned by a simple treatment so that it is reusable.

The cleaning of the working electrode can be performed by ultraviolet ray-ozone cleaning (UV-$O_3$ cleaning) or the like. In the UV-$O_3$ cleaning, an organic compound is decomposed by a powerful oxidation effect in processes of decomposition of the organic compound by ultraviolet rays and formation and decomposition of $O_3$, and it is removed from the surface of the electrode.

When a nucleic acid is used as the labeling substance or the attractive modulator 241, the modified target substance 240a can also be dissociated from the working electrode 51 by applying a negative voltage to the working electrode in a suitable solution. This is because the nucleic acid is negatively charged. Examples of the solution include phosphate-buffered saline (PBS), TEB [composition: 10 mM Tris-HCL buffer, 1 mM EDTA], and water.

In the present embodiment, the same operation as above can be performed when the attractive modulator 241 contains the labeling substance or a moiety which is a part of the target substance S and contains a labeling substance in place of the target substance S.

2. Oxidation Reduction Current/Electrochemiluminescence Detection Method

FIG. 21 is a process explanatory view showing the procedure from a process of attracting a target substance to a process of detecting the target substance among the processes of the method for electrochemically detecting the target substance according to another embodiment of the present invention. In FIG. 21, the case of detecting a target substance by the oxidation reduction current/electrochemiluminescence detection method will be described. In the present embodiment, the case where a modified target substance 240b having the attractive modulator 241 added to the target substance S [see FIG. 21 (A)] is used will be explained as an example.

In the oxidation reduction current/electrochemiluminescence detection method, a labeling substance which generates an oxidation reduction current when a voltage is applied or a labeling substance which emits light when a voltage is applied is used as the labeling substance.

In the oxidation reduction current/electrochemiluminescence detection method, the modified target substance 240b is attracted to the working electrode 51 [the attracting process of FIG. 21 (B)].

The attracting process is a process of attracting the labeling substance to a region where the electronic excitation occurs by the working electrode in which the trapping substance is not present.

The attraction process of the modified target substance 240b to the working electrode 51 can be performed by the same operation as that of the attracting process in the photoelectrochemical detection method.

Here, the term "region where the electronic excitation occurs by the working electrode in which the trapping substance is not present" is a region where electrons are transferred from the working electrode to the labeling substance by applying a voltage and the labeling substance can get into an electronically excited state. The region is usually a region ranging from 0 to 10 nm from the working electrode.

In the oxidation reduction current/electrochemiluminescence detection method, a voltage is subsequently applied to the modified target substance 240b which is present near the working electrode 51. The modified target substance 240b is detected by measuring the oxidation reduction current or light based on the labeling substance [see the detection process of FIG. 21 (C)]. FIG. 21 (C) is shown taking an example of the case of measuring the light generated by applying a voltage.

In the detection process, when the attracting liquid is used in the attracting process, the attracting liquid can be substituted for an electrolytic solution suitable for the electrochemical detection in the same manner as the case of the photoelectrochemical detection method, if necessary. In this case, the substance to be detected containing a labeling substance is electrochemically detected in the presence of the electrolytic solution.

When measuring the oxidation reduction current in the detection process, a measurement device which includes for example, a potentiostat, a function generator, a recorder, and a computer can be used.

In this case, the amount of the target substance can be examined by quantifying the oxidation reduction current.

When measuring the light based on the labeling substance in the detection process, a photon counter can be used. In this case, the light can be indirectly detected by using an optical fiber electrode obtained by forming a transparent electrode at the end of an optical fiber in place of the electrode (see U.S. Pat. Nos. 5,776,672 and 5,972,692).

The trapping substance for trapping the modified target substance 240b is also not present on the working electrode 51 to be used for the oxidation reduction current/electrochemiluminescence detection method. Therefore, the working electrode 51 can be cleaned by a simple treatment in the same manner as the case where the working electrode 51 to be used for the photoelectrochemical detection method so that it is reusable.

The process of cleaning the working electrode can be performed by the same operation as the process of cleaning the working electrode in the photoelectrochemical detection method.

In the present embodiment, the same operation as above can be performed when an attractive modulator 241 contains the labeling substance or a moiety which is a part of the target substance S and contains a labeling substance in place of the target substance S.

[Method for Electrochemically Detecting Analyte]

Subsequently, the method for electrochemically detecting an analyte of the present invention will be described.

The method for electrochemically detecting an analyte of the present invention is a method of electrochemically detecting an analyte, including:

(2-1) bringing an analyte and a label binding substance obtained by labeling a binding substance for trapping the analyte with a labeling substance into contact with the analyte or probe for trapping the label binding substance is held on a probe holding substrate of the substrate body to form a complex containing the labeling substance and the analyte on the probe holding substrate;

(2-2) detaching at least the label binding substance or the labeling substance from the holder of the probe holding substrate obtained in the process (2-1) and attracting to a working electrode in which the label binding substance or a trapping substance for trapping the labeling substance is not present; and (2-3) electrochemically detecting the label binding substance or the labeling substance which has been attracted to the working electrode in the process (2-2).

Figure 22:
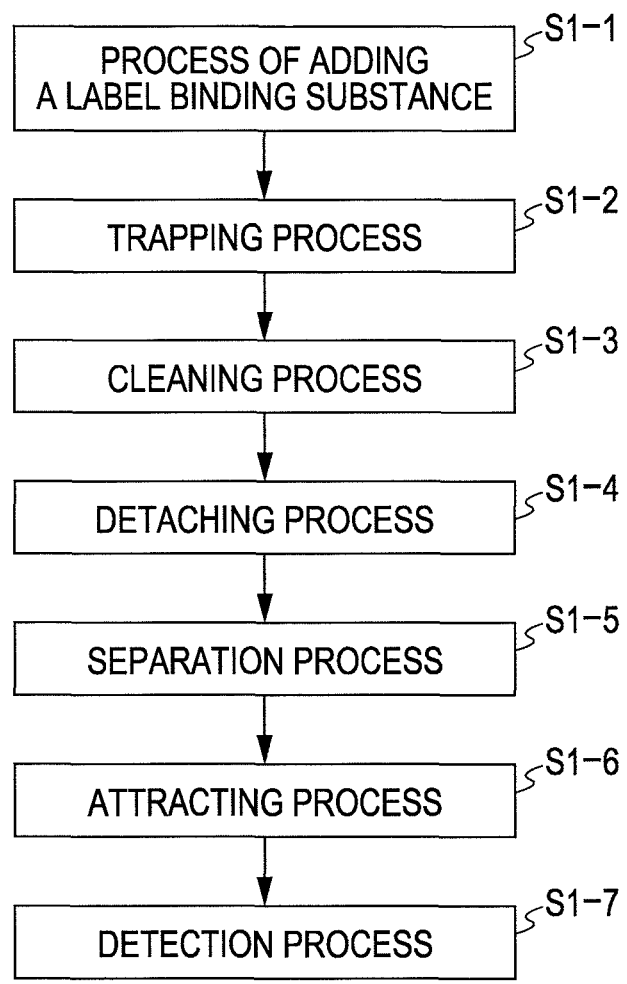
FIG. 22 shows a flow chart of the procedure of the method for electrochemically detecting an analyte according to one embodiment of the present invention.

The procedure of the method for electrochemically detecting an analyte [referred to as "a method 2"] according to one embodiment of the present invention is shown in FIG. 22. In the method for electrochemically detecting an analyte, the detector, the test chip, and the detection set as described above can be used, however, the present invention is not limited thereto.

In the method 2, a complex containing the labeling substance and the analyte is formed on the probe holding substrate outside of the working electrode. At least the label binding substance or the labeling substance is detached from the probe holding substrate, attracted to the working electrode, and detected. Therefore, according to the method 2, the analyte can be detected regardless of the size of the analyte.

In the method 2, as the probe holding substrate in the process (2-1), the probe holding substrate in which the probe for trapping the analyte or the label binding substance are held on the substrate body through the holder can be used.

In the method 2, the working electrode is opposed to the probe holding substrate through a predetermined gap after the process (2-1) and the process (2-2) may be performed. The processes (2-1) to (2-3) may be performed in a state where the electrode substrate including the working electrode and the probe holding substrate are arranged so as to be opposed to each other.

In the method 2, an electrochemically or photochemically active substance is used as the labeling substance.

The method 2 is different from the method 1 in the addition of a label binding substance obtained by labeling a binding substance for trapping an analyte with a labeling substance to the analyte ["a process of adding a label binding substance S1-1" in FIG. 22], the detachment of the complex containing the labeling substance and the analyte from the probe holding substrate, and the separation of the label binding substance or the labeling substance ["a separation process S1-5" in FIG. 22].

The labeling substance, the attractive modulator, the attracting liquid, the working electrode, and the electrolytic solution which are used for the method 2 are the same as those used for the method 1.

In the method 2, the analyte is brought into contact with the label binding substance to add the label binding substance to the analyte ["the process of adding a label binding substance S1-1" in FIG. 22]. In the process of adding a label binding substance S1-1, a complex containing the analyte and the label binding substance is formed. In this case, the label binding substance is not bound to impurities other than the analyte.

The process of adding the label binding substance (target substance containing a labeling substance) to the analyte can be performed under conditions where the binding substance contained in the label binding substance is bound to the analyte. The conditions where the binding substance is bound to the analyte can be suitably selected depending on the type of the analyte.

For example, when the analyte is a nucleic acid, the process of adding the label binding substance to the analyte can be performed in a solution such as phosphate-buffered saline. The process of adding the label binding substance to the analyte can be performed in, for example, a microtube (e.g. an Eppendorf tube).

When the analyte is a nucleic acid, the nucleic acid which contains a recognition sequence that can be cleaved by a restriction enzyme in a portion that is not involved in the trapping of the analyte and has the labeling substance bounded (also referred to as a "cleavable nucleic acid") can be used as the label binding substance. In this case, at least the labeling substance can be easily separated by using the restriction enzyme in the separation process to be described later.

When the analyte is a nucleic acid and the nucleic acid is contained in the label binding substance, a conjugate of the label binding substance and the analyte (a complex containing the labeling substance and the analyte) may be heated in the separation process to be described later. Thus, at least the labeling substance can be easily separated.

In the method 2, the complex containing the labeling substance and the analyte is brought into contact with the probe holding substrate to form the complex containing the labeling substance and the analyte on the probe holding substrate ["a trapping process S1-2" in FIG. 22].

Then, the probe holding substrate is cleaned ["a cleaning process S1-3" in FIG. 22].

Thereafter, at least the label binding substance or the labeling substance which is trapped on the holder is detached from the holder of the probe holding substrate ["a detaching process S1-4" in FIG. 22].

The trapping process S1-2, the cleaning process S1-3, and the detaching process S1-4 in the method 2 are the same as those in the method 1.

Thereafter, at least the label binding substance or the labeling substance is separated from the complex containing the labeling substance and the analyte ["a separation process S1-5" in FIG. 22].

In the separation process, as for the separation of at least the label binding substance or the labeling substance from the complex containing the labeling substance and the analyte, the target substance containing a labeling substance is separated by a separation method according to the type of the label binding substance used in the process of adding the label binding substance.

For example, when the analyte is a nucleic acid and a labeling substance obtained by modifying the nucleic acid having a sequence complementary to the analyte is used, the label binding substance or the labeling substance can be separated depending on the amount of the analyte by heating the solution containing the complex.

When the cleavable nucleic acid is contained in the label binding substance, the label binding substance or the labeling substance can be separated depending on the amount of the analyte by cutting the recognition sequence in the cleavable nucleic acid with a restriction enzyme.

Then, at least the label binding substance or the labeling substance is attracted to the working electrode in which the label binding substance or a trapping substance for trapping the labeling substance is not present ["an attracting process S1-6" in FIG. 22].

Thereafter, the label binding substance or the labeling substance which has been attracted to the working electrode is electrochemically detected ["a detection process S1-7" in FIG. 22].

The attracting process S1-6 and the detection process S1-7 in the method 2 are the same as those in the method 1.

As described above, when the nucleic acid is contained in the label binding substance, a solution to be used for the extraction and purification of nucleic acid (e.g. trade name: PB buffer, manufactured by QIAGEN) can be used in the attracting process. In this case, the solution is first added to the liquid phase recovered in the separation process. As a result, at least the label binding substance or the labeling substance can be attracted to near the working electrode.

When the analyte is substances other than nucleic acids, a nucleic acid may be used as the labeling substance or the attractive modulator. Accordingly, the analyte can be simply detected in the same manner as described above.

The method for electrochemically detecting an analyte of the present invention includes a method of electrochemically detecting an electrochemically or photochemically active analyte, including:

(3-1) bringing an analyte into contact with a probe holding substrate in which a probe for trapping the analyte is held on the substrate body to allow the analyte to be trapped by the probe;

(3-2) detaching the analyte or a part of the analyte trapped by the probe from the holder of the probe holding substrate in the process (3-1) and attracting to a working electrode in which the analyte or a trapping substance for trapping the part of the analyte is not present; and (3-3) electrochemically detecting the analyte or the part of the analyte which has been attracted to the working electrode in the process (3-2) [referred to as a method 3].

Also in the method 3, as the probe holding substrate in the process (3-1), the probe holding substrate in which the probe for trapping the analyte is held on the substrate body through the holder can be used.

In the method 3, the working electrode is opposed to the probe holding substrate through a predetermined gap after the process (3-1) and the process (3-2) may be performed. The processes (3-1) to (3-3) may performed in a state where the electrode substrate including the working electrode and the probe holding substrate are arranged so as to be opposed to each other.

In the method 3, for example, when the analyte is a nucleic acid and the probe contains the nucleic acid, the analyte is trapped on the probe holding substrate by bringing a liquid sample containing the analyte into contact with the probe holding substrate. Then, the analyte or a part of the analyte is separated by heating the obtained probe holding substrate or bringing into contact with the restriction enzyme. Thereafter, the analyte or a part of the analyte is detected by attracting them to near the working electrode using the attracting liquid and measuring the oxidation reduction current.

EXAMPLES

Hereinafter, the present invention will be described in detail with reference to Examples, however, the present invention is not limited thereto.

Preparation Example 1

Labeled thiolated DNA was produced by introducing a thiol group and a labeling substance (Alexa Fluor750) to DNAs of 24 nucleotides. The labeled thiolated DNA was dispersed in sterile purified water at a concentration of 1 µM and a DNA aqueous solution (A) was obtained. A DNA aqueous solution (B) was obtained by operating in the same manner as described above except that only the thiol group was introduced into DNAs of 24 nucleotides.

Preparation Example 2

Acetonitrile (AN) was mixed with ethylene carbonate (EC) at a volume ratio of 2:3 (AN:EC). Tetrapropylammonium iodide as an electrolyte salt was dissolved in the resulting mixed liquid at a concentration of 0.6 M. Thereafter, iodine as an electrolyte was dissolved in the resulting mixed liquid at a concentration of 0.06 M. The mixed liquid thus obtained was used as a solution for etching of gold thin films or nanoparticles, a solution for attracting labeled objects to a working electrode or an electrolytic solution in the following tests.

Test Example 1

(1) Production of DNA Holding Substrate

A platinum thin film (thickness: about 170 nm) as an adhesion layer 361$a$ for forming a holder 361 was formed on the surface of substrate bodies 330$a$ and 331$a$ composed of glass ($SiO_2$) by the spattering method. Further, a gold thin film (thickness: about 2 nm) as a holding layer 361$b$ for forming the holder 361 which could be etched was formed on the adhesion layer 361$a$ by the vacuum evaporation.

Then, the labeled thiolated DNA or thiolated DNA was covalently-bonded to the gold of the gold thin film by immersing the substrate bodies 330$a$ and 331$a$ having the holders 361 (referred to as "film forming substrates") in the DNA aqueous solution (A) (Test No. 1) or the DNA aqueous solution (B) (Test No. 2) for approximately 14 hours. Thereafter, the obtained film forming substrates were washed with water and dried. Thus, a DNA holding substrate 330 of Test No. 1 and a DNA holding substrate 331 of Test No. 2 were obtained [see FIG. 23 (A)]. In FIG. 23 (A), the labeled thiolated DNA and the thiolated DNA are omitted.

(2) Production of Working Electrode Substrate

A working electrode 351 composed of a thin film (about 200 nm in thickness) formed of indium oxide containing tin was formed on the surface of the substrate body 320$a$ composed of glass ($SiO_2$) by the spattering method. Thus, a working electrode substrate 320 was obtained [see FIG. 23 (B)]. A thin film formed of indium oxide containing tin oxide as a dopant (hereafter simply referred to as "indium oxide containing tin") serves both as the conductive layer and the electron accepting layer.

(3) Substrate Having Counter Electrode and Reference Electrode (Counter Electrode Substrate)

A counter electrode 352 composed of a platinum thin film and a reference electrode 353 composed of a platinum thin film were formed on the surface of a substrate body 370$a$ composed of glass ($SiO_2$) by the spattering method. Thus, a counter electrode substrate 370 was obtained [see FIG. 23 (C)].

(4) Detachment of Labeled DNA and Attraction of Labeled DNA Onto Working Electrode A region about 1 $mm^2$ on the working electrode 351 of the working electrode substrate 320 was surrounded by silicone rubber (100 µm in thickness) of the spacer 340. 7 µL of a solution was poured into the space formed with the silicone rubber 340.

Then, the space was sealed with the DNA holding substrate 330 or the DNA holding substrate 331 from the upper side of the working electrode substrate 320 and an assembly was formed. Thereafter, the working electrode substrate 320 of the assembly was made to be located on the lower side, and the assembly was allowed to stand at room temperature for 30 minutes [see FIG. 23 (D)]. In this case, the gold thin film of the DNA holding substrate 330 was etched with iodine contained in the electrolytic solution. Thus, the labeled thiolated DNA (Test No. 1) or the thiolated DNA (Test No. 2) were detached from the DNA holding substrate 330 or the DNA holding substrate 331. The labeled thiolated DNA or thiolated DNA was allowed to be attracted to near the working electrode 351 by tetrapropylammonium iodide (supporting electrolyte salt) and iodine (electrolyte) contained in the solution.

Thereafter, the DNA holding substrate was removed from the assembly. The solution remained on the working electrode 351 was removed by washing with dehydrated ethanol.

(5) Measurement of Photocurrent

The working electrode 351 of the working electrode substrate 320 after performing the process of (4) above was surrounded by silicone rubber (200 µm in thickness) of the spacer 340. 11.1 µL of electrolytic solution was poured into the space formed with the silicone rubber.

Figure 24:
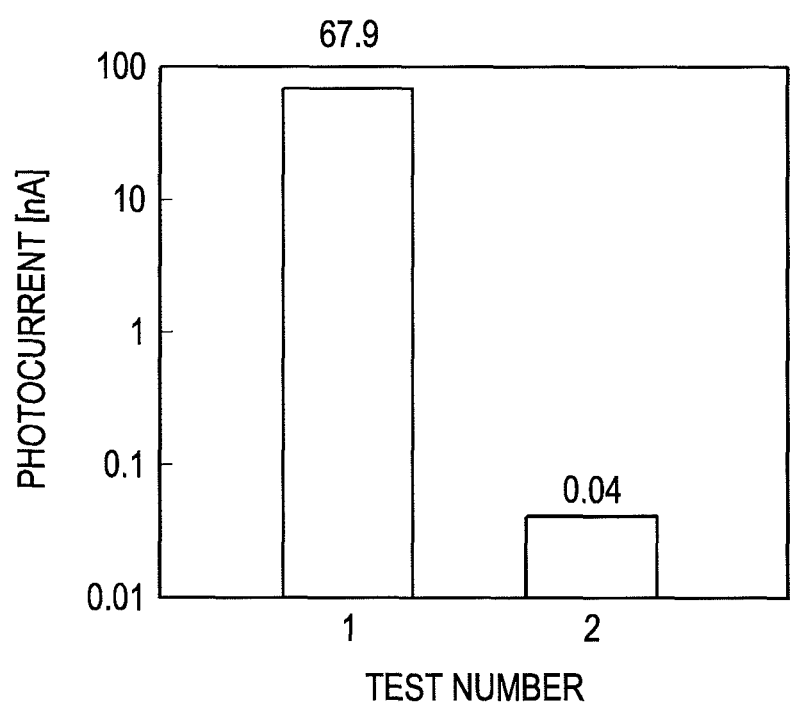
FIG. 24 is a graph showing examined results of a relationship between the type of the DNA holding substrate and photocurrent used in Test example 1.

Then, the space was sealed with the counter electrode substrate 370 from the upper side of the working electrode substrate 320. Thus, the working electrode 351, the counter electrode 352, and the reference electrode 353 were brought into contact with the electrolytic solution. A voltage was applied to the working electrode 351 so that the potential of the working electrode 351 was equal to that of the reference electrode 353 At the same time, laser light (wavelength: about 785 nm, intensity: about 13 mW) was emitted from the opposite side of the surface in contact with the electrolytic solution of the working electrode 351 [see FIG. 23 (E)]. In this case, predetermined positions (laser light irradiation positions 1 to 6) on the working electrode 351 were irradiated with laser light while blinking the laser light at a predetermined cycle (1 Hz) (on-off) [see FIG. 23 (F)]. A photocurrent (A) generated between the working electrode 351 and the counter electrode 352 by illuminating the laser light (when the light was on) was measured by averaging the photocurrent after blinking the laser light 20 times. FIG. 24 shows the photocurrents measured in Test example 1. The photocurrents shown in FIG. 24 were obtained by averaging photocurrents detected at the irradiation positions 1 to 6.

From the results shown in FIG. 24, it is found that the photocurrent derived from the labeling substance was detected in Test No. 1 where the labeling substance was used. From these results, it is found that the detachment of DNA (analyte) from the DNA holding substrate, the attraction of DNA to the working electrode 351 of the working electrode substrate 320, the electrochemical detection are well performed.

From these results shown in FIG. 24, it is found that the photocurrent in the case (Test No. 1) where the labeling substance was used was significantly increased as compared with the photocurrent in the case (Test No. 2) where the labeling substance was not used. Therefore, these results show that the photocurrent based on the labeling substance can be well detected.

Test Example 2

Effects of the type of the holder on the dissolution of the holder, the detachment of DNA, the attraction of DNA to the working electrode, and the detection of DNA were examined.

(1) Production of DNA Holding Substrate

The holding layer 361$b$ [gold thin film (thickness: about 2 nm)] which could be etched as the holder 361 was formed on the surface of a substrate body 332a composed of glass (SiO₂) by the vacuum evaporation (Test No. 3).

A platinum thin film (thickness: about 170 nm) as an adhesion layer 361a for forming the holder 361 was formed on the surface of the substrate body 332a composed of glass (SiO₂) by the spattering method. Further, a gold thin film (thickness: about 2 nm) as the holding layer 361b for forming the holder 361 which could be etched was formed on the adhesion layer 361a by the vacuum evaporation (Test No. 4).

Then, the labeled thiolated DNA was covalently-bonded to the gold of the gold thin film by immersing the obtained film forming substrates in the DNA aqueous solution (A) for about 14 hours. Thereafter, the obtained film forming substrates were washed with water and dried. Thus, a DNA holding substrate 332 of Test No. 3 [see FIG. 25 (A)] and a DNA holding substrate 333 of Test No. 4 [see FIG. 25 (B)] were obtained. In FIGS. 25 (A) and (B), the labeled thiolated DNA is not shown.

(2) Production of Working Electrode Substrate

The working electrode 351 composed of a thin film (about 200 nm in thickness) formed of indium oxide containing tin was formed on the surface of the substrate body 320a composed of glass (SiO₂) by operating in the same manner as described in Test example 1 (2). Thus, the working electrode substrate 320 was obtained [see FIG. 25 (C)].

(3) Production of Substrate (Counter Electrode Substrate) Having Counter Electrode and Reference Electrode The counter electrode 352 composed of a platinum thin film and the reference electrode 353 composed of a platinum thin film were formed on the substrate body 370a by operating in the same manner as Test example 1 (3). Thus, the counter electrode substrate 370 was obtained [see FIG. 25 (D)].

(4) Detachment of Labeled DNA and Attraction of Labeled DNA Onto Working Electrode An assembly was produced using a solution, the DNA holding substrate 332 [see FIG. 25 (A)] or the DNA holding substrate 333 obtained in (1) above [see FIG. 25 (B)], and the working electrode substrate 320 obtained in (2) above in the same manner as described in Test example 1 (4).

Then, the labeled thiolated DNA was detached from the DNA holding substrate 332 or the DNA holding substrate 333 by operating in the same manner as Example 1 (4) and it was allowed to be attracted to near the working electrode 351 [see FIGS. 25 (E) and (F)]. FIG. 25 (E) shows a state of an assembly with the DNA holding substrate 332 when detaching and attracting the labeled thiolated DNA. FIG. 25 (F) shows a state of an assembly with the DNA holding substrate 333 when detaching and attracting the labeled thiolated DNA.

Thereafter, the DNA holding substrate 332 or 333 was removed from the assembly. The solution remained on the working electrode 351 was removed by washing with dehydrated ethanol.

(5) Measurement of Photocurrent

The photocurrent was measured by operating in the same manner as described in Test example 1 (5). It's confirmed whether the photocurrent was detectable or not. The results are shown in Table 1. The evaluation criteria are as follows:

<Evaluation Criteria>

"Excellent": a photocurrent value obtained when using the labeled thiolated DNA is more than a numerical value calculated by adding a value twice the variation (standard deviation) to a photocurrent value obtained when using the thiolated DNA; and "Unacceptable": the photocurrent value obtained when using the labeled thiolated DNA is less than the numerical value calculated by adding the value twice the variation (standard deviation) to the photocurrent value obtained when using the thiolated DNA.

TABLE 1

| Test Number | Detection of photocurrent |
| --- | --- |
| 3 | Excellent |
| 4 | Good |

From the results shown in Table 1, it is found that the photocurrent could be well detected when either the DNA holding substrate 332 (Test No. 3) with the holder 361 composed of only the holding layer 361b (gold thin film) or the DNA holding substrate 333 (Test No. 4) with the holder 361 composed of the adhesion layer 361a (platinum thin film) and the holding layer 361b (gold thin film) was used.

Test Example 3

It was investigated whether operations of detaching labeled DNA from the DNA holding substrate, attracting labeled DNA onto the working electrode, and detecting the photocurrent could be performed by a series of operations (one step) without replacing a solution in a space on the working electrode.

(1) Production of DNA Holding Substrate

The DNA holding substrate 332 [see FIG. 26 (A)] and the DNA holding substrate 333 [see FIG. 26 (B)] were obtained by operating in the same manner as Test example 2 (1) except that the thickness of gold thin film was set to 5.1 nm in Test example 2 (1). The DNA holding substrate 332 shown in FIG. 26 (A) is a substrate in which the holding layer 361b (gold thin film) which can be etched is formed as the holder 361 on the substrate body 332a. The DNA holding substrate 333 shown in FIG. 26 (B) is a substrate in which the adhesion layer 361a (platinum thin film) and the holding layer 361b (gold thin film) are formed in this order as the holder 361 on a substrate body 333a. In FIGS. 26 (A) and (B), the labeled thiolated DNA is not shown.

(2) Production of Electrode Substrate Having Working Electrode, Counter Electrode, and Reference Electrode The working electrode 351 formed of a thin film composed of indium oxide containing tin (about 200 nm in thickness) was formed on the surface of a substrate body 321a composed of glass (SiO₂) so as to have a pattern shown in FIG. 26 (C) by the spattering method. Further, the counter electrode 352 composed of a platinum thin film and the reference electrode 353 composed of a platinum thin film were formed on the surface of the same substrate body 321a with the working electrode 351 formed so as to have a pattern shown in FIG. 26 (C) by the spattering method. Thus, an electrode substrate 321 was obtained [see FIG. 26 (C)].

(3) Detachment of Labeled DNA, Attraction of Labeled DNA onto Working Electrode, and Measurement of Photocurrent A region about 1 mm² on the working electrode 351 of the electrode substrate 321 was surrounded by silicone rubber (50 μm in thickness) of the spacer 340. 3.5 μL of solution was charged into the space formed with the silicone rubber.

Then, the space was covered with the DNA holding substrate 332 or the DNA holding substrate 333 from the upper side of the electrode substrate 321, and a test chip 310 or a test chip 311 was formed. Thereafter, the electrode substrates 321 of the test chips 310 and 311 were made to be located on the lower side, and then the test chips 310 and 311 were allowed to stand at room temperature for 30 minutes [see FIGS. 26 (D) and (E)]. As a result, the labeled thiolated DNA was detached from the DNA holding substrate 332 or the DNA holding substrate 333 and it was allowed to be attracted to near the working electrode. FIG. 26 (D) shows a state of the test chip 310 with the DNA holding substrate 332 when detaching and attracting the labeled thiolated DNA. FIG. 26 (E) shows a state of the test chip 311 with the DNA holding substrate 333 when detaching and attracting the labeled thiolated DNA.

Figure 27:
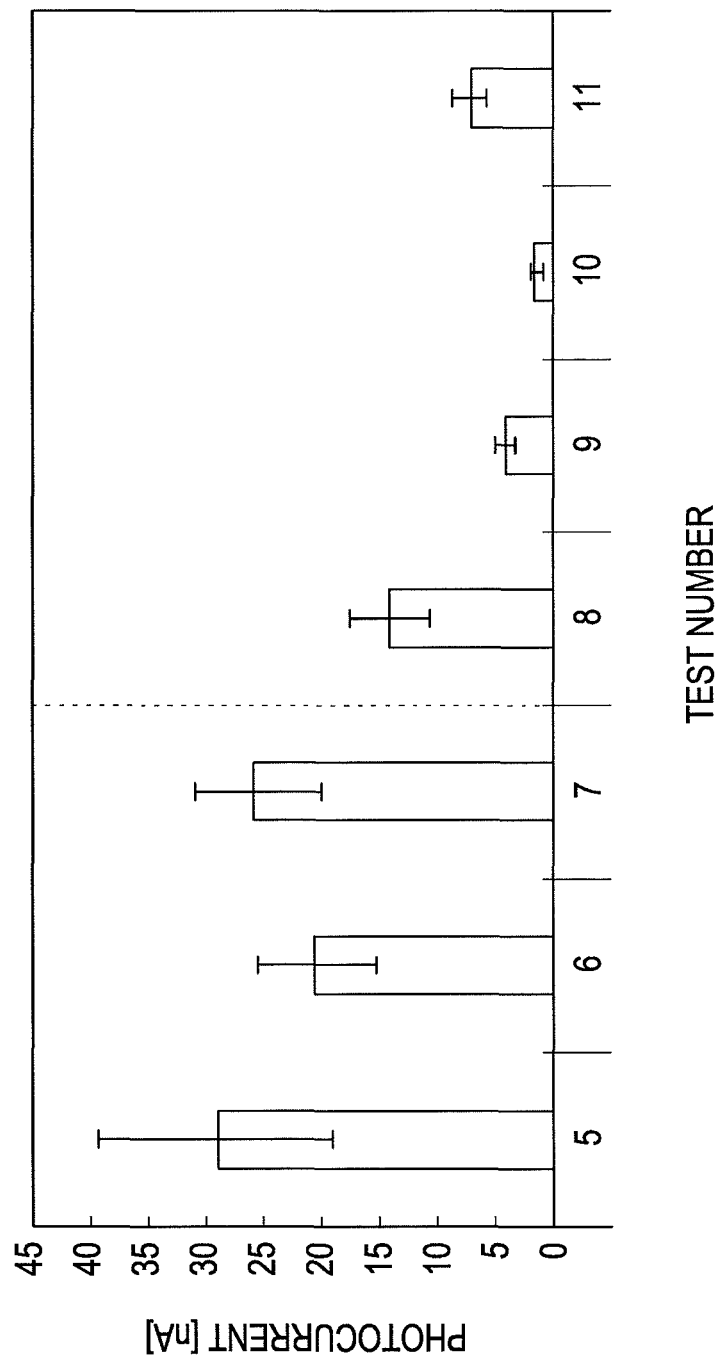
FIG. 27 is a graph showing examined results of a relationship between the type of the DNA holding substrate and photocurrent used in Test example 3.
Figure 28C:
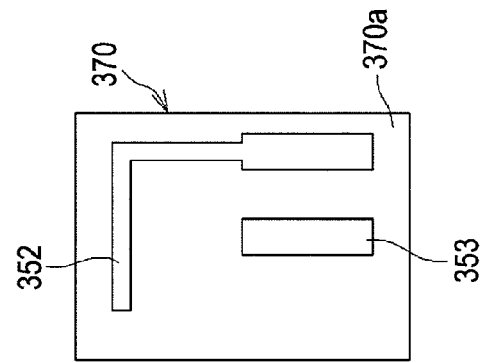
FIG. 28 (A) is a plane explanatory view showing the DNA holding substrate used in Test example 4.
Figure 28B:
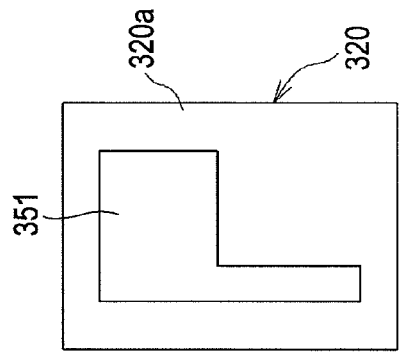
Figure 28E:
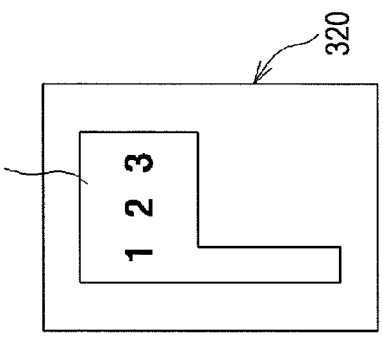
Figure 28A:
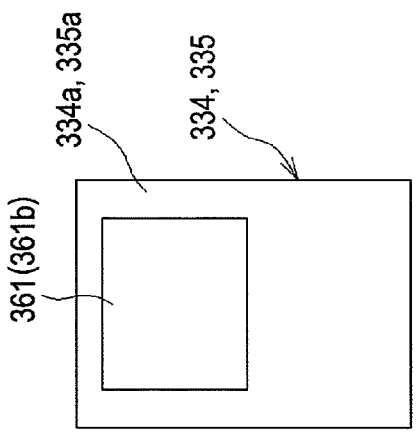
Figure 28D:
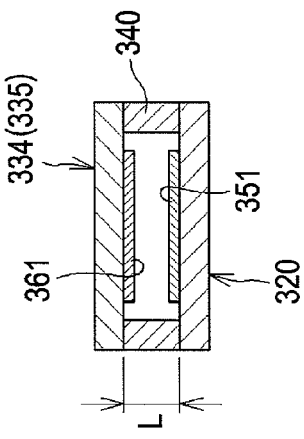

Thereafter, laser light (wavelength: about 785 nm, intensity: about 13 mW) was illuminated from the electrode substrate 321 of each assembly [see FIG. 26 (F)]. In this case, predetermined positions (laser light irradiation positions 1 to 6) on the working electrode 351 were irradiated with laser light while blinking the laser light at a predetermined cycle (1 Hz) (on-off) [see FIG. 26 (G)]. The photocurrent (A) generated between the working electrode 351 and the counter electrode 352 at the time of lighting the laser light (when the light was on) after blinking the laser light 20 times was measured. FIG. 27 shows examined results of a relationship between the type of the DNA holding substrate and photocurrent used in Test example 3. In FIG. 27, the photocurrent shows an average value of the photocurrents (A) when the laser light irradiation positions 1 to 6 were irradiated with laser light.

In the drawing, Test Nos. 5 to 7 indicate an average value of the photocurrents obtained from three different test chips when the DNA holding substrate 332 [see FIG. 26 (A)] having the holder 361 composed only of the holding layer 361b (gold thin film) was used. Here, Test No. 5 is an average value of the photocurrents obtained by measuring three points on the first test chip, Test No. 6 is an average value of the photocurrents obtained by measuring three points on the second test chip, and Test No. 7 is an average value of the photocurrents obtained by measuring three points on the third test chip [see FIG. 26 (F)]. In the drawing, Test Nos. 8 to 11 indicate an average value of the photocurrents obtained from four different test chips when the DNA holding substrate 333 [see FIG. 26 (B)] having the holder 361 composed of the adhesion layer 361a (platinum thin film) and the holding layer 361b (gold thin film) was used. Here, Test No. 8 is an average value of the photocurrents obtained by measuring three points on the first test chip, Test No. 9 is an average value of the photocurrents obtained by measuring three points on the second test chip, Test No. 10 is an average value of the photocurrents obtained by measuring three points on the third test chip, and Test No. 11 is an average value of the photocurrents obtained by measuring three points on the fourth test chip.

From the results shown in FIG. 27, it is found that the photocurrent can be well detected when the test chips 310 and 311 composed of the DNA holding substrate 332 or the DNA holding substrate 333, the silicone rubber 340, the electrode substrate 321 having the working electrode 351, the counter electrode 352, and the reference electrode 353 are used. From these results, it is found that when the test chips 310 and 311 are used, the process can be performed by a series of operations (one step) without replacing a solution in a space on the working electrode 351.

Test Example 4

A relationship of the gap length between the DNA holding substrate and the working electrode substrate and the photocurrent was examined.

(1) Production of DNA Holding Substrate

The holding layers 361b [gold thin film (thickness: about 2 nm)] which could be etched as the holders 361 were formed on the surfaces of substrate bodies 334a and 335a composed of glass ($SiO_2$) by the vacuum evaporation.

Then, the labeled thiolated DNA or the thiolated DNA was covalently-bonded to the gold of the gold thin films by immersing the obtained film forming substrates in the DNA aqueous solution (A) or the DNA aqueous solution (B) for about 14 hours. Thereafter, the obtained film forming substrates were washed with water and dried. Thus, a DNA holding substrate 334 or a DNA holding substrate 335 was obtained [see FIG. 28 (A)]. In FIG. 28 (A), the labeled thiolated DNA and the thiolated DNA are not shown.

(2) Production of Working Electrode Substrate

The working electrode 351 composed of a thin film (about 200 nm in thickness) formed of indium oxide containing tin was formed on the substrate body 320a by operating in the same manner as described in Test example 1 (2). Thus, the working electrode substrate 320 was obtained [see FIG. 28 (B)].

(3) Production of Substrate (Counter Electrode Substrate) Having Counter Electrode and Reference Electrode The counter electrode 352 composed of a platinum thin film and the reference electrode 353 composed of a platinum thin film were formed on the substrate body 370a by operating in the same manner as Test example 1 (3). Thus, the counter electrode substrate 370 was obtained [see FIG. 28 (C)].

(4) Detachment of Labeled DNA and Attraction of Labeled DNA Onto Working Electrode The working electrode 351 of the working electrode substrate 320 obtained in (2) above was surrounded by a double-sided tape (a gap length L was 10 or 30 µm) or silicone rubber (the gap length L was 50 or 100 µm) of the spacer 340. Then, 0.7 µL (for 10 µm gap), 2.1 µL (for 30 µm gap), 3.5 µL (for 50 µm gap) or 7 µL (for 100 µm gap) of solution was poured into the space formed with the double-sided tape or silicone rubber and the working electrode substrate 320.

Then, the space was covered with the DNA holding substrate 334 or the DNA holding substrate 335 obtained in (1) above from the upper side of the working electrode 351 of the working electrode substrate 320 and an assembly was formed. Thereafter, the working electrode substrate 320 of the assembly was made to be located on the lower side, and the assembly was allowed to stand at room temperature for 30 minutes [see FIG. 28 (D)]. As a result, the labeled thiolated DNA or the thiolated DNA was detached from the DNA holding substrate 334 or the DNA holding substrate 335 and it was allowed to be attracted to near the working electrode 351.

Thereafter, the DNA holding substrate 334 or 335 was removed from the assembly. The solution remained on the working electrode 351 was removed by washing with dehydrated ethanol.

In order to examine the case of the gap length L was 0 µm, the operation was performed in the same manner as described above except that only drops of solution (0.2 µL) were put on the working electrode 351 of the working electrode substrate 320 without using the spacer 340.

(5) Measurement of Photocurrent

Figure 29:
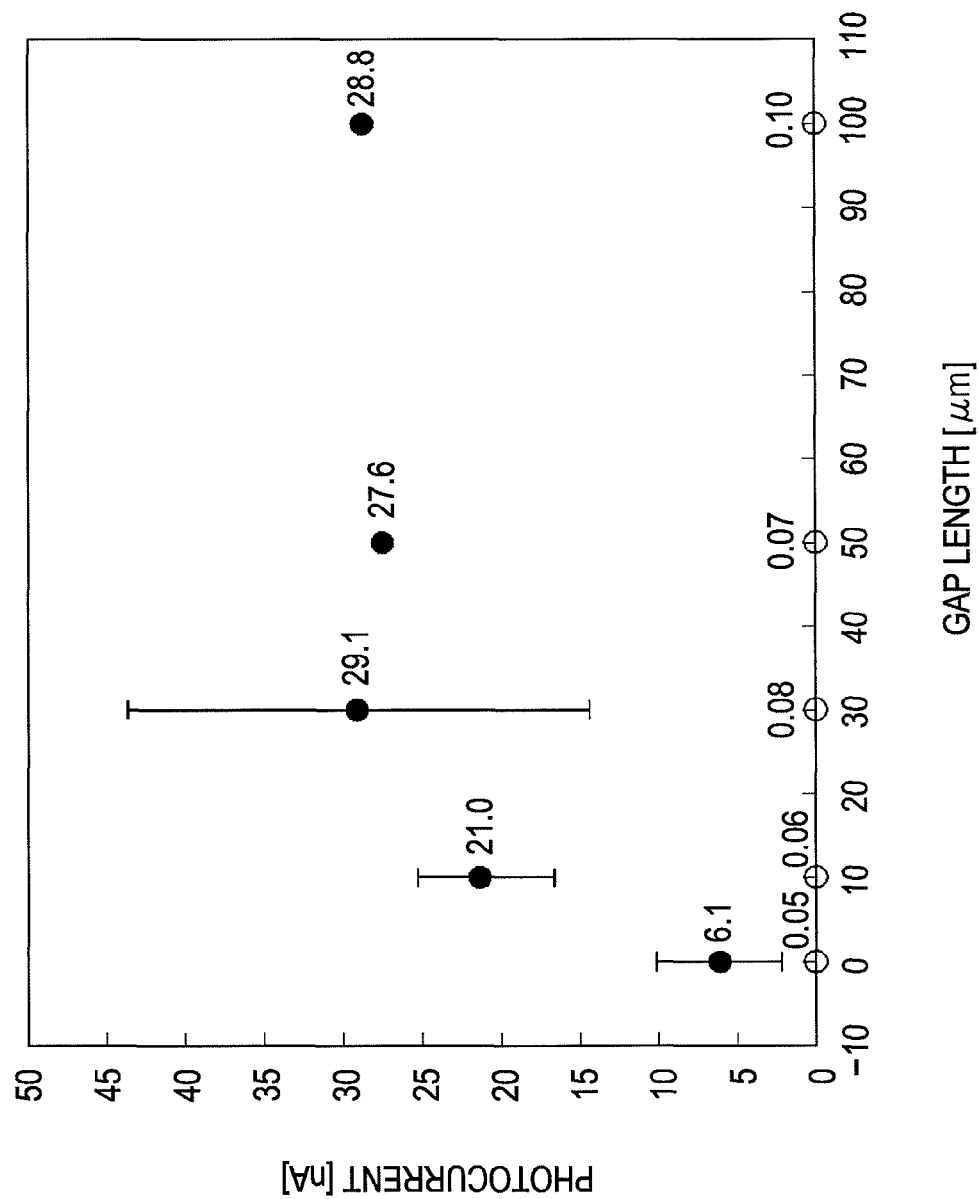
FIG. 29 is a graph showing examined results of a relationship between gap length and photocurrent in Test example 4.
Figure 30A:
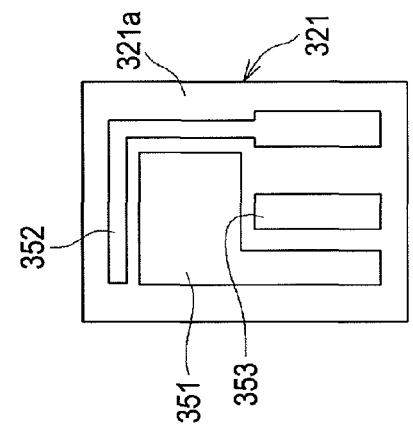
FIG. 30 (A) is a plane explanatory view showing the DNA holding substrate used in Test example 5.
Figure 30B:
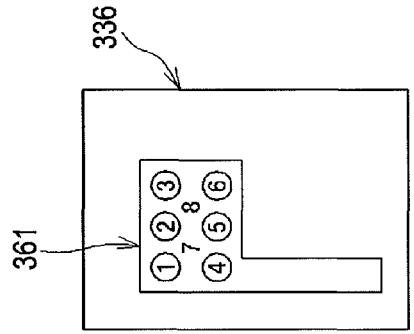
Figure 30C:
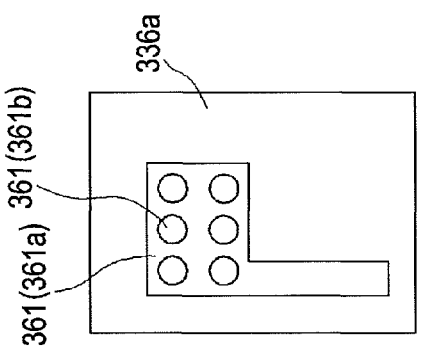
Figure 30D:
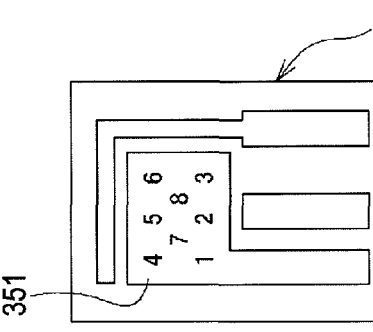
Figure 30E:
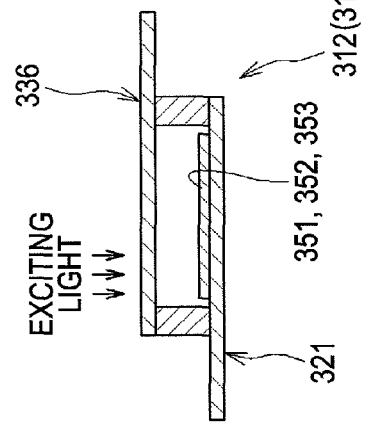
Figure 30F:
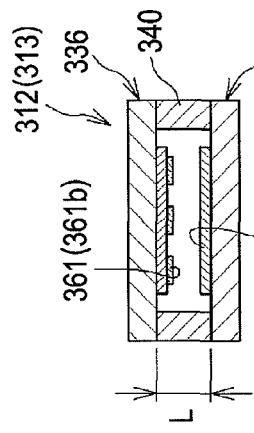
Figure 32A:
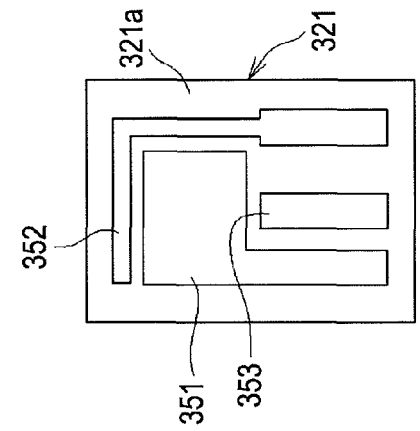
FIG. 32 (A) is a plane explanatory view showing the DNA holding substrate used in Test example 6.
Figure 32B:
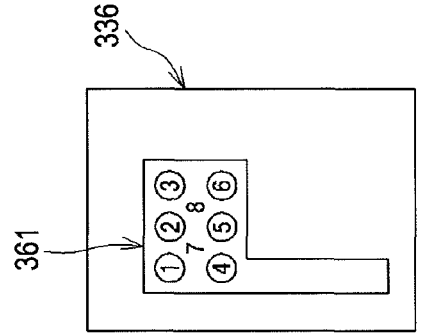
Figure 32C:
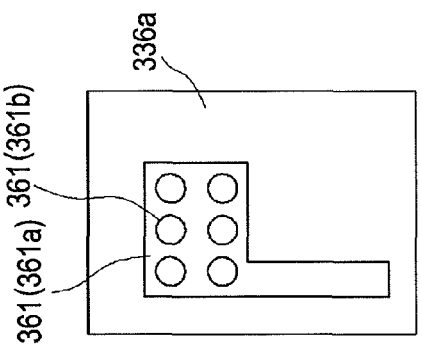
Figure 32D:
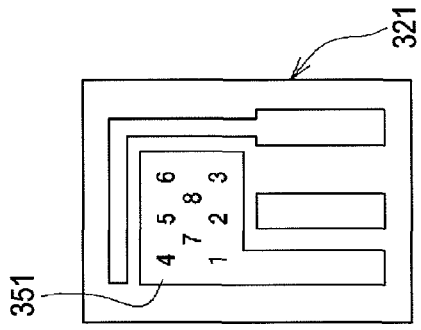
Figure 32E:
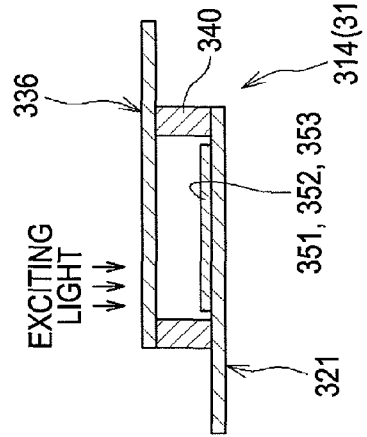
Figure 32F:
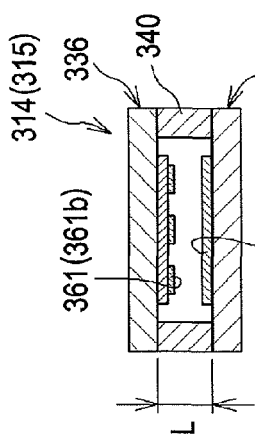

The working electrode 351 was irradiated with laser light by performing the operation in the same manner as described in Test example 1 (6) except that the laser light irradiation positions in Test example 1 (6) were used as the laser light irradiation positions 1 to 3 shown in FIG. 28 (E). The photocurrent (A) generated between the working electrode 351 and the counter electrode 352 was measured by averaging photocurrents for 20 s at each laser light irradiation position (corresponding to the 20 times' photocurrent measurements). FIG. 29 shows examined results of a relationship between gap length and photocurrent in Example 4. In FIG. 29, the photocurrent shows an average value of the photocurrents (A) when the laser light irradiation positions 1 to 3 were irradiated with laser light. In the drawing, filled circles indicate the results when the DNA holding substrate 334 for holding labeled thiolated DNA was used, and open circles indicate the results when the DNA holding substrate 335 for holding labeled DNA was used.

From the results shown in FIG. 29, it is found that the photocurrent exhibits nearly a constant value when the gap length between the working electrode substrate 320 and the DNA holding substrate 334 is 30 μm or more. Therefore, it is found that when the DNA holding substrate 334 is used, the gap length between the DNA holding substrate 334 and the working electrode substrate 320 is preferably from 30 to 100 μm from the viewpoint of well detecting the photocurrent.

Test Example 5

It was investigated whether various types of DNAs could be detected with one test chip when a plurality of DNA holding positions were provided and a plurality of laser light irradiation positions were set.

(1) Production of DNA Holding Substrate

A thin film (about 200 nm in thickness) composed of indium oxide containing tin as the adhesion layer 361a for forming the holder 361 was formed on the surface of a substrate body 336a composed of glass (SiO$_2$) by the spattering method. Six gold thin film spots (each thickness: about 2 nm) were formed as the holding layer 361b for forming the holder 361 on the thin film composed of indium oxide containing tin by the vacuum evaporation using a metal mask with six holes (1 mm in diameter) [FIG. 30 (A)].

Then, the labeled thiolated DNA was covalently-bonded to the gold of the gold thin film by immersing the obtained film forming substrate in the DNA aqueous solution (A) for about 14 hours. Thereafter, the obtained film forming substrate was washed with water and dried. Thus, a DNA holding substrate 336 was obtained [see FIG. 30 (B)]. In the drawing, the positions 7 and 8 are the site where labeled thiolated DNA is not present.

(2) Production of Electrode Substrate Having Working Electrode, Counter Electrode, and Reference Electrode The working electrode 351 formed of a thin film composed of indium oxide containing tin (about 200 nm in thickness) was formed on the surface of the substrate body 321a composed of glass (SiO$_2$) so as to have a pattern shown in FIG. 30 (C) by the spattering method. Further, the counter electrode 352 composed of a platinum thin film and the reference electrode 353 composed of a platinum thin film were formed on the surface of the same substrate body 321a with the working electrode 351 formed so as to have a pattern shown in FIG. 30 (C) by the spattering method. Thus, the electrode substrate 321 was obtained [see FIG. 30 (C)].

(3) Detachment of Labeled DNA, Attraction of Labeled DNA onto Working Electrode, and Measurement of Photocurrent A region about 1 mm$^2$ on the working electrode 351 of the electrode substrate 321 was surrounded by a double-sided tape (the gap length L was 10 μm, Test Nos. 12 to 19) or silicone rubber (the gap length L was 100 μm, Test Nos. 20 to 27) of the spacer 340. Then, 0.7 μL (for 10 μm gap) or 7 μL (for 100 μm gap) of solution was injected to the space formed with the double-sided tape or silicone rubber.

Then, the space was covered with the DNA holding substrate 336 from the upper side of the electrode substrate 321, and a test chip 312 (the gap length L was 10 μm) or a test chip 313 (the gap length L was 100 μm) was assembled [see FIG. 30 (D)]. Thereafter, the test chip 312 or 313 was allowed to stand at room temperature for 5 minutes. As a result, the holding layer 361b for holding the labeled thiolated DNA in the working electrode 351 of the electrode substrate 321 and the DNA holding substrate 336 were brought into contact with the solution.

A voltage was applied to the working electrode 351 so that the potential of the working electrode 351 was equal to that of the reference electrode 353. At the same time, laser light (wavelength: about 785 nm, intensity: about 13 mW) was illuminated to the working electrode 351 from the opposite side of the surface in contact with the electrolytic solution of the working electrode 351 [see FIG. 30 (E)]. In this case, predetermined positions (laser light irradiation positions 1 to 8) on the working electrode 351 were irradiated with laser light while blinking the laser light at a predetermined cycle (1 Hz) (on-off) [see FIG. 30 (F)]. The photocurrent (A) generated between the working electrode 351 and the counter electrode 352 was measured by averaging photocurrents for 20 s at each laser light irradiation position (corresponding to the times' photocurrent measurements). FIG. 31 shows examined results of a relationship between laser light irradiation position and photocurrent in Test example 5. In FIG. 31, the photocurrent shows an average value of the photocurrents (A) when the laser light irradiation positions 1 to 8 were irradiated with laser light. The laser light irradiation positions in FIG. 31 correspond to positions 1 to 8 in FIG. 30 (F).

From the results shown in FIG. 31, it is found that, in the case where the test chip 312 (the gap length L was 10 μm) was used (Test Nos. 12 to 19), the photocurrent generated when irradiating positions corresponding to sites where the gold thin film was formed on the DNA holding substrate 336 (the laser light irradiation positions 1 to 6, in the drawing) with light is larger than that generated when irradiating positions corresponding to sites where the gold thin film was not formed on the DNA holding substrate 336 (the laser light irradiation positions 7 and 8 in the drawing) with light. It is found that the same tendency was observed in the case where the test chip 313 (the gap length L was 100 μm) was used (Test Nos. 20 to 27). These results suggest that the pattern of labeled thiolated DNA held on the DNA holding substrate 336 is directly transferred to the working electrode 351. Therefore, it is found that various types of analytes can be detected at once by allowing different analytes to be trapped onto the substrate.

Test Example 6

A relationship of the gap length between the DNA holding substrate and the working electrode and the attraction efficiency was examined.

(1) Production of DNA Holding Substrate

A thin film (about 200 nm in thickness) composed of indium oxide containing tin as the adhesion layer 361a for forming the holder 361 was formed on the surface of a substrate body 336a composed of glass (SiO$_2$) by the spattering method. Six gold thin film spots (each thickness: about 2 nm) were formed as the holding layer 361b for forming the holder 361 on the thin film composed of indium oxide containing tin by the vacuum evaporation using a metal mask with six holes (1 mm in diameter) [see FIG. 32 (A)].

Then, the labeled thiolated DNA was covalently-bonded to the gold of the gold thin film by immersing the obtained film forming substrate in the DNA aqueous solution (A) for about 14 hours. Thereafter, the obtained film forming substrate was washed with water and dried. Thus, the DNA holding substrate 336 was obtained [see FIG. 32 (B)]. In the drawing, the positions 7 and 8 are the site where labeled thiolated DNA is not present.

(2) Production of Electrode Substrate Having Working Electrode, Counter Electrode, and Reference Electrode The working electrode 351 formed of a thin film composed of indium oxide containing tin (about 200 nm in thickness) was formed on the surface of the substrate body 321a composed of glass ($SiO_2$) so as to have a pattern shown in FIG. 32 (C) by the spattering method. Further, the counter electrode 352 composed of a platinum thin film and the reference electrode 353 composed of a platinum thin film were formed on the surface of the same substrate body 321a with the working electrode 351 formed so as to have a pattern shown in FIG. 32 (C) by the spattering method. Thus, the electrode substrate 321 was obtained [see FIG. 32 (C)].

(3) Detachment of Labeled DNA, Attraction of Labeled DNA onto Working Electrode, and Measurement of Photocurrent A region about 1 $mm^2$ on the working electrode 351 of the electrode substrate 321 was surrounded by a double-sided tape (the gap length L was 10 μm, Test Nos. 28 to 35) or silicone rubber (the gap length L was 100 μm, Test Nos. 36 to 43) of the spacer 340. Then, 0.7 μL (for 10 μm gap) or 7 μL (for 100 μm gap) of solution was poured to the space formed with the double-sided tape or silicone rubber.

Then, the space was covered with the DNA holding substrate 336 from the upper side of the electrode substrate 321, and a test chip 314 (the gap length L was 10 μm) or a test chip 315 (the gap length L was 100 μm) was assembled [see FIG. 32 (D)]. Thereafter, the test chip was allowed to stand at room temperature for 5 minutes. As a result, the holding layer 361b for holding the labeled thiolated DNA in the working electrode 351 of the electrode substrate 321 and the DNA holding substrate 336 were brought into contact with the solution.

Figure 33:
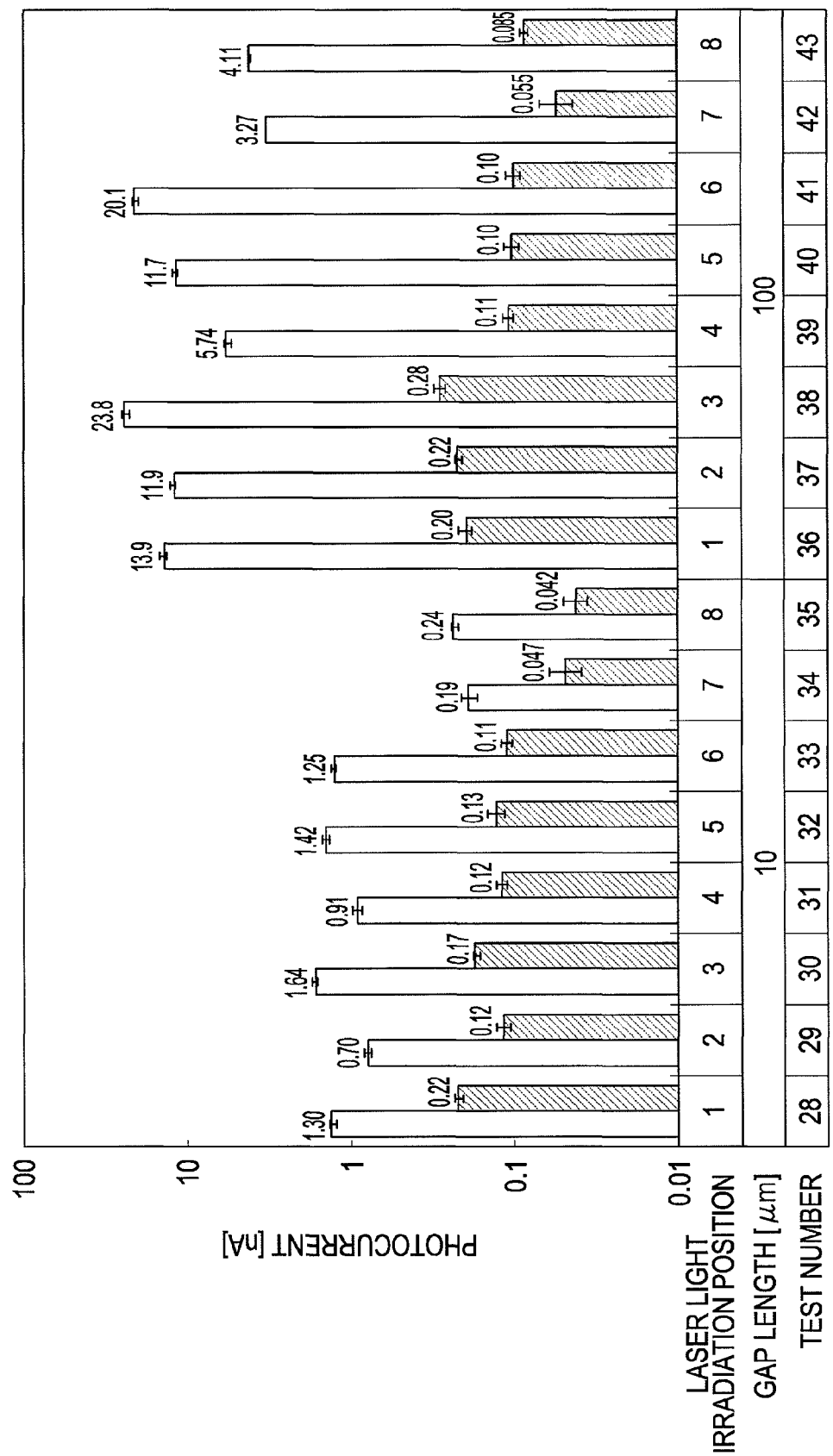
FIG. 33 is a graph showing examined results of a relationship among gap length, laser light irradiation position, and photocurrent in Test example 6.

A voltage was applied to the working electrode 351 so that the potential of the working electrode 351 was equal to that of the reference electrode 353. At the same time, laser light (wavelength: about 785 nm, intensity: about 13 mW) was illuminated to the working electrode 351 from the opposite side of the surface in contact with the electrolytic solution of the working electrode 351 [see FIG. 32 (E)]. In this case, predetermined positions (laser light irradiation positions 1 to 8) on the working electrode 351 were irradiated with laser light while blinking the laser light at a predetermined cycle (1 Hz) (on-off) [see FIG. 32 (F)]. The current value increased at the time of lighting laser light (when the light was on) was measured as the photocurrent. An average value of the photocurrents obtained by blinking the laser light 20 times at each of the laser light irradiation positions was measured. The current generated between the working electrode 351 and the counter electrode 352 under laser light illumination was the photocurrent (A), and the current generated between the DNA holding substrate 336 and the counter electrode 352 under laser light illumination was a photocurrent (B). FIG. 33 shows examined results of a relationship among gap length, laser light irradiation position, and photocurrent in Test example 6. The laser light irradiation positions in FIG. 33 correspond to positions 1 to 8 in FIG. 32 (F). White bars indicate an average value of the photocurrents (B) when the laser light irradiation positions 1 to 8 were irradiated with laser light. Shaded bars indicate an average value of the photocurrents (A) when the laser light irradiation positions 1 to 8 were irradiated with laser light.

Then, the attraction efficiency of the labeled thiolated DNA to the working electrode 351 was calculated based on the results shown in FIG. 33. The attraction efficiency was calculated using the following equation (I):

[Equation 1]

$$\text{Attraction efficiency} = \frac{\text{Photocurrent (A)}}{\text{Photocurrent (B)}} \times 100 \quad (1)$$

The results are shown in Table 2.

TABLE 2

| Test Number | Laser light irradiation position | Gap length (μm) | Attraction efficiency (%) |
|---|---|---|---|
| 28 | 1 | 10 | 17.0 |
| 29 | 2 | | 14.8 |
| 30 | 3 | | 10.4 |
| 31 | 4 | | 13.0 |
| 32 | 5 | | 9.2 |
| 33 | 6 | | 8.8 |
| 36 | 1 | 100 | 1.4 |
| 37 | 2 | | 1.8 |
| 38 | 3 | | 1.2 |
| 39 | 4 | | 1.8 |
| 40 | 5 | | 0.9 |
| 41 | 6 | | 0.5 |

From the results shown in Table 2, it is found that the attraction efficiency of labeled DNA to the working electrode 351 when the gap length L between the DNA holding substrate 336 and the electrode substrate 321 is 10 μm (Test Nos. 28 to 33) tends to be higher than the attraction efficiency of labeled DNA to the working electrode 351 when the gap length L is 100 μm (Test Nos. 36 to 41).

Example 1

(1) Production of Probe Holding Substrate

A thin film (about 2.4 nm in thickness) composed of palladium as the adhesion layer 361a for forming the holder 361 was formed on the surface of a substrate body 337a composed of glass ($SiO_2$) by the vacuum evaporation method. Further, a gold thin film (about 2.3 nm in thickness) as the holding layer 361b for forming the holder 361 was formed on the thin film composed of palladium by the vacuum evaporation method.

Then, the thiolated DNA was covalently-bonded to the gold of the gold thin film by immersing the obtained film forming substrate in the DNA aqueous solution (B) for about 14 hours. Thereafter, the obtained film forming substrate was washed with water and dried. Thus, a probe holding substrate 337 was obtained [see FIG. 34 (A)]. In FIG. 34 (A), the thiolated DNA is not shown.

(2) Production of Electrode Substrate Having Working Electrode, Counter Electrode, and Reference Electrode The working electrode 351 formed of a thin film composed of indium oxide containing tin (about 200 nm in thickness) was formed on the surface of the substrate body 321a composed of glass ($SiO_2$) so as to have a pattern shown in FIG. 34 (B) by the spattering method. Further, the counter electrode 352 composed of a platinum thin film and the reference electrode 353 composed of a platinum thin film were formed on the surface of the same substrate body 321a with the working electrode 351 formed so as to have a pattern shown in FIG. 34

(B) by the spattering method. Thus, the electrode substrate 321 was obtained [see FIG. 34 (B)].

(3) Preparation of Solution for Hybridization

DNA (analyte) was labeled with Alexa Fluor 750 and the target substance was obtained. A solution for hybridization was prepared by adding the target substance to a hybridization buffer (manufactured by Affymetrix) so that the concentration of DNA (analytes) was 10 nM and mixing them.

(4) Detection of Analyte

Silicone rubber (0.2 mm in thickness) was arranged around the probe holding substrate 337 so as to serve as a partition. 10 μL of solution for hybridization was poured to the space formed by the probe holding substrate 337 and the silicone rubber. A cover glass was placed on the silicone rubber not so as to make the solution for hybridization on the probe holding substrate 337 dried. Then, the probe holding substrate 337 was allowed to stand at 45° C. for 1.5 hours, and DNA and the DNA in the solution for hybridization on the probe holding substrate 337 were hybridized. Thereafter, the cover glass on the probe holding substrate 337 was removed. Subsequently, the probe holding substrate 337 was washed with a buffer for cleaning (trade name: Wash buffer A, manufactured by Affymetrix) and ultrapure water and air-dried.

A region about 1 mm$^2$ on the working electrode 351 of the electrode substrate 321 was surrounded by silicone rubber (100 μm in thickness) of the spacer 340. Thereafter, 7 μL of solution was poured into the space formed with the silicone rubber and the electrode substrate 321.

Then, the space was covered with the probe holding substrate 337 after hybridization reaction from the upper side of the electrode substrate 321 and an assembly was formed [see FIG. 34 (C)]. Thereafter, the assembly was allowed to stand at room temperature for 30 minutes. As a result, the holding layer 361*b* holding a complex containing the analyte and the thiolated DNA in the working electrode 351 of the electrode substrate 321 and the probe holding substrate 337 were brought into contact with the solution.

Thereafter, a voltage was applied to the working electrode 351 so that the potential of the working electrode 351 was equal to that of the reference electrode 353. At the same time, laser light (wavelength: about 785 nm, intensity: about 13 mW) was illuminated to the working electrode 351 from the opposite side of the surface in contact with the electrolytic solution of the working electrode 351 [see FIG. 34 (D)]. In this case, predetermined positions (laser light irradiation positions 1 to 6) on the working electrode 351 were irradiated with laser light while blinking the laser light at a predetermined cycle (1 Hz) (on-off) [see FIG. 34 (E)]. The photocurrent (A) generated between the working electrode 351 and the counter electrode 352 was measured by averaging photocurrents for 20 s at each laser light irradiation position (corresponding to the 20 times' photocurrent measurements).

The photocurrent (A) generated between the working electrode 351 and the counter electrode 352 was measured using a hybridization buffer [manufactured by Affymetrix] as a control (analyte concentration: 0 nM) in place of the solution for hybridization in the same manner as described above.

Figure 35:
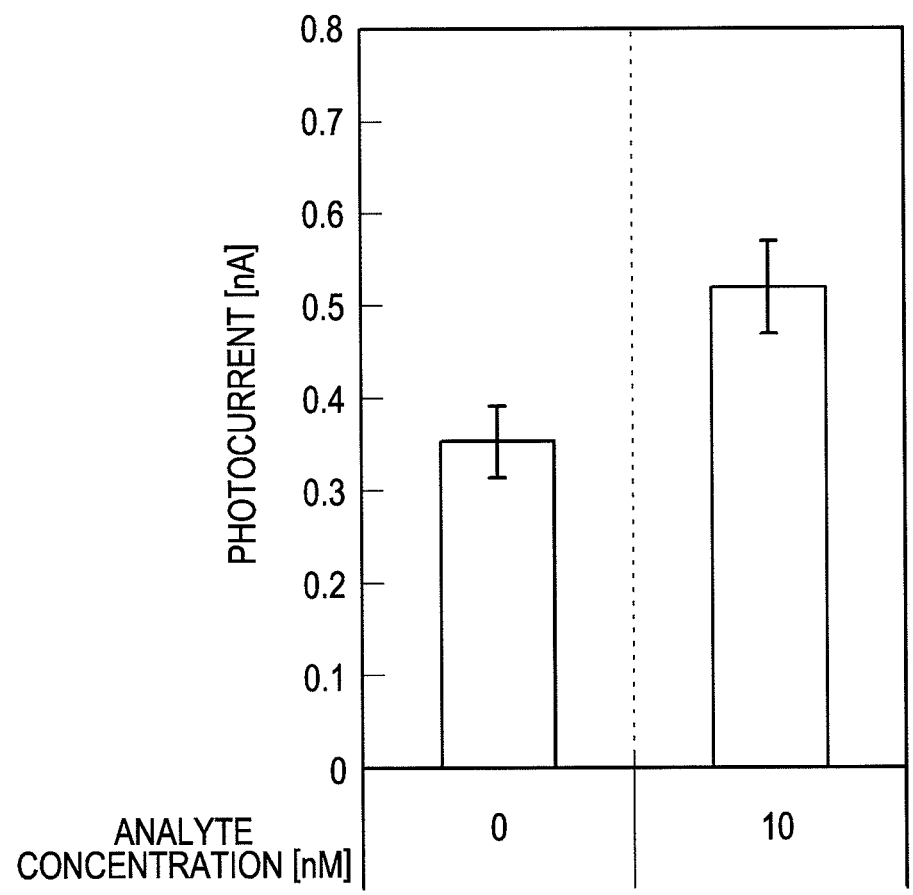
FIG. 35 is a graph showing examined results of a relationship between analyte concentration and photocurrent in Example 1.

FIG. 35 shows examined results of a relationship between analyte concentration and photocurrent in Example 1. A bar 1 indicates an average value of the photocurrents (A) at the time of irradiating the laser light irradiation positions 1 to 6 with laser light using the control (analyte concentration: 0 nM). A bar 2 indicates an average value of the photocurrents (A) at the time of irradiating the laser light irradiation positions 1 to 6 of the two electrode substrates with laser light using the solution for hybridization (analyte concentration: 10 nM).

From the results shown in FIG. 35, it is found that the photocurrent derived from the analyte can be detected by allowing the analyte to be trapped onto the probe holding substrate 337 and attracting it to the working electrode 351.

Example 2

(1) Production of Probe Holding Substrate

A thin film (about 200 nm in thickness) composed of indium oxide containing tin as the adhesion layer 361*a* for forming the holder 361 was formed on the surface of a substrate body 338*a* composed of glass (SiO$_2$) by the spattering method. Further, a gold thin film (about 2.1 nm in thickness) as the holding layer 361*b* for forming the holder 361 was formed on the thin film composed of indium oxide containing tin by the vacuum evaporation.

Then, the thiolated DNA was covalently-bonded to the gold of the gold thin film by immersing the obtained film forming substrate in the DNA aqueous solution (B) for about 48 hours. Thereafter, the obtained film forming substrate was washed with water and dried. Thus, a probe holding substrate 338 was obtained [see FIG. 36 (A)]. In FIG. 36 (A), the thiolated DNA is not shown.

(2) Production of Working Electrode Substrate

The working electrode 351 composed of a thin film (about 200 nm in thickness) formed of indium oxide containing tin was formed on the substrate body 320*a* by operating in the same manner as described in Test example 1 (2). Thus, the working electrode substrate 320 was obtained [see FIG. 36 (B)].

(3) Production of Substrate (Counter Electrode Substrate) Having Counter Electrode and Reference Electrode The counter electrode 352 composed of a platinum thin film and the reference electrode 353 composed of a platinum thin film were formed on the substrate body 370*a* by operating in the same manner as Test example 1 (2). Thus, the counter electrode substrate 370 was obtained [see FIG. 36 (C)].

(4) Preparation of Solution for Hybridization

DNA (analyte) was labeled with Alexa Fluor 750 and the target substance was obtained. Solutions for hybridization (Test Nos. 44 to 46) were prepared by adding the target substance to a hybridization buffer (manufactured by Affymetrix) so that the concentration of DNA (analyte) was 1 nM (Test No. 44), 10 nM (Test No. 45) or 100 nM (Test No. 46) and mixing them.

(5) Detection of Analyte

Silicone rubber (0.2 mm in thickness) was arranged around the probe holding substrate 338 so as to serve as a partition. 10 μL of solution for hybridization of Test Nos. 44 to 46 was poured to the space formed with the probe holding substrate 338 and the silicone rubber. A cover glass was placed on the silicone rubber not so as to make the solution for hybridization on the probe holding substrate 338 dried. Then, the probe holding substrate 338 was allowed to stand at 45° C. for 1.5 hours, and DNA and the DNA in the solution for hybridization on the probe holding substrate 338 were hybridized. Thereafter, the cover glass on the probe holding substrate 338 was removed. Subsequently, the probe holding substrate 338 was washed with a buffer for cleaning (trade name: Wash buffer A, manufactured by Affymetrix) and ultrapure water and air-dried.

A region about 1 mm$^2$ on the working electrode 351 of the working electrode substrate 320 was surrounded by silicone rubber (100 μm in thickness) of the spacer 340. 7 μL of solution was poured into the space formed with the silicone rubber.

Then, the space was sealed with the DNA holding substrate 338 after hybridization from the upper side of the working electrode substrate 320 and an assembly was formed. Thereafter, the working electrode substrate 320 of the assembly was made to be located on the lower side, and the assembly was allowed to stand at room temperature for 30 minutes [see FIG. 36 (D)]. As a result, the complex containing the analyte and the thiolated DNA was detached from the DNA holding substrate 338 and it was allowed to be attracted to near the working electrode 351.

Thereafter, the DNA holding substrate 338 was removed from the assembly. The solution remained on the working electrode 351 was removed by washing with dehydrated ethanol.

The working electrode 351 of the working electrode substrate 320 was surrounded by silicone rubber (200 μm in thickness) of the spacer 340. 11.1 μL of electrolytic solution was injected into the space formed with the silicone rubber.

Then, the space was sealed with the counter electrode substrate 370 from the upper side of the working electrode substrate 320. Thus, the working electrode 351, the counter electrode 352, and the reference electrode 353 were brought into contact with the electrolytic solution. A voltage was applied to the working electrode 351 so that the potential of the working electrode 351 was equal to that of the reference electrode 353. At the same time, laser light (wavelength: about 785 nm, intensity: about 13 mW) was emitted to the working electrode 351 from the opposite side of the surface in contact with the electrolytic solution of the working electrode 351 [see FIG. 36 (E)]. In this case, predetermined positions (laser light irradiation positions 1 to 3) on the working electrode 351 were irradiated with laser light while blinking the laser light at a predetermined cycle (1 Hz) (on-off) [see FIG. 36 (F)]. The photocurrent (A) flowing between the working electrode 351 and the counter electrode 352 at the time of lighting the laser light (when the light was on) after blinking the laser light 20 times was measured.

The photocurrent (A) generated between the working electrode 351 and the counter electrode 352 was measured using a hybridization buffer [manufactured by Affymetrix] as a control (analyte concentration: 0 nM) in place of the solution for hybridization in the same manner as described above.

Figure 37A:
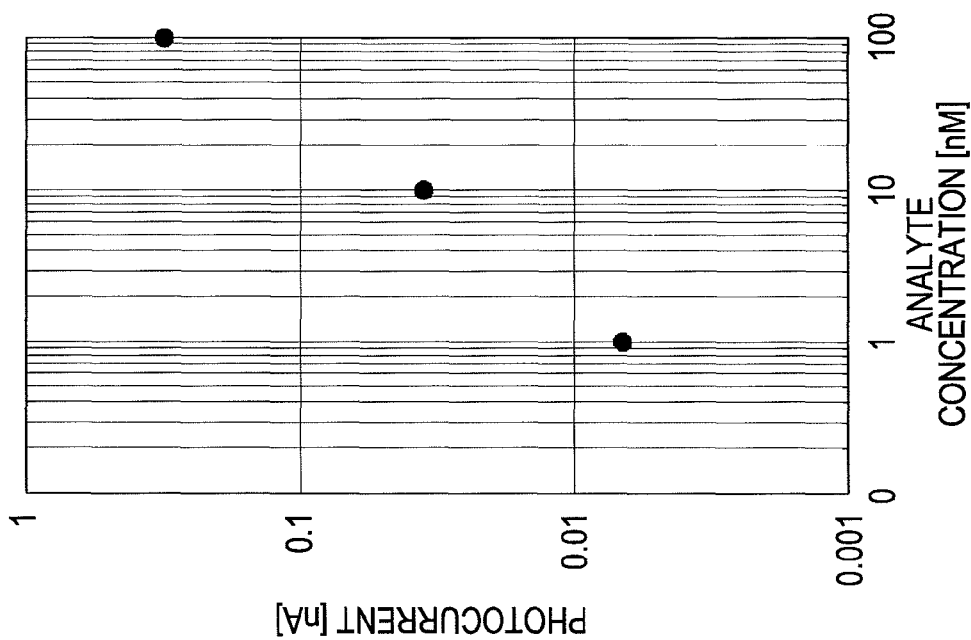
FIG. 37 (A) is a graph showing examined results of a relationship between analyte concentration and photocurrent in Example 2.
Figure 37B:
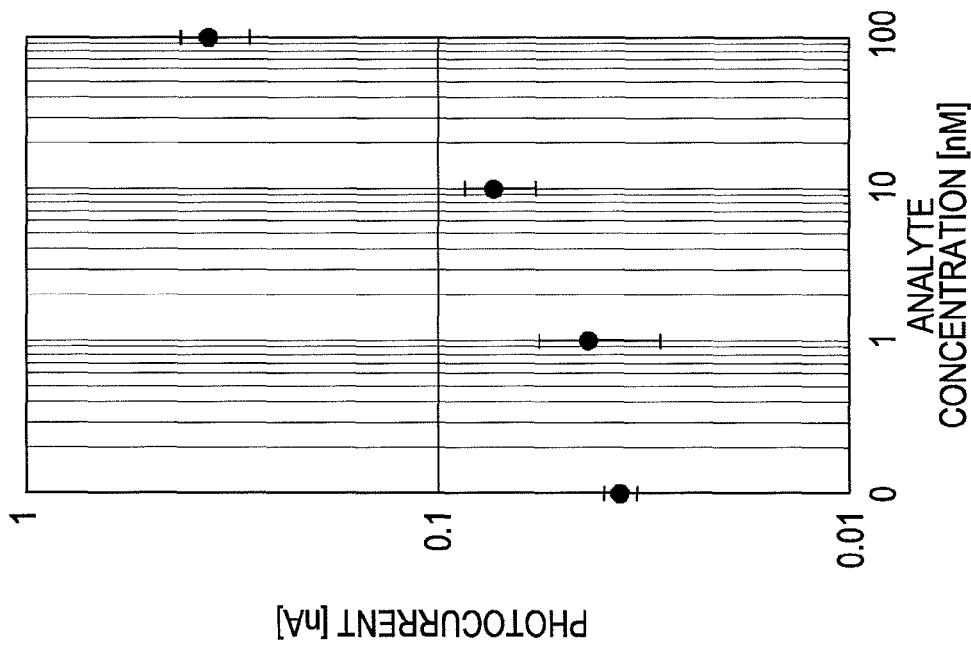

FIG. 37 (A) shows examined results of a relationship between analyte concentration and photocurrent in Example 2. FIG. 37 (B) shows photocurrents after background subtraction at each analyte concentration. Photocurrents after background subtraction were calculated by subtracting the photocurrent obtained with 0 nM analyte from those with 1, 10, or 100 nM analytes shown in FIG. 37 (A) in Example 2. In FIG. 37 (A), the photocurrent shows an average value of the photocurrents (A) when the laser light irradiation positions 1 to 3 were irradiated with laser light.

From the results shown in FIG. 37, it is found that the photocurrent derived from the analyte can be detected depending on the concentration of the analyte by allowing the analyte to be trapped onto the probe holding substrate 338 and attracting it to the working electrode 320.

Example 3

(1) Production of Probe Holding Substrate

A thin film (about 200 nm in thickness) composed of indium oxide containing tin as the adhesion layer 361a for forming the holder 361 was formed on the surface of a substrate body 339a composed of glass ($SiO_2$) by the spattering method. Six gold thin film spots (each thickness: 3.3 nm) were formed as the holding layer 361b for forming the holder 361 on the thin film composed of indium oxide containing tin by the vacuum evaporation using a metal mask with six holes (1 mm in diameter).

Then, the thiolated DNA was covalently-bonded to the gold of the gold thin film by immersing the obtained film forming substrate in the DNA aqueous solution (B) for about 12 hours. Thereafter, the obtained film forming substrate was washed with water and dried. The film forming substrate was immersed in a container into which 100 μL of hybridization buffer [Perfect Hyb, manufactured by Toyobo Co., Ltd.] was poured as a cleaning liquid. The container was allowed to stand for 1 hour in a thermostatic bath set to 45° C. Thereafter, the container was taken out of the thermostatic bath and the cleaning liquid in the container was replaced with 100 μL of a new cleaning liquid. Thus, a DNA holding substrate 339 was obtained [see FIG. 38 (A)]. In the drawing, the positions 7 and 8 are the site where thiolated DNA is not present.

Figure 38A:
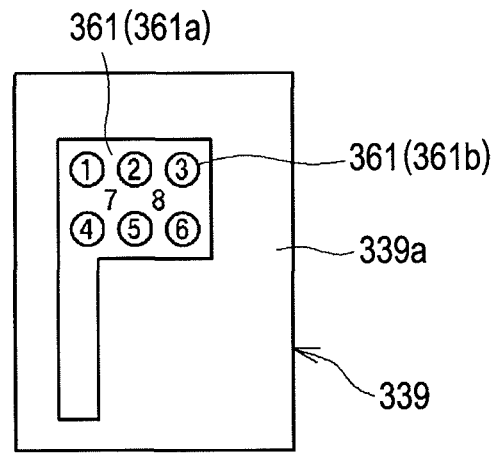
FIG. 38 (A) is a plane explanatory view showing the DNA holding substrate used in Example 3, a DNA holding position and a DNA non-holding position on a holder of the DNA holding substrate.
Figure 38B:
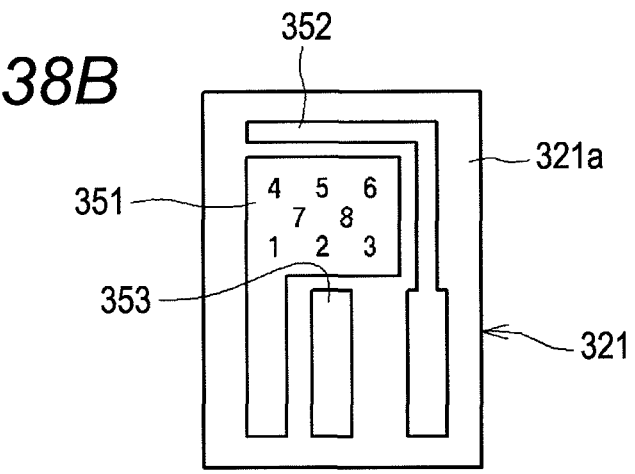
Figure 38C:
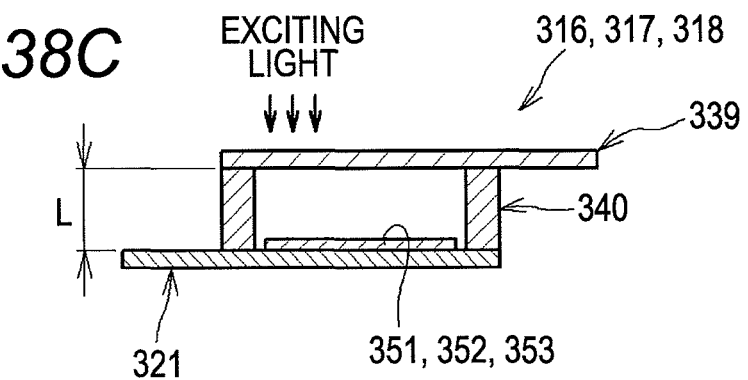

(2) Production of Electrode Substrate Having Working Electrode, Counter Electrode, and Reference Electrode The working electrode 351 formed of a thin film composed of indium oxide containing tin (about 200 nm in thickness) was formed on the surface of the substrate body 321a composed of glass ($SiO_2$) so as to have a pattern shown in FIG. 38 (B) by the spattering method. Further, the counter electrode 352 composed of a platinum thin film and the reference electrode 353 composed of a platinum thin film were formed on the surface of the same substrate body 321a with the working electrode 351 formed so as to have a pattern shown in FIG. 38 (B) by the spattering method. Thus, the electrode substrate 321 was obtained [see FIG. 38 (B)].

(3) Preparation of Solution for Hybridization

DNA (analyte) was labeled with Alexa Fluor 750 and the target substance was obtained. A solution for hybridization was prepared by adding the target substance to a hybridization buffer (Perfect Hyb, manufactured by Toyobo Co., Ltd.) so that the concentration of DNA (analyte) was 10 nM and mixing them.

(4) Detection of Analyte

The cleaning liquid was removed from the container including the DNA holding substrate 339 obtained in (1) above. 100 μL of solution for hybridization was poured into the container. The container was allowed to stand for 3 hours in a thermostatic bath set to 45° C. Thereafter, the DNA holding substrate 339 was cleaned with 0.1 mL of a cleaning solution 1 [composition: 2×SSC (composition of 1×SSC: 0.15 M of sodium chloride, 0.015 M of sodium citrate, pH 7.0), 0.1% by mass of sodium dodecyl sulfate (SDS)] and 0.1 mL of a cleaning solution 2 [composition: 0.1×SSC, 0.1% by mass of SDS] in this order. The DNA holding substrate 339 was washed with ultrapure water and air-dried.

A region about 1 mm² on the working electrode 351 of the electrode substrate 321 was surrounded by a double-sided tape (the gap length was 10 or 30 μm) or silicone rubber (the gap length was 100 μm) of the spacer 340. Then, 0.7 μL (for 10 μm gap), 2.1 μL (for 30 μm gap) or 7 μL (for 100 μm gap) of solution was poured into the space formed with the double-sided tape or silicone rubber.

Then, the space was covered with the DNA holding substrate 339 from the upper side of the electrode substrate 321 and a test chip was assembled. Thereafter, the test chip was allowed to stand at room temperature for 5 minutes. As a result, a holder of a complex containing the analyte and the thiolated DNA in the working electrode of the electrode substrate 321 and the DNA holding substrate 339 was brought into contact with the solution.

A voltage was applied to the working electrode 351 so that the potential of the working electrode 351 was equal to that of the reference electrode 353. At the same time, laser light (wavelength: about 785 nm, intensity: about 13 mW) was illuminated to the working electrode 351 from the opposite side of the surface in contact with the electrolytic solution of the working electrode 351 [see FIG. 38 (C)]. In this case, predetermined positions (laser light irradiation positions 1 to 3, 7 and 8) on the working electrode 351 were irradiated with laser light while blinking the laser light at a predetermined cycle (1 Hz) (on-off) [see FIG. 38 (B)]. The photocurrent (A) generated between the working electrode 351 and the counter electrode 352 as well as a photocurrent (B) generated between the probe holding substrate 339 and the counter electrode 352 at the time of lighting the laser light (when the light was on) after blinking the laser light 20 times were measured.

Figure 39:
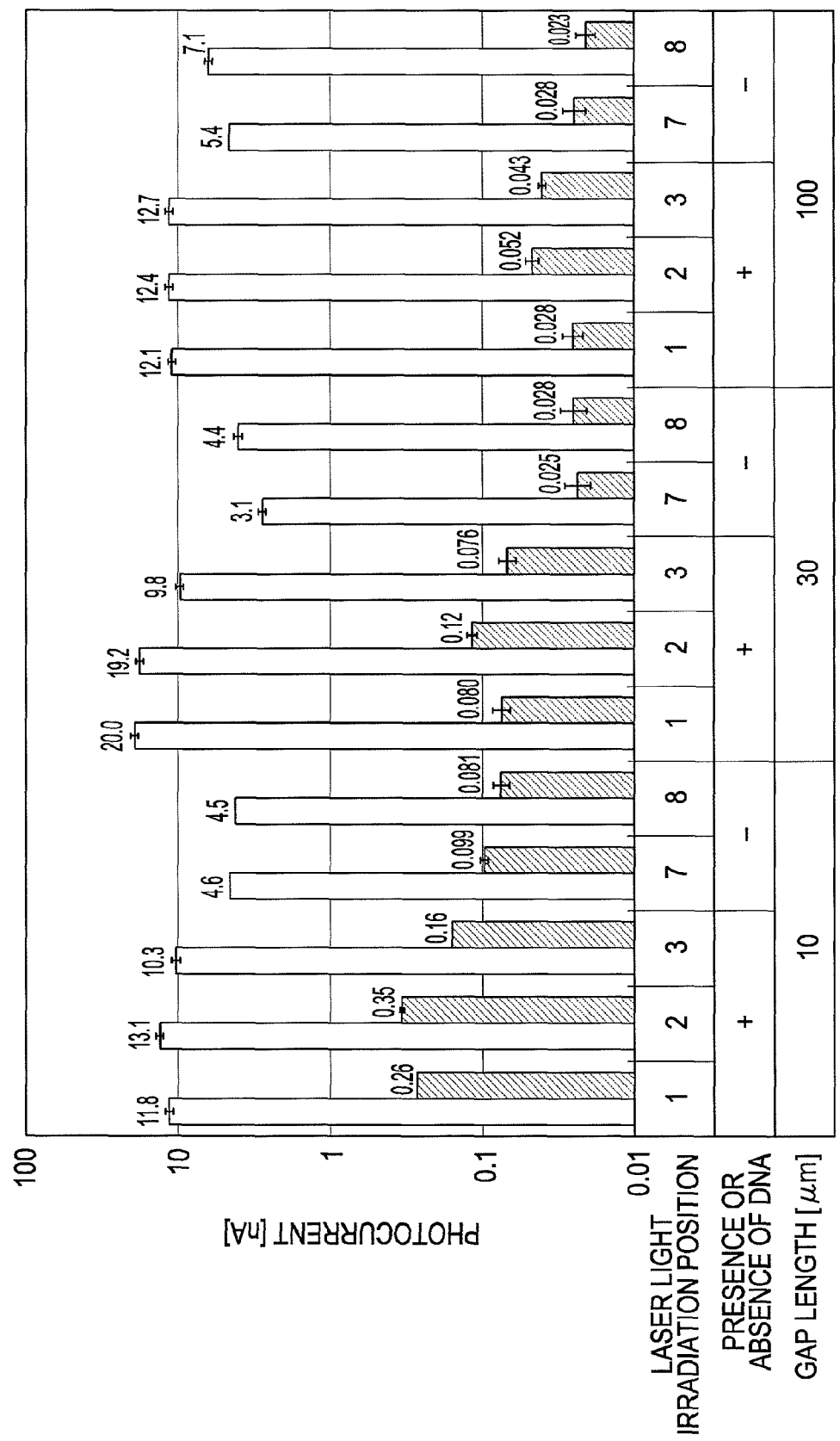
FIG. 39 is a graph showing examined results of a relationship among gap length, laser light irradiation position, and photocurrent in Example 3.

FIG. 39 shows examined results of a relationship among gap length, laser light irradiation position, and photocurrent in Example 3. In FIG. 39, white bars indicate an average value of the photocurrents (B) generated between the probe holding substrate 339 and the counter electrode 352. Shaded bars indicate an average value of the photocurrents (A) generated between the working electrode 351 and the counter electrode 352. In the drawing, the laser light irradiation positions 1 to 3 and 7 and 8 correspond to the laser light irradiation positions shown in FIG. 38 (B).

From the results shown in FIG. 39, it is found that an average value of the photocurrents (B) when irradiating the laser light irradiation positions 1 to 3 to which DNAs (analytes) have been attracted with light is within a range of about 10 to 20 nA. As for the average value of the photocurrents (B) when irradiating the laser light irradiation positions 1 to 3 to which DNAs (analytes) have been attracted with light, a clear correlation with the gap length is not observed.

On the other hand, an average value of the photocurrents (A) when irradiating the laser light irradiation positions 1 to 3 to which DNAs (analytes) have been attracted with light is the highest when the gap length is 10 µm. It can be confirmed that the average value tends to be larger as the gap length is smaller.

Figure 40:
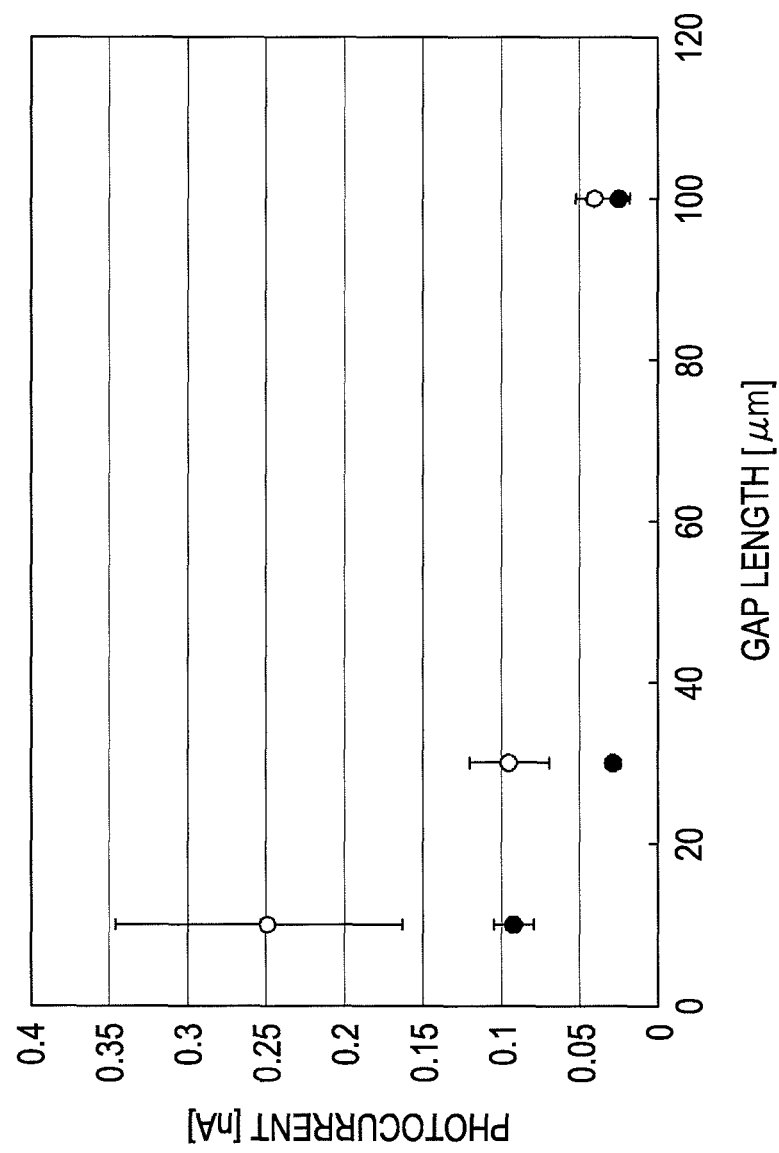
FIG. 40 is a graph showing examined results of a relationship between gap length and photocurrent in Example 3.

Subsequently, a relationship of gap length and photocurrent generated between the working electrode 351 and the counter electrode 352 was examined. FIG. 40 shows examined results of a relationship between gap length and photocurrent. In the drawing, open circles indicate an average value of the photocurrents when light was illuminated to the laser light irradiation positions 1 to 3 where DNAs (analytes) were attracted. Filled circles indicate an average value of the photocurrents when light was illuminated to the laser light irradiation positions 7 and 8 where DNAs (analytes) were not attracted.

From the results shown in FIG. 40, it is found that a difference between the average value of the photocurrents when irradiating the laser light irradiation positions 1 to 3 with light and the average value of the photocurrents when irradiating the laser light irradiation positions 7 and 8 with light becomes larger as the gap length is smaller in the range of the gap length examined. Therefore, this result suggests that the attraction efficiency of DNA (analyte) to the working electrode 351 is improved as the gap length is smaller.

The above results show that the analyte can be well detected by allowing the analyte to be trapped to the probe holding substrate and attracting at least the labeling substance to the working electrode when electrochemically detecting an analyte according to the present invention.

Preparation Example 3

50 µL of Immobilized TCEP GEL (77712, Thermo) was charged into a sampling tube for suppression of protein adsorption. 1 mL of TBS was added thereto, which was mixed. A supernatant was removed by centrifugation and 100 µL of TBS was added thereto. 5 µL of 2 mg/mL Anti-mouse IgG (Fc specific), F(ab')2 (DAKO, E0413) was added to the resultant mixture, which was subjected to Vortex treatment at room temperature for 30 minutes. The supernatant was recovered after the centrifugation and 10-fold diluted with TBS to obtain a solution A (10 µg/mL).

Preparation Example 4

SH-TEG (2.8 M, Aldrich, 673110) was diluted with TBS and 1 mM of a solution B was obtained.

Preparation Example 5

4 g of Block ACE (DS Pharma Biomedical Co., Ltd., UK-B80) was dissolved in 100 mL of TBS and further diluted with TBS to obtain 0.4% of a solution C.

Preparation Example 6

1 mg/mL of mouse IgG technical grade (Sigma, 18765-10 mg) was diluted with 1% BSA/TBS-T to obtain 1 µg/mL of a solution D.

Preparation Example 7

Anti-mouse IgG labeled with Alexa Fluor 750 (Invitrogen, Alexa Fluor 750 goat anti-mouse IgG, A21037) to which gold nanoparticles (average diameter: 40 nm) were bound was produced to obtain a target substance $S_3$ containing labeling substance. 1% BSA/TBS-T solution was added to the obtained production. Thus, a solution E was obtained.

Example 4 and Comparison Test 1

(1) Production of Probe Holding Substrate

A thin film composed of indium oxide containing tin (about 200 nm in thickness) was formed on the surface of the substrate body 208a composed of glass ($SiO_2$) by the spattering method. Thus, the substrate was obtained [see FIG. 41(A)].

(2) Substrate Having Working Electrode, Counter Electrode and Reference Electrode (Electrode Substrate)

The working electrode 351 formed of a thin film composed of indium oxide containing tin (about 200 nm in thickness), the counter electrode 352 composed of a platinum thin film, and the reference electrode 353 composed of a platinum thin film were formed on the surface of the substrate body 321a composed of glass ($SiO_2$) by the spattering method. Thus, an electrode substrate 321 was obtained [see FIG. 41(B)].

(3) Silane Coupling Treatment 3-mercaptopropyltriethoxysilane (MPTES), a silane coupling agent, was added at a concentration of 1% by volume to obtain a solution F. The substrate obtained in (1) above was immersed in the solution F for 1 hour. Thereafter, the substrate was washed with toluene and dried. Thus, the substrate coated with MPTES for forming the holder 211 was formed.

(4) Immobilization of Antibody

30 µL of the solution A obtained in Preparation example 3 was dropped onto the substrate obtained in (3) above. The substrate was allowed to stand at 4° C. and high humidity overnight.

(5) Blocking Treatment 1

After washing with 50 µL of TBS, 30 µL of the solution B obtained in Preparation example 4 was dropped onto the substrate obtained in (4) above. The substrate was allowed to stand at 4° C. and high humidity overnight.

(6) Blocking Treatment 2

After washing with 50 μL of TBS, 30 μL of the solution C obtained in Preparation example 5 was dropped onto the substrate obtained in (5) above. The substrate was allowed to stand at 23° C. and high humidity for 30 minutes.

(7) Antigen-Antibody Reaction

After removal of the solution C, 30 μL of the 1% BSA/TBS-T solution (comparison test 1) or 30 μL of the solution D obtained in Preparation example 6 (Example 4) was dropped onto the substrate obtained in (6) above. The substrate was allowed to stand at 23° C. and high humidity for 1 hour (see FIG. 19 (A)). Thus, a probe holding substrate was obtained.

(8) Trapping of Target Substance $S_3$ Containing Labeling Substance

After removal of the 1% BSA/TBS-T solution (comparison test 1) or the solution D (Example 4), the substrate was washed with 50 μL of TBS-T. Thereafter, 30 μL of the solution E obtained in Preparation example 7 was dropped onto the probe holding substrate. The probe holding substrate was allowed to stand at 23° C. and high humidity for 1 hour. After 1 hour, the probe holding substrate was washed twice with 50 μL of TBS-T. It was further washed with 50 μL of ultrapure water and air-dried (see FIGS. 19 (B) and (C)).

(9) Detection of Photocurrent

A double-sided tape was placed around the electrode substrate 321 obtained in (2) above so as to form a 0.01-mm-thick side wall. The space surrounded by the electrode substrate 321 and the double-sided tape was filled with 0.8 μL of the electrolytic solution obtained in Preparation example 2. The space filled with the electrolytic solution was covered with the probe holding substrate obtained in (8) above from the upper side of the electrode substrate 321 (see FIG. 41 (C)). As a result, the working electrode, the counter electrode, and the reference electrode were brought into contact with the electrolytic solution (see FIG. 19 (D)). Subsequently, the lead of the working electrode and the lead of the counter electrode were connected to the ammeter.

Laser light (wavelength: 781 nm, laser light source with an output power of 13 mW) was illuminated from the side of the probe holding substrate to the electrode substrate 321 (see FIG. 41 (D)). The labeling substance is excited by photo-irradiation, thereby generating electrons. Then, electrons are transported to the working electrode, resulting in generation of a current between the working electrode and the counter electrode. Then, the current was measured.

It can be confirmed that the photocurrent value obtained in example 4 (0.073±0.017 nA, n=2) is significantly larger than the photocurrent value obtained in comparison test 1 (0.029±0.005 nA, n=2). As a result, even when gold nanoparticles are used, the photocurrent value depending on the amount of the target substance can be measured.

What is claimed is:

1. A method of electrochemically detecting a target substance containing a labeling substance, comprising:
   (1-1) bringing the target substance containing the labeling substance into contact with a probe holding substrate in which a probe for trapping the target substance containing the labeling substance is held on the probe holding substrate and allowing the target substance containing the labeling substance to be trapped by the probe;
   (1-2) detaching the labeling substance, the target substance or a moiety which is a part of the target substance and contains the labeling substance from the probe holding substrate obtained in the process (1-1) and attracting to a working electrode in which a trapping substance for trapping the labeling substance, the target substance or the moiety which is a part of the target substance and contains the labeling substance is not present, wherein the working electrode and the probe holding substrate are arranged so as to be opposed to each other with a space therebetween; and
   (1-3) electrochemically detecting the labeling substance, the target substance or the moiety which is a part of the target substance and contains the labeling substance which has been attracted to the working electrode in the process (1-2),
   wherein the probe holding substrate in the process (1-1) is a probe holding substrate in which the probe for trapping the target substance containing the labeling substance is held on a substrate body through a holder, and
   wherein the holder has a first layer composed of a metal that is dissolved in a solution or an alloy thereof and the probe which has trapped the target substance containing the labeling substance is detached from the substrate body of the probe holding substrate by bringing the solution into contact with the holder in the process (1-2).

2. The method according to claim 1, wherein the first layer is comprised of gold and palladium and the solution is a solution containing iodine or an iodide.

3. The method according to claim 1, wherein the labeling substance, the target substance or a moiety which is a part of the target substance and contains the labeling substance is attracted to the working electrode in which the trapping substance is not present by differences in polarity in the process (1-2).

4. The method according to claim 1, wherein the labeling substance, the target substance or a moiety which is a part of the target substance and contains the labeling substance is attracted to the working electrode in which the trapping substance is not present by electrophoresis in the process (1-2).

5. The method according to claim 1, wherein the labeling substance is an electrochemically or photochemically active substance.

6. A method of electrochemically detecting a target substance containing a labeling substance, comprising:
   (1-1) bringing the target substance containing the labeling substance into contact with a probe holding substrate in which a probe for trapping the target substance containing the labeling substance is held on the probe holding substrate and allowing the target substance containing the labeling substance to be trapped by the probe;
   (1-2) detaching the labeling substance, the target substance or a moiety which is a part of the target substance and contains the labeling substance from the probe holding substrate obtained in the process (1-1) and attracting to a working electrode in which a trapping substance for trapping the labeling substance, the target substance or the moiety which is a part of the target substance and contains the labeling substance is not present, wherein the working electrode and the probe holding substrate are arranged so as to be opposed to each other with a space therebetween; and
   (1-3) electrochemically detecting the labeling substance, the target substance or the moiety which is a part of the target substance and contains the labeling substance which has been attracted to the working electrode in the process (1-2),
   wherein the probe holding substrate in the process (1-1) is a probe holding substrate in which the probe for trapping the target substance containing the labeling substance is held on a substrate body through a holder, and wherein the holder has a first layer composed of a metal that is dissolved in a solution or an alloy thereof and a second layer which is provided among the first layer and the substrate body and makes the first layer stick to the substrate body, and the probe which has trapped the target substance containing the labeling substance is detached from the substrate body of the probe holding substrate by bringing the solution into contact with the holder in the process (1-2).

7. The method according to claim 6, wherein the second layer is comprised of a substance that is selected from the group consisting of platinum, palladium, titanium, chromium, nickel, indium tin oxide, and indium oxide, and is different from the substances for forming the first layer.

8. The method according to claim 6, wherein the first layer is comprised of gold and palladium and the solution is a solution containing iodine or an iodide.

9. The method according to claim 6, wherein the labeling substance, the target substance or a moiety which is a part of the target substance and contains the labeling substance is attracted to the working electrode in which the trapping substance is not present by differences in polarity in the process (1-2).

10. The method according to claim 6, wherein the labeling substance, the target substance or a moiety which is a part of the target substance and contains the labeling substance is attracted to the working electrode in which the trapping substance is not present by electrophoresis in the process (1-2).

11. The method according to claim 6, wherein the labeling substance is an electrochemically or photochemically active substance.

* * * * *